(12) United States Patent
Ray et al.

(10) Patent No.: US 8,945,595 B2
(45) Date of Patent: Feb. 3, 2015

(54) INSECT REPELLENT AND ATTRACTANTS

(75) Inventors: Anandasankar Ray, Riverside, CA (US); Stephanie Lynn Turner, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 644 days.

(21) Appl. No.: 12/398,164

(22) Filed: Mar. 4, 2009

(65) Prior Publication Data

US 2010/0226949 A1 Sep. 9, 2010

(51) Int. Cl.
*A01N 37/02* (2006.01)
*A01N 31/02* (2006.01)
*A01N 35/02* (2006.01)

(52) U.S. Cl.
CPC .............. *A01N 37/02* (2013.01); *A01N 31/02* (2013.01); *A01N 35/02* (2013.01)
USPC ........... 424/403; 424/405; 514/675; 514/693; 514/724

(58) Field of Classification Search
CPC ....... A01N 25/00; A01N 25/06; A01N 31/02; A01N 35/02; A01N 35/06; A01N 37/02; A61K 8/02; A61K 8/046; A61K 8/31; A61K 8/34; A61K 8/35; A61K 8/37; A61K 9/02; A61K 9/12; A61Q 17/02; Y10S 2/00; D06M 13/224; C07C 31/125; C07C 47/02; C07C 49/04; C07C 69/003
USPC .............. 424/405, 45, 84; 514/506, 675, 693, 514/724, 739, 762, 764
See application file for complete search history.

(56) References Cited

U.S. PATENT DOCUMENTS

| | | | | |
|---|---|---|---|---|
| 6,267,953 | B1 * | 7/2001 | Bernier et al. | 424/84 |
| 6,372,804 | B1 | 4/2002 | Ikemoto et al. | |
| 6,800,279 | B2 * | 10/2004 | Bernier et al. | 424/84 |
| 2002/0028191 | A1 * | 3/2002 | Bernier et al. | 424/84 |
| 2004/0223998 | A1 * | 11/2004 | Iyer et al. | 424/405 |
| 2006/0193881 | A1 * | 8/2006 | Bedoukian | 424/405 |
| 2007/0157323 | A1 | 7/2007 | Carlson et al. | |

FOREIGN PATENT DOCUMENTS

| | | |
|---|---|---|
| WO | 00/65910 A1 | 11/2000 |
| WO | WO-2010102049 A2 | 9/2010 |
| WO | WO-2010102049 A3 | 9/2010 |

OTHER PUBLICATIONS

H. D. Douglas, IIII J.E. Co, T. H. Jones, W. E. Conner and J. F. Day, "Chemical Odorant of Colonial Seabird Repels Mosquitoes", Journal of Medical Entomology, 2005, 42(4), 647-651.*
H.D. Douglas et al., "Chemical Odorant of Colonial Seabird Repels Mosquitoes," 2005, J. Med. Entomol., 42(4):647-651.*
International Application Serial No. PCT/US2010/026108, International Preliminary Report on Patentability mailed Sep. 15, 2011, 8 pgs.
Min, Kwon Oh. International Search Report and written Opinion. International Application No. PCT/US2010/026108. Date of Mailing of the international Search Report: Oct. 19, 2010.

(Continued)

*Primary Examiner* — Jane C Oswecki
(74) *Attorney, Agent, or Firm* — Schwegman Lundberg & Woessner, P.A.

(57) ABSTRACT

The disclosure provides compounds useful as insect repellents and compositions comprising such repellents. The disclosure further provides insect traps.

16 Claims, 18 Drawing Sheets

(56) References Cited

OTHER PUBLICATIONS

International Preliminary Report on Patentability received for PCT Patent Application No. PCT/US2010/026108, mailed on Sep. 15, 2011, 8 pages.

Extended European Search Report and European Search Opinion received for European Patent Application No. 10749292.8, mailed on Apr. 2, 2013, 7 pages.

Lu et al., "Odor Coding in the Maxillary Palp of the Malaria Vector Mosquito Anopheles Gambiae", Current Biology, vol. 17, No. 18, Sep. 18, 2007, pp. 1533-1544.

Caplus Accesion No. 1950 : 34271, Smith et al., "Effectiveness of Repellents Applied to Clothing for Protection against Salt-Marsh Mosquitoes", Journal of Economic Entomologym vol. 42, 1949, pp. 439-444, retrieved on Nov. 20, 2008 (4 pages of document).

\* cited by examiner (d)

(e)

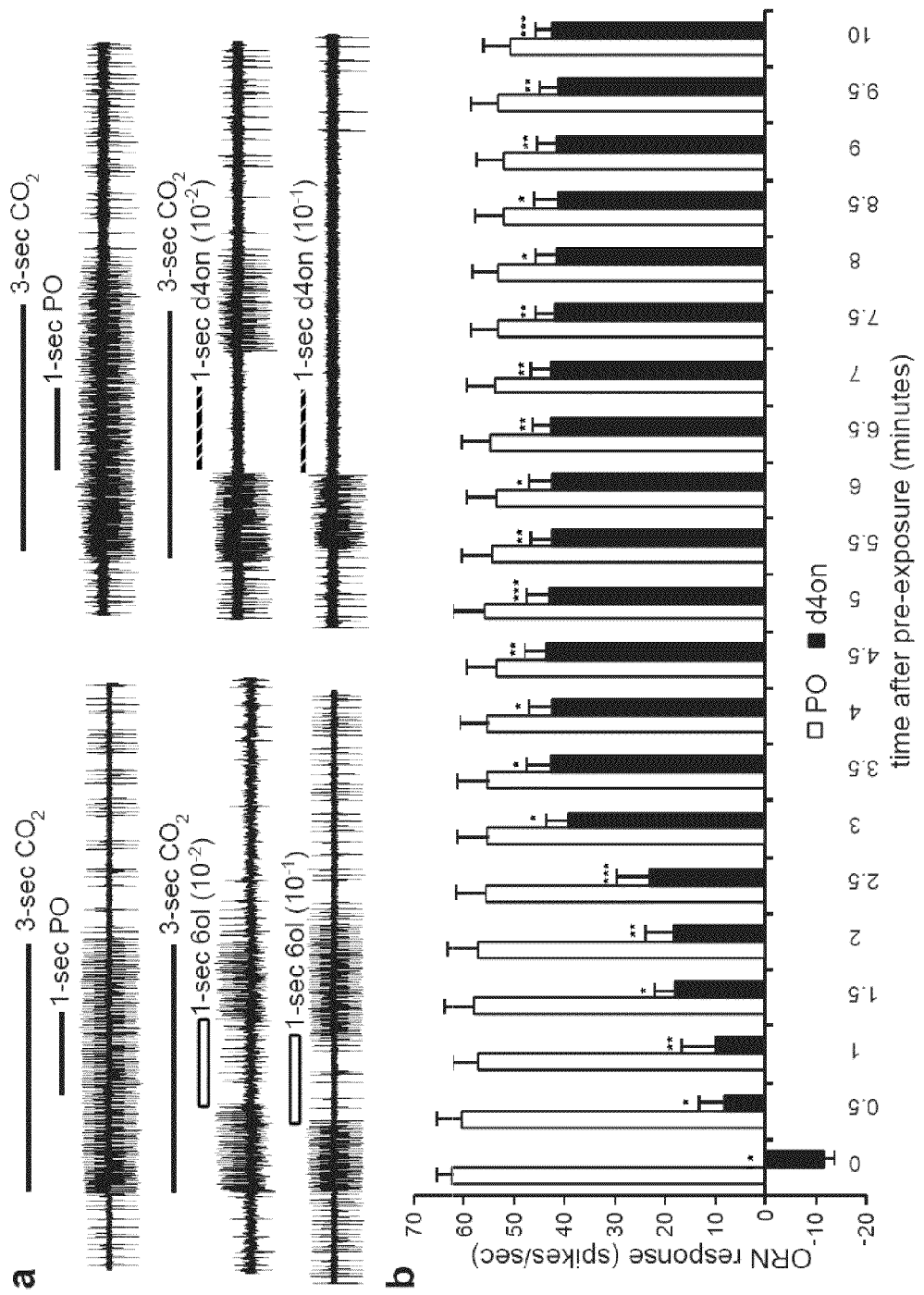
FIGURE 13C-D

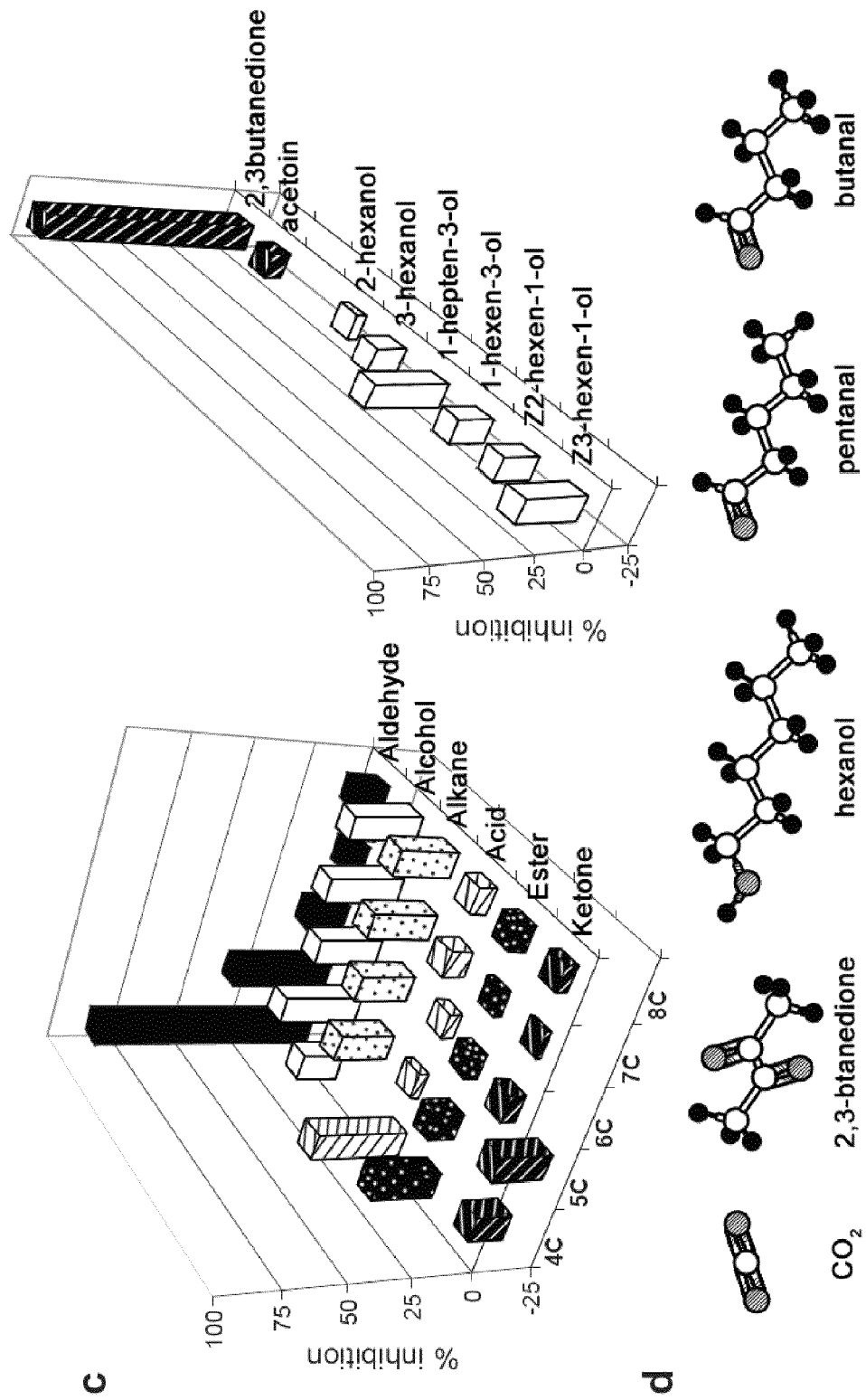
FIGURE 13C-D 1-hetan-3-ol

Heptanal

Octanoic acid 2,3-butanedione

Butyric acid

Hexanal

Heptanol

Pentanal

Pentanol

Butanal

Hexanol

Butanone

INSECT REPELLENT AND ATTRACTANTS

TECHNICAL FIELD

The disclosure provides compounds useful as insect repellents and compositions comprising such repellents. The disclosure further provides compounds useful as insect traps.

BACKGROUND

Numerous insects are vectors for disease. Mosquitoes in the genus *Anopheles* are the principle vectors of malaria, a disease caused by protozoa in the genus *Trypanosoma*. *Aedes aegypti* is the main vector of the viruses that cause Yellow fever and Dengue. Other viruses, the causal agents of various types of encephalitis, are also carried by *Aedes* spp. mosquitoes. *Wuchereria bancrofti* and *Brugia malayi*, parasitic roundworms that cause filariasis, are usually spread by mosquitoes in the genera *Culex, Mansonia*, and *Anopheles*.

Horse flies and deer flies may transmit the bacterial pathogens of tularemia (*Pasteurella tularensis*) and anthrax (*Bacillus anthracis*), as well as a parasitic roundworm (*Loa loa*) that causes loiasis in tropical Africa.

Eye gnats in the genus *Hippelates* can carry the spirochaete pathogen that causes yaws (*Treponema pertenue*), and may also spread conjunctivitis (pinkeye). Tsetse flies in the genus *Glossina* transmit the protozoan pathogens that cause African sleeping sickness (*Trypanosoma gambiense* and *T. rhodesiense*). Sand flies in the genus *Phlebotomus* are vectors of a bacterium (*Bartonella bacilliformis*) that causes Carrion's disease (oroyo fever) in South America. In parts of Asia and North Africa, they spread a viral agent that causes sand fly fever (pappataci fever) as well as protozoan pathogens (*Leishmania* spp.) that cause Leishmaniasis.

SUMMARY

The disclosure provides an insect repellent comprising: a compound selected from the group consisting of a 4 to 6 carbon aldehyde, a 5 to 8 carbon alcohol, a 3 to 8 carbon mono- or di-ketone, and any combination thereof. In one embodiment, the 4 to 6 carbon aldehyde is selected from the group consisting of butanal, pentanal, and hexanal. In another embodiment, the 5 to 8 carbon alcohol is selected from the group consisting pentanol, hexanol, cyclohexanol, Z-3-hexen-1-ol, Z-2-hexen-1-ol, 1-hexen-3-ol, 1-hepten-3-ol, 3-hexanol, and 2-hexanol. In a further embodiment, the 3 to 8 carbon mono- or di-ketones is selected from a butanedione (2,3-butanedione) and pentanedione. In a specific embodiment, the compound is 2,3-butanedione. The compound may be formulated into a repellent for topical application such as in the form of a lotion, cream, spray or dust. In another embodiment, the repellent comprises a vaporizer, a treated mat, treated outerwear, an oil, a candle, or a wicked apparatus.

The disclosure also provides an insect trap comprising a compound selected from the group consisting of a 4 to 6 carbon aldehyde, a 5 to 8 carbon alcohol, a 3 to 8 carbon mono- or di-ketone, and any combination thereof. In one embodiment, the 4 to 6 carbon aldehyde is selected from the group consisting of butanal, pentanal, and hexanal. In another embodiment, the 5 to 8 carbon alcohol is selected from the group consisting pentanol, hexanol, cyclohexanol, Z-3-hexen-1-ol, Z-2-hexen-1-ol, 1-hexen-3-ol, 1-hepten-3-ol, 3-hexanol, and 2-hexanol. In a further embodiment, the 3 to 8 carbon mono- or di-ketones is selected from a butanedione (2,3-butanedione) and pentanedione.

The disclosure also provides a method of repelling an insect pest, comprising applying to a subject, in an amount effect to repel said insect pest, a compound selected from the group consisting of a 4 to 6 carbon aldehyde, a 5 to 8 carbon alcohol, a 3 to 8 carbon mono- or di-ketone, and any combination thereof. In one embodiment, the 4 to 6 carbon aldehyde is selected from the group consisting of butanal, pentanal, and hexanal. In another embodiment, the 5 to 8 carbon alcohol is selected from the group consisting pentanol, hexanol, cyclohexanol, Z-3-hexen-1-ol, Z-2-hexen-1-ol, 1-hexen-3-ol, 1-hepten-3-ol, 3-hexanol, and 2-hexanol. In a further embodiment, the 3 to 8 carbon mono- or di-ketones is selected from a butanedione (2,3-butanedione) and pentanedione.

The disclosure also provides a method of repelling an insect pest, comprising applying to a subject an active compound in an amount effective to repel the insect pest; wherein said insect pest is selected from the group consisting of flies and mosquitoes; and wherein the compound is selected from the group consisting of a 4 to 6 carbon aldehyde, a 5 to 8 carbon alcohol, a 3 to 8 carbon mono- or di-ketone, and compositions comprising any combination thereof.

The disclosure provides a method of repelling mosquitoes, comprising applying to a subject an effective amount of a repellant comprising a compound selected from the group consisting of a 4 to 6 carbon aldehyde, a 5 to 8 carbon alcohol, and a 3 to 8 carbon mono- or di-ketone.

In various embodiments of the disclosure a subject can be treated with the repellent of the disclosure. In some embodiments, the subject is a human. In other embodiment, the subject is a domesticated or livestock animal. The methods and compositions of the disclosure can be used to modify the $CO_2$ homing activity of mosquitoes or repel mosquitoes. The mosquitoes can be selected from the group consisting of Tiger mosquitoes, *Aedes aboriginis, Aedes Aegypti, Aedes, albopictus, Aedes cantator, Aedes sierrensis, Aedes sollicitans, Aedes squamiger, Aedes sticticus, Aedes vexans, Anopheles quadrimaculatus, Culex pipiens*, and *Culex quinquefaxciatus*.

The details of one or more embodiments of the disclosure are set forth in the accompanying drawings and the description below. Other features, objects, and advantages of the disclosure will be apparent from the description and drawings, and from the claims.

(c) 1 sec of indicated odor is puffed to *Anopheles gambiae*. (d) butanone and (e) 2,3-butanedione are given to Culex quinquefasciatus at the indicated concentrations. PO=paraffin oil. n=5. Baseline activity subtracted. Error bars indicate SEM.

FIG. 10A-D show inhibitory odors significantly reduce avoidance behavior to $CO_2$. (a) A t-maze is used to show preference to a test odor or to a solvent. Flies are starved 24 hrs prior to assay. All assays performed for 1-min in the dark. A negative preference index indicates avoidance. (a) Flies in a T-maze were offered a choice between a 15 ml tube infused with 0.1ml of $CO_2$ prior to start of assay, and another that was infused with air. (b) wildtype and Or83b−/− flies were presented with $CO_2$, a mixture of $CO_2$ and 2,3-butanedione (d4on), or d4on alone. (c) Flies were exposed to 10 ul d4on $10^{-2}$ for 1 min, allowed to recover for 2 min in clean air and then assayed for avoidance to $CO_2$. A control exposure to 1 min of 2-methylphenol (2 mpol) at $10^{-2}$ and then a recovery period of 2 min is also assayed for avoidance behavior to $CO_2$. (d) Flies are exposed to d4on for 1 min, allowed to recover for 2 min, and then assayed for behavior to ethyl acetate (2AC). Behavior to 2AC without pre-exposure is also measured. N=6-9 (~40 flies/trial). Error bars indicate SEM.

FIG. 11A-D shows the innate avoidance response of *Drosophila* to $CO_2$ is suppressed in certain contexts. a, Attraction to the T-maze arm containing headspace from complex odour sources quantified as a mean Preference Index. n=6 trials (~40 flies each), error bars=s.e.m. b, Proposed models for context-dependent modification of avoidance behavior to $CO_2$. c, Representative traces of activity of ab1C neurons using single-sensillum electrophysiology in mutant flies. Odourants were tested at $10^{-2}$ dilution. Bars indicate a 0.5-sec stimulus period. d, Mean odourant responses. Odourants were tested at $10^{-2}$ dilution in paraffin oil. Bars represent values after subtraction of mean response to paraffin oil. n=3, error bars=s.e.m.

Figure 12:
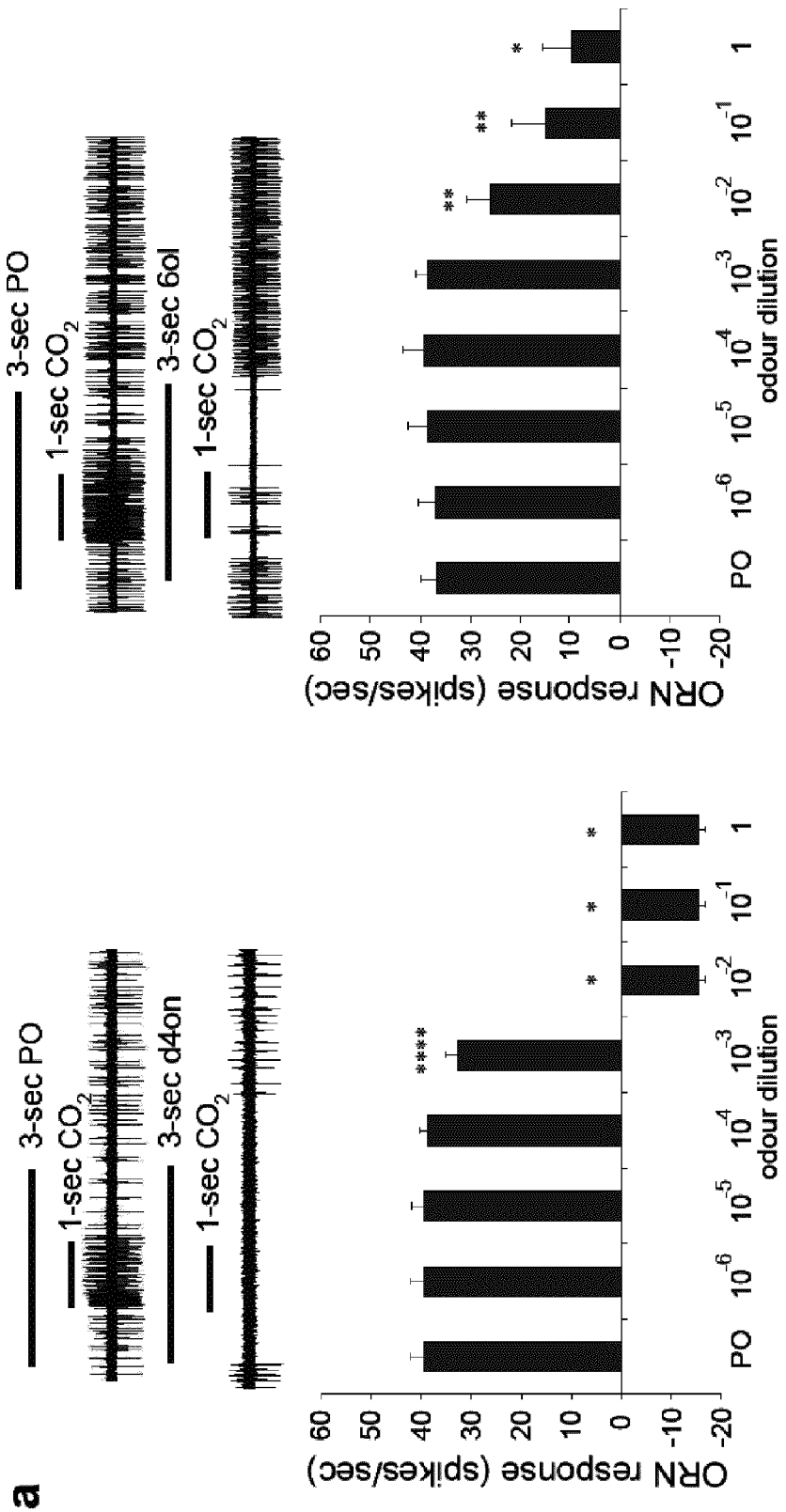
Figure 12:
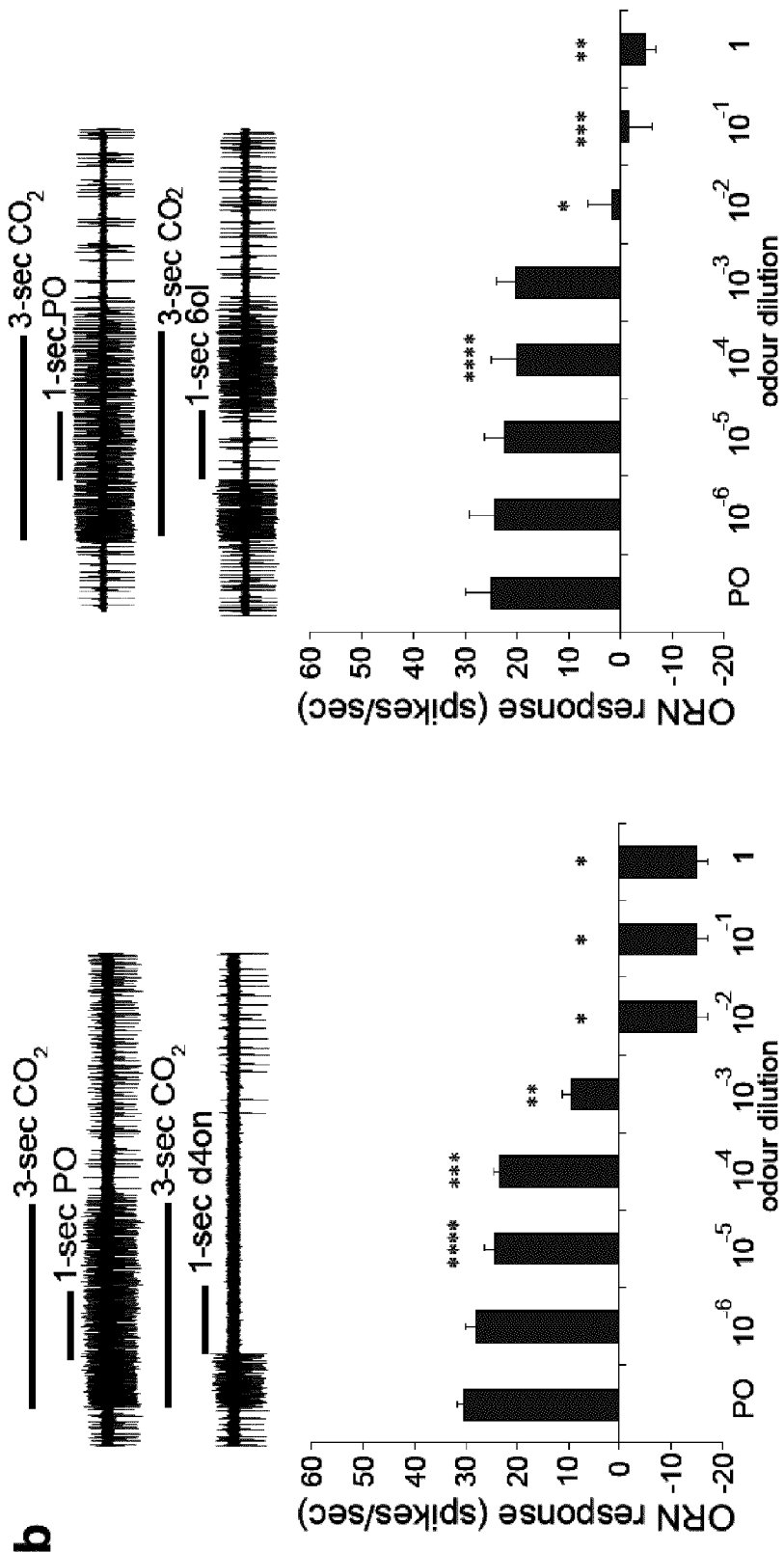
Figure 12:
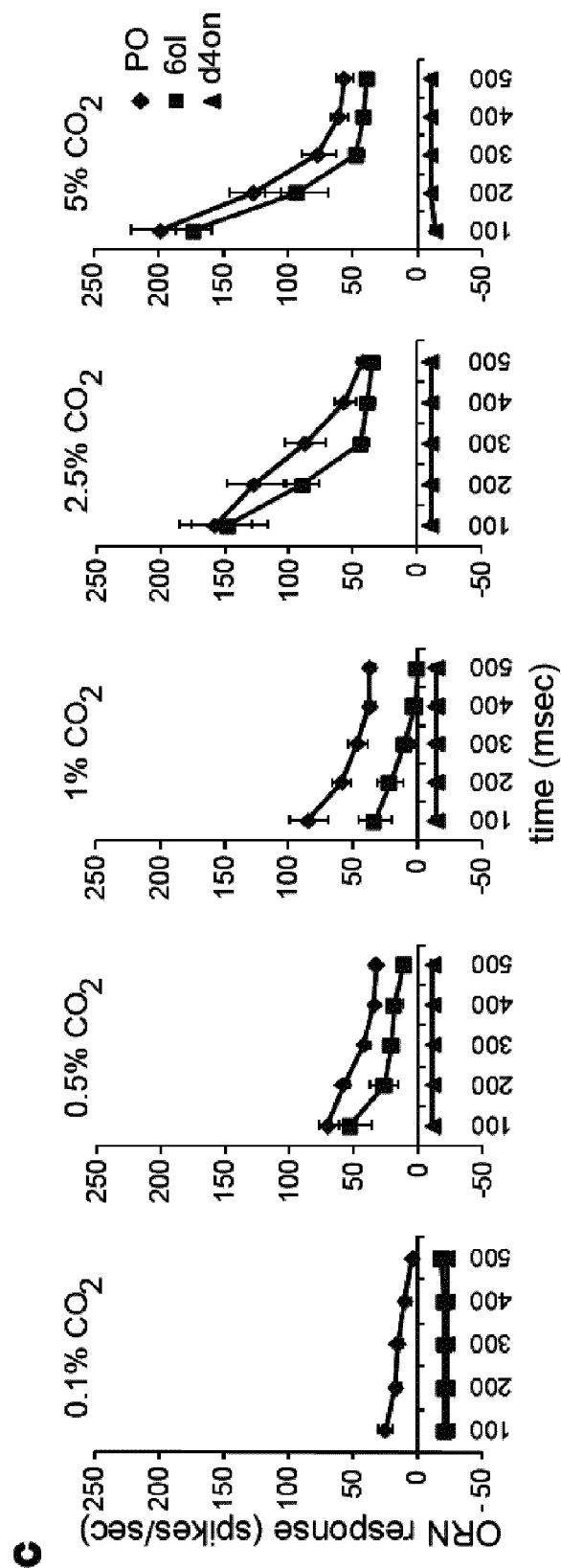
Figure 13E:
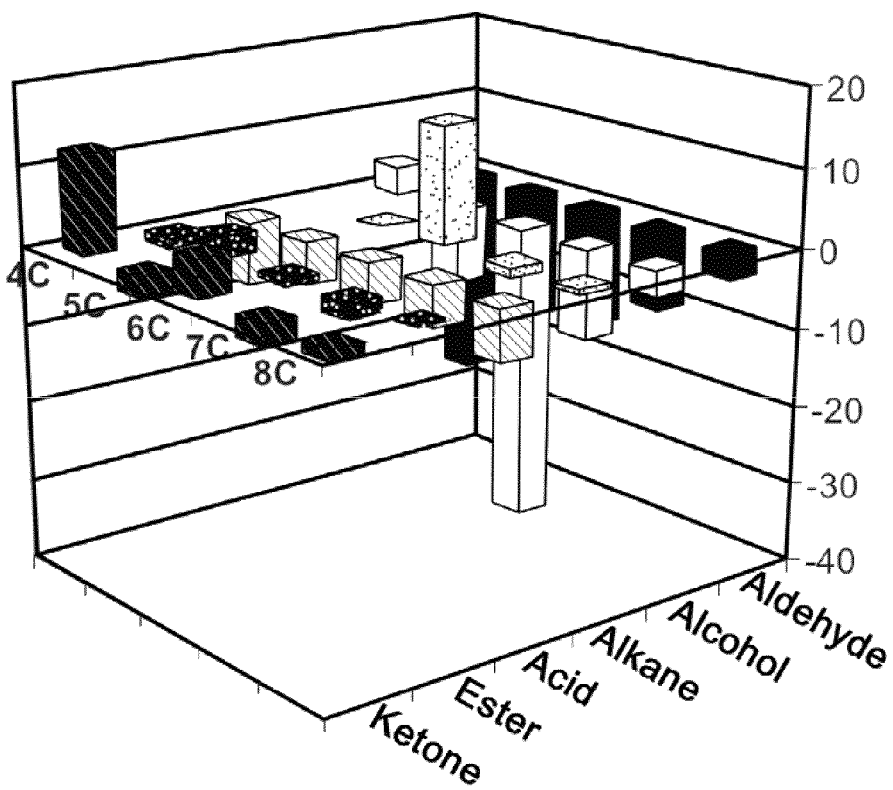
Figure 13F:
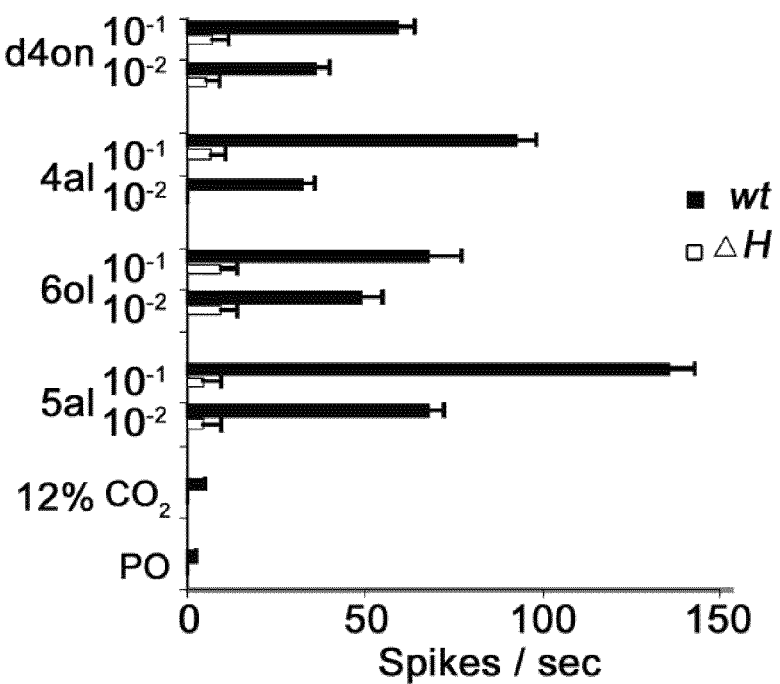

FIG. 12A-C shows inhibitory odours dramatically reduce response to $CO_2$ in the ab1C neurons. Representative traces (top) and mean responses (bottom) from single-sensillum electrophysiology of ab1 sensilla in mutant flies; spikes represent activity of the ab1C neuron. a, 3-sec stimulus of odourant overlaid with a 1-sec application of 0.3% $CO_2$. b, 3-sec stimulus of 0.3% $CO_2$ overlaid with a 1-sec application of odourant. PO=paraffin oil, d4on=2,3-butanedione, 6ol=1-hexanol. n=6, error bars=s.e.m. Spikes per second were counted during the 1-sec stimulus period, and spontaneous activity subtracted. (For data in a and b, T-test, *P<0.001, P<0.005, *P<0.01, ****P<0.05) c, ab1C responses to indicated concentrations of $CO_2$ in the presence of solvent (PO), 1-hexanol (6ol) or 2,3-butanedione (d4on). Odourants were tested at $10^{-1}$ dilution. Firing rates were counted in consecutive 0.1-sec bins. n=3, error bars=s.e.m.

FIG. 13A-F shows response dynamics and structural analysis of inhibitory odourants. a, Representative traces representing activity of ab1C neurons. Bars indicate stimulus periods for 0.3% $CO_2$, and overlays with 1-hexanol (6ol) or 2,3-butanedione (d4on) at the indicated concentrations. b, Recovery of ab1C responsiveness to a 0.5-sec, 0.3% $CO_2$ stimulus applied every 30-sec after initial treatment with 3-sec stimulus of either d4on ($10^{-1}$) or paraffin oil (PO). n=5, error bars=s.e.m., (T-test, *P<0.005, <0.01, *P<0.05). c, $CO_2$ response inhibition by structurally related compounds. A 3-sec stimulus of 0.3% $CO_2$ was delivered in combination with 1-sec application of indicated odourant ($10^{-2}$) as in a. Percent increase or decrease in mean ab1C response was calculated relative to mean response of paraffin oil. n=5. d, Structures of $CO_2$ and the 4 strongest antagonists. e-f, show mean odourant responses. e, Odourants were tested on ab1C neurons in Or83b2 flies at $10^{-2}$ dilution in paraffin oil. Bars represent values after subtraction of mean response to paraffin oil. n=3. f, Odourants at indicated concentrations were tested on ab3A neuron in wild-type (wt) and ΔHalo (AH) mutants that lack Or22a and Or22b. Bars represent values after subtraction of spontaneous activity. n=5, error bars=s.e.m.

Figure 14:
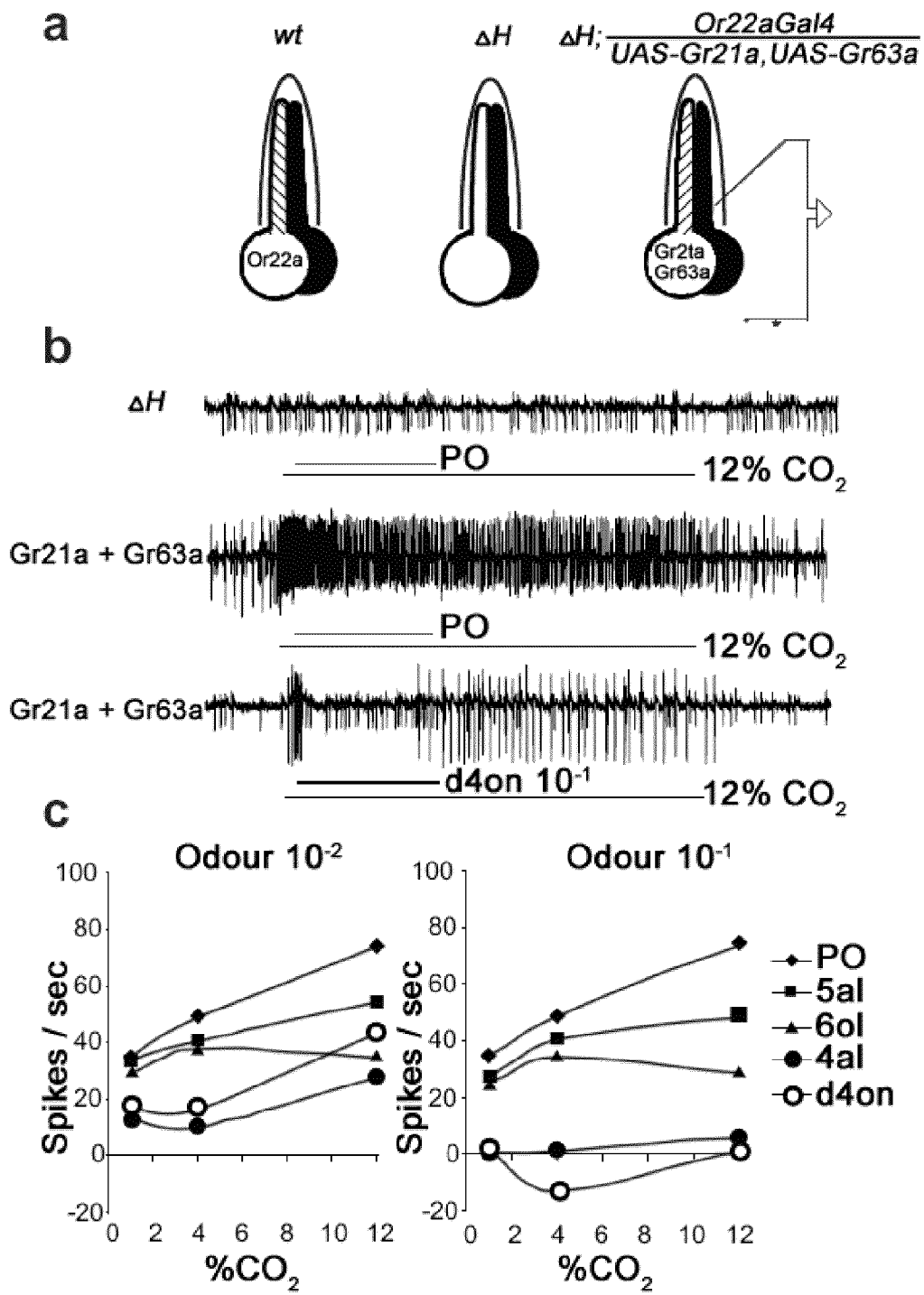

FIG. 14A-C shows inhibitory odourants directly affect $CO_2$ response of Gr21a/Gr63a in a heterologous system. a, Schematic illustrating "empty neuron" system used for heterologous expression of Gr21a and Gr63a in ab3A neurons. b, Representative traces of recordings from ab3 sensilla. Large spikes represent the response of the delta-ab3A cell expressing Gr21a and Gr63a. Bars indicate stimulus periods of 12% $Co_2$, overlaid with paraffin oil (PO) or 2,3-butanedione (d4on) at dilution of $10^{-1}$. c, Concentration-dependent responses of ab3A neuron to CO2, and binary mixtures of $CO_2$ with odourants at indicated concentrations. 1-butanal (4al), 1-pentanal (5al), 1-hexanol (6ol). Stimuli were applied as in b. n=5, error bars=s.e.m.

Figure 15:
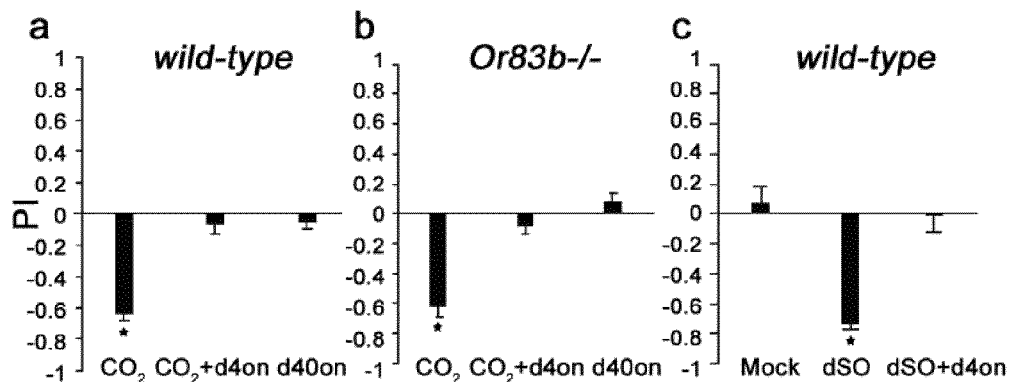

FIG. 15 shows avoidance behavior to $CO_2$ and *Drosophila* stress odour is inhibited by food odourants. T-maze behavior assay: a, Mean Preference Index (PI) of wild-type flies, given a choice between room air in 15 ml tube and either 0.1 ml of pure $CO_2$ in a 15 ml tube ($CO_2$), or binary mixtures of 0.1 ml pure $CO_2$ and 1-hexanol ($CO_2$+6ol) at $10^{-1}$ dilution or 2,3-butanedione ($CO_2$+d4on) at $10^{-2}$ dilution, also in 15 ml tubes (see Methods). b, Mean PI of mutant flies given choices as in a. c, Mean PI of wild-type flies given choices between room air and odour collected from 70 untreated flies (mock), or 70 vortexed "emitter" flies of *Drosophila* stress odour (dSO), or mixtures of dSO with indicated odourants. n=6-9 trials (~40 flies each), error bars=s.e.m. (T-test, *P<0.0001, P<0.005, *P<0.05).

Figure 16:
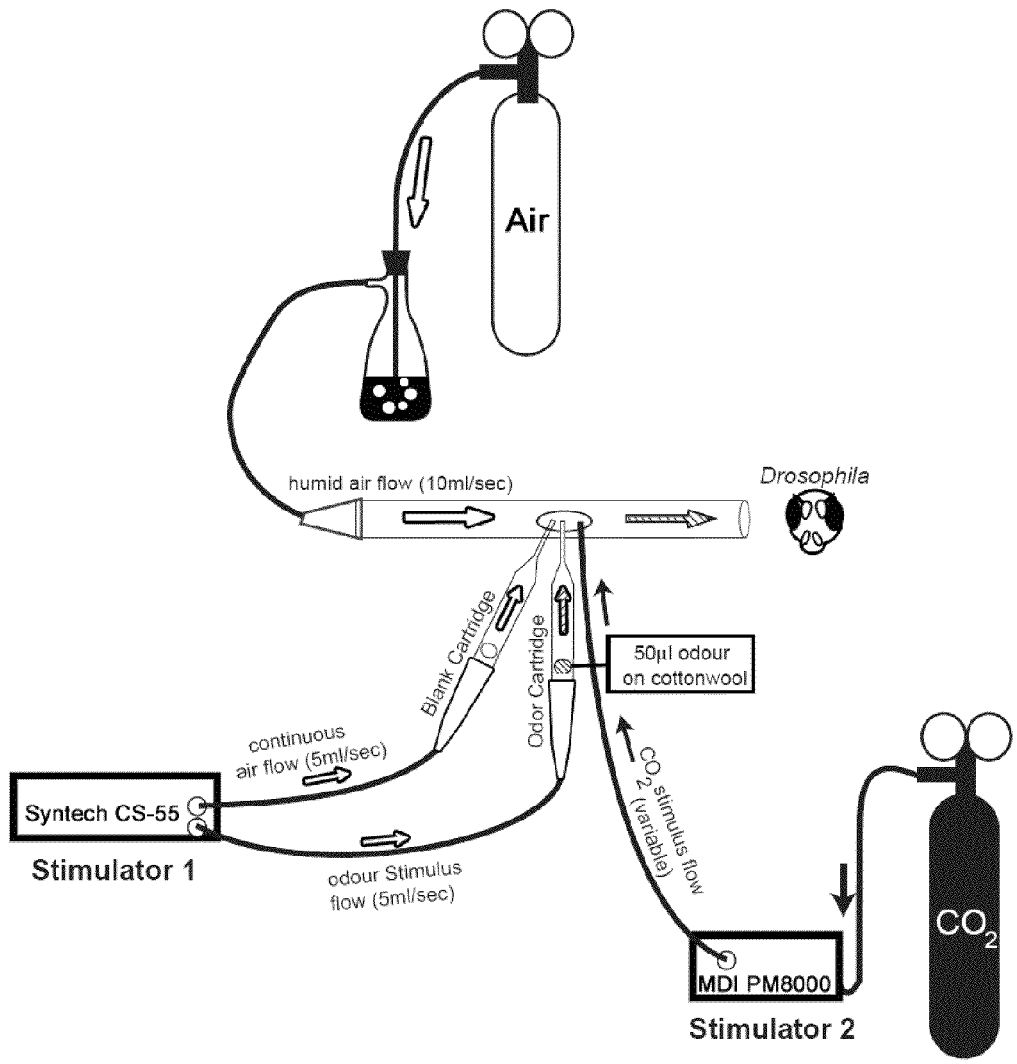

FIG. 16 is a schematic diagram of an odour-delivery system to maintain steady concentration of $CO_2$ in binary mixture experiments. Cartridges were made from Pasteur pipettes with pre-filled cotton wool inserts. 50 ml odorant dissolved in paraffin oil (at specific concentrations) was applied to the cotton wool, and a 1.5 ml disposable tip attached to the open end to make the "odour cartridge". A controlled "humidified air flow" was generated from a compressed air cylinder by bubbling through water, and passed through a glass tube, and released over the recording arena holding the *Drosophila*. A C-55 stimulus controller (Syntech) was used to generate an additional activated-charcoal filtered continuous air flow of 5 ml/sec which was delivered into the humidified airstream through a "blank cartridge" with the tip placed through a hole in the tube. To generate controlled odourant stimulus the C-55 stimulus controller was used to switch air flow from the "continuous air flow" to "odor stimulus flow" channel. An additional $CO_2$ stimulus was pulsed through a separate system that delivered controlled pulses (variable 2.5 ml/sec-6.5 ml/sec) into the same humidified airstream, from either a 1%, 5% or 100% cylinder of $CO_2$ (Airgas).

Figure 17:
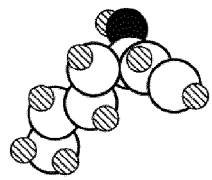
Figure 17:
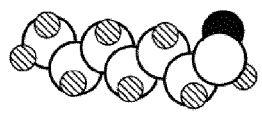
Figure 17:
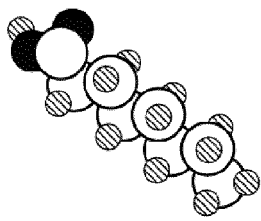
Figure 17:
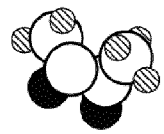
Figure 17:
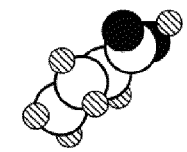
Figure 17:
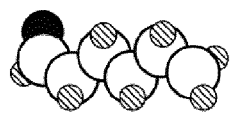
Figure 17:
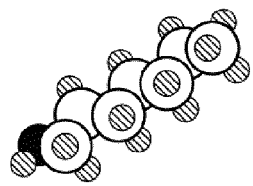
Figure 17:
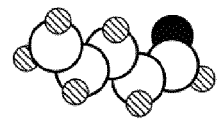
Figure 17:
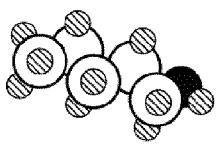
Figure 17:
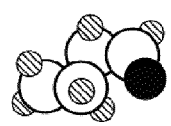
Figure 17:
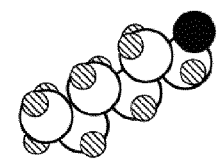
Figure 17:
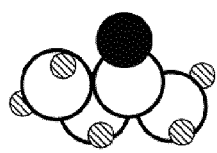

FIG. 17 shows space filling 3-D models of 12 ligands of the $CO_2$ receptor (butanone is activator).

DETAILED DESCRIPTION

As used herein and in the appended claims, the singular forms "a," "and," and "the" include plural referents unless the context clearly dictates otherwise. Thus, for example, reference to "an insect" includes a plurality of such insects and reference to "the compound" includes reference to one or more compounds, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The disclosure provides a class of volatile odorants that can inhibit the electrophysiological response of the $CO_2$ neuron in various insect disease vectors including *Drosophila melanogaster, Culex quinquefasciatus, An. gambiae* and *Aedes aegypti* mosquitoes. In some embodiment, the odorants can completely inhibit the electrophysiological response of the $CO_2$ neuron at very low concentrations.

The odorants of the disclosure provide new and useful compositions for insect repellents, masking agents and traps. The class of compound described and identified by the method of the disclosure include volatile odorants that can mask or repel Anopheles at low concentrations and can be easily dispersed in the air and have the potential to protect several individuals within a large area. Traditional repellents like DEET, or its derivatives, have low volatility and need to be applied on the skin or to garments at much higher concentrations. Furthermore, the odorants of the disclosure which can spread over large areas may be adopted more easily in developing countries due to ease of delivery. The compounds of the disclosure are useful in small quantities, can be delivered in multiple forms like vapors and lotions, are economical, environmentally friendly, and are present in natural sources.

Based upon the data and chemical odorants identified herein, additional odorants can be identified using the structural information of the odorants, in silico modeling and screening and biological assays.

Host-odor cues, among others, are detected by olfactory receptor neurons (ORNs) that are present on the surface of at least two types of olfactory organs, the antennae and the maxillary palps. The antenna is the main olfactory organ and its surface is covered by hundreds of sensilla, each of which is innervated by the dendrites of 1-5 ORNs. Odor molecules pass through pores on the surface of sensilla and activate odor receptor proteins present on the dendritic membranes of the ORNs.

The odor receptor (Or) gene family in insects was first identified in *D. melanogaster*. It comprises a highly divergent family of 60 Odor receptor (Or) genes that encode proteins predicted to contain seven trans-membrane regions.

One of the most important host-seeking cues for hematophagous insects is $CO_2$. The $CO_2$ receptor was first identified in *D. melanogaster*. This receptor comprises two proteins, Gr21a and Gr63a, which are encoded by two members of a large Gustatory receptor (Gr) gene family that is distantly related in sequence to the Or genes. Both Gr21a and Gr63a are extremely well conserved in sequence across several insect species. Orthologs for both Gr21a and Gr63a have been identified in *An. gambiae* and *Ae. aegypti*. Moreover, both mosquitoes possess a third gene that is closely related to Gr21a. The three *An. gambiae* homologs AgGr22, AgGr23 and AgGr24 are co-expressed in ORNs of the maxillary palp. Functional expression studies in *Drosophila* has demonstrated that they are $CO_2$ receptors as well.

Odor responses of ORNs on the surface of the antennae and maxillary palps have been studied using two separate techniques. Whole organ recordings called electroantennograms (EAGs) and electropalpograms (EPGs) have been used to detect the aggregate electrical activities from a large number of neurons in response to odors. A more sensitive and exact method has also been used to examine the functional properties of olfactory neurons within a single sensillum, and neurons that respond to behaviourally important ligands such as $CO_2$, ammonia, phenols, 1-octen-3-ol, lactic acid, and carboxylic acids have been identified.

Because mosquitoes rely on their sense of smell to identify human odors, olfactory system function is a prime target to modify host-seeking behavior. The kairomone $CO_2$ is used as bait by several mosquito traps that are currently sold in the market. In some instances an additional odor, usually 1-octen-3-ol, is also included to increase the efficiency of mosquito catches. Identification of more potent attractant odors, or more efficacious odor blends are required to further improve the efficiency of these $CO_2$ traps. Development of cheap $CO_2$-free traps may be of particular importance since generating $CO_2$ in a trap is problematic.

In a complementary fashion, blocking of insect odor receptors may be effective in masking human hosts, or may even work as repellents. There has been a great interest to identify novel classes of volatile compounds that can block mosquito receptors that detect kairomones like $CO_2$.

Most blood feeding insects, including mosquitoes, sandflies, Testse flies, use olfactory cues to identify human hosts. This group of hematophagous insects can transmit a wide assortment of deadly human diseases that together cause more suffering and deaths globally than any other disease condition. Diseases transmitted by such insects include malaria, dengue fever, yellow fever, West Nile virus, filariasis, river blindness, epidemic polyarthritis, Leshmaniasis, trypanosomiasis, Japanese encephalitis, St. Louis Encephalitis amongst others.

When a female of the species obtains a blood meal from an infected human being, she ingests the disease agent which can now be carried by the insect. If the insect happens to take another blood meal from an uninfected individual the causative agent can be transferred through the saliva to the bloodstream of the uninfected human. The diseases discussed above causes both acute and chronic morbidity and mortality in humans. For humans that live in areas that do not have incidences of these deadly diseases, the bites of these insects pose a significant nuisance value.

Traditional vector control methods often involve the heavy use of chemical insecticides that are harmful to the environment and often to human health. Moreover, insects can develop resistance to these chemicals, suggesting that there is a need to identify novel ways of insect control that are effective, cheap, and environmentally friendly. Integrating methods that inhibit vector-human contact, such as vector control and the use of insect repellents, bednets, or traps, may play a complementary and critical role in controlling the spread of these deadly diseases.

In order to transmit disease, a vector insect needs to find and feed on at least two human beings, of which the first host must be infected. For most vector insects attraction to human hosts is mediated primarily by volatile cues that are detected by the olfactory system of the insect. Female vector insects are exquisitely sensitive to minute changes in carbon dioxide ($CO_2$) concentrations. For example, when a host-seeking female mosquito encounters a plume of $CO_2$ she orients upwind using optomotor anemotaxis. Moreover, recent studies have established that a single, transient (<100 ms) exposure to a filament of $CO_2$ instantly lowers the threshold of response to human skin odor in *Aedes aegypti* by a factor of at least ten, which suggests that perhaps $CO_2$ and not skin odor is in effect the long-distance attractant.

The disclosure provides a group of volatile chemicals that can be used to modify host-seeking behavior by disrupting the detection of $CO_2$ from, for example, human breath by dipteran insects including mosquitoes and fruit flies, and provides structures for identifying other odorants that can modify $CO_2$ response in these insects. More specifically, the disclosure provides structures of volatile chemicals that strongly inhibit or activate olfactory neurons that detect $CO_2$ in dipteran insects like mosquitoes and *Drosophila*, and can potentially modify $CO_2$ mediated insect behavior. The structural features of the inhibitory odorants provided can enable identification of additional structurally-related $CO_2$ response inhibitory odorants using assays described herein and structure activity relationships (SAR).

An antagonist refers to a compound the can reversibly or irreversibly inhibit that activity of a $CO_2$ sensing neuron or activates the $CO_2$ sensing neuron (i.e., an ORN) upon exposure to the compound such that the neuron ORN cannot properly signal upon a change in odor levels.

The compounds and compositions of the disclosure can be used as antagonist to mask the chemoattractant activity of $CO_2$. The compounds and compositions can be used as attractants alone or in combination with an insecticide, trap, or other mechanical, electrical or chemical that kills the insect or prevents its escape.

Compounds useful in the methods, compositions and devices of the disclosure include, but are not limited to, 4 to 6 carbon aldehydes (e.g., butanal, pentanal, hexanal), 5 to 8 carbon alcohols (e.g., pentanol, hexanol, cyclohexanol, Z-3-hexen-1-ol, Z-2-hexen-1-ol, 1-hexen-3-ol, 1-hepten-3-ol, 3-hexanol, 2-hexanol and the like), and 3 to 8 carbon mono- or di-ketones (e.g., butanedione (2,3-butanedione), pentanedione and the like). Additional related compounds having similar structure can be assayed using the methods described herein to determine if they have antagonistic effects or agonistic effects. For example, compounds having 2-8 carbon atoms and an aldehyde, ketone or alcohol can be assayed using electrophysiology measurement described herein.

Furthermore, based upon the compounds identified herein, a structure based search followed by biological assays may be performed to identified compounds having a desired effect on $CO_2$ receptors in various insects. Table 1, for example, provides structure-data file (SDF) information for 11 effective compounds of the disclosure. SDF files and generated 3-D structures (see FIG. 17) of 12 volatile ligands for the $CO_2$ receptor can be utilized to identify structurally related chemicals. These structurally related chemicals can be identified using 2 different approaches: (1) 3-D or 2-D structure matching can be performed computationally or visually using standard methods available as software packages or through online interfaces that are publicly available (e.g., Pubchem—Related Structure Search http:~~pubchem.ncbi.nlm.nih.gov; Chemmine, http:~~bioweb.ucr.edu/ChemMineV2/ (note: back-slashes have been replaced with "~" to avoid hyperlinks); and (2) A descriptor based approach (as described above, and other Descriptor approaches) can be used to identify compounds that are structurally similar to the 11 volatile ligands (agonists/antagonists) set forth, for example, in FIG. 17.

Structure-based clustering can be used to identify compounds useful in compositions of the disclosure. The algorithm can include linkage clustering to join compounds into similarity groups, where every member in a cluster shares with at least one other member a similarity value above a user-specified threshold.

The identified compounds can then be assayed to identify their biological activity using the electrophysiology measurements described below. For example, a compound can be contacted with a CO2 receptor neuron and changes in the electrical signal measured. Alternatively, the compounds may be screened in a *Drosophila* $CO_2$ avoidance chamber.

Using structural information of the compounds set forth in FIG. 17, the top ~400 compounds having a nearest Euclidian distance from the compounds were identified. For example, using available online software called Chemmine (http:~~bioweb.ucr.edu/ChemMineV2) and searching the Pubchem Substances database with the 11 compounds of FIG. 17, a list of compounds where identified. The list comprises the top 50 hits for each of the compounds followed by removal of redundant structures. The software Chemmine uses a method called "Atom-pair" distances in order to compute similarities between compounds.

Table 2 provides a list of compounds having such relatedness and the SMILES structure which can be used for modulating $CO_2$ receptor activity in insects. Such compounds can be further screened using electrophysiology assays described herein and may be further modified and formulated for application to a subject, material or in traps or release devices.

TABLE 1

Structure Data Files (SDF) for the 11 strongest CO2 receptor inhibitors we have identified. Information in the sdf file can be used to generate 3-dimensional shapes of these compounds.

1-hexanol

| 21 | 20 | 0 | 0 | 0 | 0 | 0 | 0 | 0999 | V2000 | | | | | | |
|---|---|---|---|---|---|---|---|---|---|---|---|---|---|---|---|
| 1.7833 | −1.3584 | 0.9178 | C | 0 | 0 | 0 | 0 | 0 | 0 | 0 | 0 | 0 | 0 | 0 | 0 |
| 1.1442 | −1.8866 | 2.1933 | C | 0 | 0 | 0 | 0 | 0 | 0 | 0 | 0 | 0 | 0 | 0 | 0 |
| −0.1230 | −1.1065 | 2.5457 | C | 0 | 0 | 0 | 0 | 0 | 0 | 0 | 0 | 0 | 0 | 0 | 0 |
| −0.7660 | −1.5523 | 3.8620 | C | 0 | 0 | 0 | 0 | 0 | 0 | 0 | 0 | 0 | 0 | 0 | 0 |
| −2.0456 | −0.7898 | 4.2020 | C | 0 | 0 | 0 | 0 | 0 | 0 | 0 | 0 | 0 | 0 | 0 | 0 |
| −2.6297 | −1.2442 | 5.5331 | C | 0 | 0 | 0 | 0 | 0 | 0 | 0 | 0 | 0 | 0 | 0 | 0 |
| −3.8211 | −0.5123 | 5.7858 | O | 0 | 0 | 0 | 0 | 0 | 0 | 0 | 0 | 0 | 0 | 0 | 0 |
| 1.0759 | −1.4224 | 0.0850 | H | 0 | 0 | 0 | 0 | 0 | 0 | 0 | 0 | 0 | 0 | 0 | 0 |
| 2.0797 | −0.3109 | 1.0323 | H | 0 | 0 | 0 | 0 | 0 | 0 | 0 | 0 | 0 | 0 | 0 | 0 |
| 2.6719 | −1.9406 | 0.6536 | H | 0 | 0 | 0 | 0 | 0 | 0 | 0 | 0 | 0 | 0 | 0 | 0 |
| 1.8672 | −1.8141 | 3.0137 | H | 0 | 0 | 0 | 0 | 0 | 0 | 0 | 0 | 0 | 0 | 0 | 0 |
| 0.9125 | −2.9479 | 2.0545 | H | 0 | 0 | 0 | 0 | 0 | 0 | 0 | 0 | 0 | 0 | 0 | 0 |
| −0.8521 | −1.1958 | 1.7312 | H | 0 | 0 | 0 | 0 | 0 | 0 | 0 | 0 | 0 | 0 | 0 | 0 |
| 0.1252 | −0.0410 | 2.6309 | H | 0 | 0 | 0 | 0 | 0 | 0 | 0 | 0 | 0 | 0 | 0 | 0 |
| −0.0356 | −1.4015 | 4.6668 | H | 0 | 0 | 0 | 0 | 0 | 0 | 0 | 0 | 0 | 0 | 0 | 0 |
| −0.9747 | −2.6284 | 3.8233 | H | 0 | 0 | 0 | 0 | 0 | 0 | 0 | 0 | 0 | 0 | 0 | 0 |
| −2.8003 | −0.9283 | 3.4193 | H | 0 | 0 | 0 | 0 | 0 | 0 | 0 | 0 | 0 | 0 | 0 | 0 |
| −1.8465 | 0.2883 | 4.2424 | H | 0 | 0 | 0 | 0 | 0 | 0 | 0 | 0 | 0 | 0 | 0 | 0 |
| −2.8747 | −2.3107 | 5.5080 | H | 0 | 0 | 0 | 0 | 0 | 0 | 0 | 0 | 0 | 0 | 0 | 0 |
| −1.9274 | −1.0587 | 6.3521 | H | 0 | 0 | 0 | 0 | 0 | 0 | 0 | 0 | 0 | 0 | 0 | 0 |
| −4.1667 | −0.8245 | 6.6378 | H | 0 | 0 | 0 | 0 | 0 | 0 | 0 | 0 | 0 | 0 | 0 | 0 |
| 1 | 2 | 1 | 0 | 0 | 0 | 0 | | | | | | | | | |
| 2 | 3 | 1 | 0 | 0 | 0 | 0 | | | | | | | | | |
| 3 | 4 | 1 | 0 | 0 | 0 | 0 | | | | | | | | | |
| 4 | 5 | 1 | 0 | 0 | 0 | 0 | | | | | | | | | |
| 5 | 6 | 1 | 0 | 0 | 0 | 0 | | | | | | | | | |
| 6 | 7 | 1 | 0 | 0 | 0 | 0 | | | | | | | | | |
| 1 | 8 | 1 | 0 | 0 | 0 | 0 | | | | | | | | | |
| 1 | 9 | 1 | 0 | 0 | 0 | 0 | | | | | | | | | |
| 1 | 10 | 1 | 0 | 0 | 0 | 0 | | | | | | | | | |
| 2 | 11 | 1 | 0 | 0 | 0 | 0 | | | | | | | | | |
| 2 | 12 | 1 | 0 | 0 | 0 | 0 | | | | | | | | | |
| 3 | 13 | 1 | 0 | 0 | 0 | 0 | | | | | | | | | |
| 3 | 14 | 1 | 0 | 0 | 0 | 0 | | | | | | | | | |
| 4 | 15 | 1 | 0 | 0 | 0 | 0 | | | | | | | | | |
| 4 | 16 | 1 | 0 | 0 | 0 | 0 | | | | | | | | | |
| 5 | 17 | 1 | 0 | 0 | 0 | 0 | | | | | | | | | |
| 5 | 18 | 1 | 0 | 0 | 0 | 0 | | | | | | | | | |
| 6 | 19 | 1 | 0 | 0 | 0 | 0 | | | | | | | | | |
| 6 | 20 | 1 | 0 | 0 | 0 | 0 | | | | | | | | | |
| 7 | 21 | 1 | 0 | 0 | 0 | 0 | | | | | | | | | |

2,3-butanedione

| 12 | 11 | 0 | 0 | 0 | 0 | 0 | 0 | 0999 | V2000 | | | | | | |
|---|---|---|---|---|---|---|---|---|---|---|---|---|---|---|---|
| −0.2002 | 0.7639 | −1.9751 | C | 0 | 0 | 0 | 0 | 0 | 0 | 0 | 0 | 0 | 0 | 0 | 0 |
| −0.6030 | 1.9215 | −2.8647 | C | 0 | 0 | 0 | 0 | 0 | 0 | 0 | 0 | 0 | 0 | 0 | 0 |
| −0.3265 | 0.9226 | −0.4895 | C | 0 | 0 | 0 | 0 | 0 | 0 | 0 | 0 | 0 | 0 | 0 | 0 |
| −2.0166 | 2.4172 | −2.8013 | C | 0 | 0 | 0 | 0 | 0 | 0 | 0 | 0 | 0 | 0 | 0 | 0 |

TABLE 1-continued

Structure Data Files (SDF) for the 11 strongest
CO2 receptor inhibitors we have identified. Information in the sdf
file can be used to generate 3-dimensional shapes of these compounds.

| | | | | | | | | | | | | | | | | |
|---|---|---|---|---|---|---|---|---|---|---|---|---|---|---|---|---|
| 0.2136 | −0.2539 | −2.5146 | O | 0 | 0 | 0 | 0 | 0 | 0 | 0 | 0 | 0 | 0 | 0 | 0 | 0 |
| 0.2510 | 2.4021 | −3.5981 | O | 0 | 0 | 0 | 0 | 0 | 0 | 0 | 0 | 0 | 0 | 0 | 0 | 0 |
| −1.3155 | 0.5967 | −0.1592 | H | 0 | 0 | 0 | 0 | 0 | 0 | 0 | 0 | 0 | 0 | 0 | 0 | 0 |
| −0.2085 | 1.9789 | −0.2291 | H | 0 | 0 | 0 | 0 | 0 | 0 | 0 | 0 | 0 | 0 | 0 | 0 | 0 |
| 0.4579 | 0.3556 | 0.0172 | H | 0 | 0 | 0 | 0 | 0 | 0 | 0 | 0 | 0 | 0 | 0 | 0 | 0 |
| −2.1065 | 3.2016 | −2.0463 | H | 0 | 0 | 0 | 0 | 0 | 0 | 0 | 0 | 0 | 0 | 0 | 0 | 0 |
| −2.2927 | 2.8413 | −3.7715 | H | 0 | 0 | 0 | 0 | 0 | 0 | 0 | 0 | 0 | 0 | 0 | 0 | 0 |
| −2.6960 | 1.5899 | −2.5834 | H | 0 | 0 | 0 | 0 | 0 | 0 | 0 | 0 | 0 | 0 | 0 | 0 | 0 |
| 1 | 2 | | 1 | | 0 | | 0 | | 0 | | 0 | | | | | |
| 1 | 3 | | 1 | | 0 | | 0 | | 0 | | 0 | | | | | |
| 1 | 5 | | 2 | | 0 | | 0 | | 0 | | 0 | | | | | |
| 2 | 4 | | 1 | | 0 | | 0 | | 0 | | 0 | | | | | |
| 2 | 6 | | 2 | | 0 | | 0 | | 0 | | 0 | | | | | |
| 3 | 7 | | 1 | | 0 | | 0 | | 0 | | 0 | | | | | |
| 3 | 8 | | 1 | | 0 | | 0 | | 0 | | 0 | | | | | |
| 3 | 9 | | 1 | | 0 | | 0 | | 0 | | 0 | | | | | |
| 4 | 10 | | 1 | | 0 | | 0 | | 0 | | 0 | | | | | |
| 4 | 11 | | 1 | | 0 | | 0 | | 0 | | 0 | | | | | |
| 4 | 12 | | 1 | | 0 | | 0 | | 0 | | 0 | | | | | | butanal

| | | | | | | | | | | | | | | | | |
|---|---|---|---|---|---|---|---|---|---|---|---|---|---|---|---|---|
| 13 | 12 | 0 | 0 | | 0 | | 0 | | 0 | | 0999 | | V2000 | | | |
| 2.7209 | 1.9254 | −2.5423 | C | 0 | 0 | 0 | 0 | 0 | 0 | 0 | 0 | 0 | 0 | 0 | 0 | 0 |
| −0.0377 | −0.3343 | −1.0417 | C | 0 | 0 | 0 | 0 | 0 | 0 | 0 | 0 | 0 | 0 | 0 | 0 | 0 |
| 2.0587 | 0.9330 | −1.6172 | C | 0 | 0 | 0 | 0 | 0 | 0 | 0 | 0 | 0 | 0 | 0 | 0 | 0 |
| 0.5947 | 0.6927 | −1.9665 | C | 0 | 0 | 0 | 0 | 0 | 0 | 0 | 0 | 0 | 0 | 0 | 0 | 0 |
| 2.1550 | 2.5135 | −3.4576 | O | 0 | 0 | 0 | 0 | 0 | 0 | 0 | 0 | 0 | 0 | 0 | 0 | 0 |
| 3.7919 | 2.1026 | −2.3432 | H | 0 | 0 | 0 | 0 | 0 | 0 | 0 | 0 | 0 | 0 | 0 | 0 | 0 |
| 0.5006 | −1.2864 | −1.0863 | H | 0 | 0 | 0 | 0 | 0 | 0 | 0 | 0 | 0 | 0 | 0 | 0 | 0 |
| −0.0133 | 0.0215 | −0.0070 | H | 0 | 0 | 0 | 0 | 0 | 0 | 0 | 0 | 0 | 0 | 0 | 0 | 0 |
| −1.0822 | −0.5167 | −1.3137 | H | 0 | 0 | 0 | 0 | 0 | 0 | 0 | 0 | 0 | 0 | 0 | 0 | 0 |
| 2.1501 | 1.3219 | −0.5973 | H | 0 | 0 | 0 | 0 | 0 | 0 | 0 | 0 | 0 | 0 | 0 | 0 | 0 |
| 2.6253 | −0.0025 | −1.6780 | H | 0 | 0 | 0 | 0 | 0 | 0 | 0 | 0 | 0 | 0 | 0 | 0 | 0 |
| 0.0348 | 1.6332 | −1.8999 | H | 0 | 0 | 0 | 0 | 0 | 0 | 0 | 0 | 0 | 0 | 0 | 0 | 0 |
| 0.5092 | 0.3471 | −3.0037 | H | 0 | 0 | 0 | 0 | 0 | 0 | 0 | 0 | 0 | 0 | 0 | 0 | 0 |
| 1 | 3 | | 1 | | 0 | | 0 | | 0 | | 0 | | | | | |
| 1 | 5 | | 2 | | 0 | | 0 | | 0 | | 0 | | | | | |
| 2 | 4 | | 1 | | 0 | | 0 | | 0 | | 0 | | | | | |
| 3 | 4 | | 1 | | 0 | | 0 | | 0 | | 0 | | | | | |
| 1 | 6 | | 1 | | 0 | | 0 | | 0 | | 0 | | | | | |
| 2 | 7 | | 1 | | 0 | | 0 | | 0 | | 0 | | | | | |
| 2 | 8 | | 1 | | 0 | | 0 | | 0 | | 0 | | | | | |
| 2 | 9 | | 1 | | 0 | | 0 | | 0 | | 0 | | | | | |
| 3 | 10 | | 1 | | 0 | | 0 | | 0 | | 0 | | | | | |
| 3 | 11 | | 1 | | 0 | | 0 | | 0 | | 0 | | | | | |
| 4 | 12 | | 1 | | 0 | | 0 | | 0 | | 0 | | | | | |
| 4 | 13 | | 1 | | 0 | | 0 | | 0 | | 0 | | | | | | pentanal

| | | | | | | | | | | | | | | | | |
|---|---|---|---|---|---|---|---|---|---|---|---|---|---|---|---|---|
| 16 | 15 | 0 | 0 | | 0 | | 0 | | 0 | | 0999 | | V2000 | | | |
| 3.9375 | −4.1331 | 1.7332 | C | 0 | 0 | 0 | 0 | 0 | 0 | 0 | 0 | 0 | 0 | 0 | 0 | 0 |
| 1.0280 | −0.2936 | 0.2373 | C | 0 | 0 | 0 | 0 | 0 | 0 | 0 | 0 | 0 | 0 | 0 | 0 | 0 |
| 2.5434 | −3.6685 | 1.3866 | C | 0 | 0 | 0 | 0 | 0 | 0 | 0 | 0 | 0 | 0 | 0 | 0 | 0 |
| 1.0766 | −1.7593 | 0.6390 | C | 0 | 0 | 0 | 0 | 0 | 0 | 0 | 0 | 0 | 0 | 0 | 0 | 0 |
| 2.4920 | −2.1884 | 1.0222 | C | 0 | 0 | 0 | 0 | 0 | 0 | 0 | 0 | 0 | 0 | 0 | 0 | 0 |
| 4.9391 | −3.4264 | 1.6979 | O | 0 | 0 | 0 | 0 | 0 | 0 | 0 | 0 | 0 | 0 | 0 | 0 | 0 |
| 4.0121 | −5.1919 | 2.0358 | H | 0 | 0 | 0 | 0 | 0 | 0 | 0 | 0 | 0 | 0 | 0 | 0 | 0 |
| 1.3865 | 0.3362 | 1.0575 | H | 0 | 0 | 0 | 0 | 0 | 0 | 0 | 0 | 0 | 0 | 0 | 0 | 0 |
| 0.0053 | 0.0132 | −0.0043 | H | 0 | 0 | 0 | 0 | 0 | 0 | 0 | 0 | 0 | 0 | 0 | 0 | 0 |
| 1.6595 | −0.1050 | −0.6369 | H | 0 | 0 | 0 | 0 | 0 | 0 | 0 | 0 | 0 | 0 | 0 | 0 | 0 |
| 2.1912 | −4.2811 | 0.5497 | H | 0 | 0 | 0 | 0 | 0 | 0 | 0 | 0 | 0 | 0 | 0 | 0 | 0 |
| 1.9039 | −3.8723 | 2.2521 | H | 0 | 0 | 0 | 0 | 0 | 0 | 0 | 0 | 0 | 0 | 0 | 0 | 0 |
| 0.7142 | −2.3725 | −0.1944 | H | 0 | 0 | 0 | 0 | 0 | 0 | 0 | 0 | 0 | 0 | 0 | 0 | 0 |
| 0.3962 | −1.9236 | 1.4827 | H | 0 | 0 | 0 | 0 | 0 | 0 | 0 | 0 | 0 | 0 | 0 | 0 | 0 |
| 2.8444 | −1.5867 | 1.8694 | H | 0 | 0 | 0 | 0 | 0 | 0 | 0 | 0 | 0 | 0 | 0 | 0 | 0 |
| 3.1774 | −1.9892 | 0.1887 | H | 0 | 0 | 0 | 0 | 0 | 0 | 0 | 0 | 0 | 0 | 0 | 0 | 0 |
| 1 | 3 | | 1 | | 0 | | 0 | | 0 | | 0 | | | | | |
| 1 | 6 | | 2 | | 0 | | 0 | | 0 | | 0 | | | | | |
| 2 | 4 | | 1 | | 0 | | 0 | | 0 | | 0 | | | | | |
| 3 | 5 | | 1 | | 0 | | 0 | | 0 | | 0 | | | | | |
| 4 | 5 | | 1 | | 0 | | 0 | | 0 | | 0 | | | | | |
| 1 | 7 | | 1 | | 0 | | 0 | | 0 | | 0 | | | | | |
| 2 | 8 | | 1 | | 0 | | 0 | | 0 | | 0 | | | | | |
| 2 | 9 | | 1 | | 0 | | 0 | | 0 | | 0 | | | | | |
| 2 | 10 | | 1 | | 0 | | 0 | | 0 | | 0 | | | | | |
| 3 | 11 | | 1 | | 0 | | 0 | | 0 | | 0 | | | | | |

TABLE 1-continued

Structure Data Files (SDF) for the 11 strongest
CO2 receptor inhibitors we have identified. Information in the sdf
file can be used to generate 3-dimensional shapes of these compounds.

| | | | | | | | |
|---|---|---|---|---|---|---|---|
| 3 | 12 | 1 | 0 | 0 | 0 | 0 | |
| 4 | 13 | 1 | 0 | 0 | 0 | 0 | |
| 4 | 14 | 1 | 0 | 0 | 0 | 0 | |
| 5 | 15 | 1 | 0 | 0 | 0 | 0 | |
| 5 | 16 | 1 | 0 | 0 | 0 | 0 | | hexanal

| 19 | 18 | 0 | 0 | 0 | 0 | 0 | 0 | 0999 | V2000 | | | | |
|---|---|---|---|---|---|---|---|---|---|---|---|---|---|
| 1.0801 | 2.1730 | −6.8042 | C | 0 | 0 | 0 | 0 | 0 | 0 | 0 | 0 | 0 | 0 |
| −0.1636 | −0.2887 | −1.0437 | C | 0 | 0 | 0 | 0 | 0 | 0 | 0 | 0 | 0 | 0 |
| 0.5536 | 1.1252 | −5.8514 | C | 0 | 0 | 0 | 0 | 0 | 0 | 0 | 0 | 0 | 0 |
| 0.4168 | 0.7620 | −1.9768 | C | 0 | 0 | 0 | 0 | 0 | 0 | 0 | 0 | 0 | 0 |
| 0.7706 | 1.4609 | −4.3783 | C | 0 | 0 | 0 | 0 | 0 | 0 | 0 | 0 | 0 | 0 |
| 0.1592 | 0.4130 | −3.4430 | C | 0 | 0 | 0 | 0 | 0 | 0 | 0 | 0 | 0 | 0 |
| 1.6925 | 3.1814 | −6.4704 | O | 0 | 0 | 0 | 0 | 0 | 0 | 0 | 0 | 0 | 0 |
| 0.8557 | 1.9852 | −7.8686 | H | 0 | 0 | 0 | 0 | 0 | 0 | 0 | 0 | 0 | 0 |
| −1.2413 | −0.3870 | −1.2070 | H | 0 | 0 | 0 | 0 | 0 | 0 | 0 | 0 | 0 | 0 |
| −0.0022 | −0.0149 | 0.0039 | H | 0 | 0 | 0 | 0 | 0 | 0 | 0 | 0 | 0 | 0 |
| 0.2969 | −1.2663 | −1.2186 | H | 0 | 0 | 0 | 0 | 0 | 0 | 0 | 0 | 0 | 0 |
| 1.0227 | 0.1687 | −6.1049 | H | 0 | 0 | 0 | 0 | 0 | 0 | 0 | 0 | 0 | 0 |
| −0.5202 | 1.0343 | −6.0496 | H | 0 | 0 | 0 | 0 | 0 | 0 | 0 | 0 | 0 | 0 |
| 1.4951 | 0.8453 | −1.7980 | H | 0 | 0 | 0 | 0 | 0 | 0 | 0 | 0 | 0 | 0 |
| −0.0275 | 1.7361 | −1.7417 | H | 0 | 0 | 0 | 0 | 0 | 0 | 0 | 0 | 0 | 0 |
| 1.8412 | 1.5700 | −4.1670 | H | 0 | 0 | 0 | 0 | 0 | 0 | 0 | 0 | 0 | 0 |
| 0.3039 | 2.4319 | −4.1720 | H | 0 | 0 | 0 | 0 | 0 | 0 | 0 | 0 | 0 | 0 |
| −0.9215 | 0.3508 | −3.6200 | H | 0 | 0 | 0 | 0 | 0 | 0 | 0 | 0 | 0 | 0 |
| 0.5775 | −0.5766 | −3.6596 | H | 0 | 0 | 0 | 0 | 0 | 0 | 0 | 0 | 0 | 0 |
| 1 | 3 | 1 | 0 | 0 | 0 | 0 | | | | | | | |
| 1 | 7 | 2 | 0 | 0 | 0 | 0 | | | | | | | |
| 2 | 4 | 1 | 0 | 0 | 0 | 0 | | | | | | | |
| 3 | 5 | 1 | 0 | 0 | 0 | 0 | | | | | | | |
| 4 | 6 | 1 | 0 | 0 | 0 | 0 | | | | | | | |
| 5 | 6 | 1 | 0 | 0 | 0 | 0 | | | | | | | |
| 1 | 8 | 1 | 0 | 0 | 0 | 0 | | | | | | | |
| 2 | 9 | 1 | 0 | 0 | 0 | 0 | | | | | | | |
| 2 | 10 | 1 | 0 | 0 | 0 | 0 | | | | | | | |
| 2 | 11 | 1 | 0 | 0 | 0 | 0 | | | | | | | |
| 3 | 12 | 1 | 0 | 0 | 0 | 0 | | | | | | | |
| 3 | 13 | 1 | 0 | 0 | 0 | 0 | | | | | | | |
| 4 | 14 | 1 | 0 | 0 | 0 | 0 | | | | | | | |
| 4 | 15 | 1 | 0 | 0 | 0 | 0 | | | | | | | |
| 5 | 16 | 1 | 0 | 0 | 0 | 0 | | | | | | | |
| 5 | 17 | 1 | 0 | 0 | 0 | 0 | | | | | | | |
| 6 | 18 | 1 | 0 | 0 | 0 | 0 | | | | | | | |
| 6 | 19 | 1 | 0 | 0 | 0 | 0 | | | | | | | | heptanol

| 24 | 23 | 0 | 0 | 0 | 0 | 0 | 0 | 0999 | V2000 | | | | |
|---|---|---|---|---|---|---|---|---|---|---|---|---|---|
| 2.0122 | −2.5402 | −0.1882 | C | 0 | 0 | 0 | 0 | 0 | 0 | 0 | 0 | 0 | 0 |
| 1.5978 | −2.9985 | −1.5783 | C | 0 | 0 | 0 | 0 | 0 | 0 | 0 | 0 | 0 | 0 |
| 0.0762 | −3.0068 | −1.7315 | C | 0 | 0 | 0 | 0 | 0 | 0 | 0 | 0 | 0 | 0 |
| −0.3960 | −3.5293 | −3.0913 | C | 0 | 0 | 0 | 0 | 0 | 0 | 0 | 0 | 0 | 0 |
| −1.9190 | −3.6070 | −3.2176 | C | 0 | 0 | 0 | 0 | 0 | 0 | 0 | 0 | 0 | 0 |
| −2.3336 | −4.1556 | −4.5822 | C | 0 | 0 | 0 | 0 | 0 | 0 | 0 | 0 | 0 | 0 |
| −3.8475 | −4.1981 | −4.7344 | C | 0 | 0 | 0 | 0 | 0 | 0 | 0 | 0 | 0 | 0 |
| −4.1654 | −4.7016 | −6.0245 | O | 0 | 0 | 0 | 0 | 0 | 0 | 0 | 0 | 0 | 0 |
| 1.6290 | −1.5370 | 0.0245 | H | 0 | 0 | 0 | 0 | 0 | 0 | 0 | 0 | 0 | 0 |
| 3.1034 | −2.5114 | −0.1085 | H | 0 | 0 | 0 | 0 | 0 | 0 | 0 | 0 | 0 | 0 |
| 1.6340 | −3.2231 | 0.5793 | H | 0 | 0 | 0 | 0 | 0 | 0 | 0 | 0 | 0 | 0 |
| 1.9965 | −4.0034 | −1.7589 | H | 0 | 0 | 0 | 0 | 0 | 0 | 0 | 0 | 0 | 0 |
| 2.0517 | −2.3292 | −2.3167 | H | 0 | 0 | 0 | 0 | 0 | 0 | 0 | 0 | 0 | 0 |
| −0.3183 | −1.9963 | −1.5687 | H | 0 | 0 | 0 | 0 | 0 | 0 | 0 | 0 | 0 | 0 |
| −0.3586 | −3.6441 | −0.9513 | H | 0 | 0 | 0 | 0 | 0 | 0 | 0 | 0 | 0 | 0 |
| 0.0104 | −2.8967 | −3.8898 | H | 0 | 0 | 0 | 0 | 0 | 0 | 0 | 0 | 0 | 0 |
| 0.0265 | −4.5313 | −3.2368 | H | 0 | 0 | 0 | 0 | 0 | 0 | 0 | 0 | 0 | 0 |
| −2.3586 | −2.6124 | −3.0838 | H | 0 | 0 | 0 | 0 | 0 | 0 | 0 | 0 | 0 | 0 |
| −2.3215 | −4.2506 | −2.4260 | H | 0 | 0 | 0 | 0 | 0 | 0 | 0 | 0 | 0 | 0 |
| −1.9265 | −5.1643 | −4.7263 | H | 0 | 0 | 0 | 0 | 0 | 0 | 0 | 0 | 0 | 0 |
| −1.9049 | −3.5418 | −5.3843 | H | 0 | 0 | 0 | 0 | 0 | 0 | 0 | 0 | 0 | 0 |
| −4.2785 | −3.1968 | −4.6355 | H | 0 | 0 | 0 | 0 | 0 | 0 | 0 | 0 | 0 | 0 |
| −4.2970 | −4.8556 | −3.9835 | H | 0 | 0 | 0 | 0 | 0 | 0 | 0 | 0 | 0 | 0 |
| −5.1341 | −4.7159 | −6.0891 | H | 0 | 0 | 0 | 0 | 0 | 0 | 0 | 0 | 0 | 0 |
| 1 | 2 | 1 | 0 | 0 | 0 | 0 | | | | | | | |
| 2 | 3 | 1 | 0 | 0 | 0 | 0 | | | | | | | |
| 3 | 4 | 1 | 0 | 0 | 0 | 0 | | | | | | | |
| 4 | 5 | 1 | 0 | 0 | 0 | 0 | | | | | | | |

TABLE 1-continued

Structure Data Files (SDF) for the 11 strongest CO2 receptor inhibitors we have identified. Information in the sdf file can be used to generate 3-dimensional shapes of these compounds.

| | | | | | | | |
|---|---|---|---|---|---|---|---|
| 5 | 6 | 1 | 0 | 0 | 0 | 0 | 0 |
| 6 | 7 | 1 | 0 | 0 | 0 | 0 | 0 |
| 7 | 8 | 1 | 0 | 0 | 0 | 0 | 0 |
| 1 | 9 | 1 | 0 | 0 | 0 | 0 | 0 |
| 1 | 10 | 1 | 0 | 0 | 0 | 0 | 0 |
| 1 | 11 | 1 | 0 | 0 | 0 | 0 | 0 |
| 2 | 12 | 1 | 0 | 0 | 0 | 0 | 0 |
| 2 | 13 | 1 | 0 | 0 | 0 | 0 | 0 |
| 3 | 14 | 1 | 0 | 0 | 0 | 0 | 0 |
| 3 | 15 | 1 | 0 | 0 | 0 | 0 | 0 |
| 4 | 16 | 1 | 0 | 0 | 0 | 0 | 0 |
| 4 | 17 | 1 | 0 | 0 | 0 | 0 | 0 |
| 5 | 18 | 1 | 0 | 0 | 0 | 0 | 0 |
| 5 | 19 | 1 | 0 | 0 | 0 | 0 | 0 |
| 6 | 20 | 1 | 0 | 0 | 0 | 0 | 0 |
| 6 | 21 | 1 | 0 | 0 | 0 | 0 | 0 |
| 7 | 22 | 1 | 0 | 0 | 0 | 0 | 0 |
| 7 | 23 | 1 | 0 | 0 | 0 | 0 | 0 |
| 8 | 24 | 1 | 0 | 0 | 0 | 0 | 0 | heptanal

| 22 | 21 | 0 | 0 | 0 | 0 | 0 | 0 | 0999 | V2000 | | | | | |
|---|---|---|---|---|---|---|---|---|---|---|---|---|---|---|
| 8.3266 | −1.0702 | 1.1188 | C | 0 | 0 | 0 | 0 | 0 | 0 | 0 | 0 | 0 | 0 | 0 |
| 0.8210 | −0.4475 | 0.5682 | C | 0 | 0 | 0 | 0 | 0 | 0 | 0 | 0 | 0 | 0 | 0 |
| 7.1932 | −0.4726 | 0.3268 | C | 0 | 0 | 0 | 0 | 0 | 0 | 0 | 0 | 0 | 0 | 0 |
| 2.1593 | −0.0291 | −0.0196 | C | 0 | 0 | 0 | 0 | 0 | 0 | 0 | 0 | 0 | 0 | 0 |
| 5.8388 | −0.8769 | 0.9008 | C | 0 | 0 | 0 | 0 | 0 | 0 | 0 | 0 | 0 | 0 | 0 |
| 3.3262 | −0.6628 | 0.7374 | C | 0 | 0 | 0 | 0 | 0 | 0 | 0 | 0 | 0 | 0 | 0 |
| 4.6698 | −0.2658 | 0.1224 | C | 0 | 0 | 0 | 0 | 0 | 0 | 0 | 0 | 0 | 0 | 0 |
| 8.1594 | −1.7410 | 2.1325 | O | 0 | 0 | 0 | 0 | 0 | 0 | 0 | 0 | 0 | 0 | 0 |
| 9.3427 | −0.8342 | 0.7592 | H | 0 | 0 | 0 | 0 | 0 | 0 | 0 | 0 | 0 | 0 | 0 |
| 0.7193 | −1.5370 | 0.5418 | H | 0 | 0 | 0 | 0 | 0 | 0 | 0 | 0 | 0 | 0 | 0 |
| −0.0089 | −0.0152 | 0.0004 | H | 0 | 0 | 0 | 0 | 0 | 0 | 0 | 0 | 0 | 0 | 0 |
| 0.7311 | −0.1231 | 1.6096 | H | 0 | 0 | 0 | 0 | 0 | 0 | 0 | 0 | 0 | 0 | 0 |
| 7.3019 | 0.6166 | 0.3015 | H | 0 | 0 | 0 | 0 | 0 | 0 | 0 | 0 | 0 | 0 | 0 |
| 7.2854 | −0.8466 | −0.6985 | H | 0 | 0 | 0 | 0 | 0 | 0 | 0 | 0 | 0 | 0 | 0 |
| 2.2417 | 1.0634 | 0.0159 | H | 0 | 0 | 0 | 0 | 0 | 0 | 0 | 0 | 0 | 0 | 0 |
| 2.1964 | −0.3232 | −1.0749 | H | 0 | 0 | 0 | 0 | 0 | 0 | 0 | 0 | 0 | 0 | 0 |
| 5.7585 | −1.9703 | 0.8688 | H | 0 | 0 | 0 | 0 | 0 | 0 | 0 | 0 | 0 | 0 | 0 |
| 5.7735 | −0.5797 | 1.9547 | H | 0 | 0 | 0 | 0 | 0 | 0 | 0 | 0 | 0 | 0 | 0 |
| 3.2962 | −0.3491 | 1.7880 | H | 0 | 0 | 0 | 0 | 0 | 0 | 0 | 0 | 0 | 0 | 0 |
| 3.2235 | −1.7548 | 0.7231 | H | 0 | 0 | 0 | 0 | 0 | 0 | 0 | 0 | 0 | 0 | 0 |
| 4.7087 | −0.6012 | −0.9212 | H | 0 | 0 | 0 | 0 | 0 | 0 | 0 | 0 | 0 | 0 | 0 |
| 4.7568 | 0.8272 | 0.1145 | H | 0 | 0 | 0 | 0 | 0 | 0 | 0 | 0 | 0 | 0 | 0 |
| 1 | 3 | 1 | 0 | 0 | 0 | 0 | | | | | | | | |
| 1 | 8 | 2 | 0 | 0 | 0 | 0 | | | | | | | | |
| 2 | 4 | 1 | 0 | 0 | 0 | 0 | | | | | | | | |
| 3 | 5 | 1 | 0 | 0 | 0 | 0 | | | | | | | | |
| 4 | 6 | 1 | 0 | 0 | 0 | 0 | | | | | | | | |
| 5 | 7 | 1 | 0 | 0 | 0 | 0 | | | | | | | | |
| 6 | 7 | 1 | 0 | 0 | 0 | 0 | | | | | | | | |
| 1 | 9 | 1 | 0 | 0 | 0 | 0 | | | | | | | | |
| 2 | 10 | 1 | 0 | 0 | 0 | 0 | | | | | | | | |
| 2 | 11 | 1 | 0 | 0 | 0 | 0 | | | | | | | | |
| 2 | 12 | 1 | 0 | 0 | 0 | 0 | | | | | | | | |
| 3 | 13 | 1 | 0 | 0 | 0 | 0 | | | | | | | | |
| 3 | 14 | 1 | 0 | 0 | 0 | 0 | | | | | | | | |
| 4 | 15 | 1 | 0 | 0 | 0 | 0 | | | | | | | | |
| 4 | 16 | 1 | 0 | 0 | 0 | 0 | | | | | | | | |
| 5 | 17 | 1 | 0 | 0 | 0 | 0 | | | | | | | | |
| 5 | 18 | 1 | 0 | 0 | 0 | 0 | | | | | | | | |
| 6 | 19 | 1 | 0 | 0 | 0 | 0 | | | | | | | | |
| 6 | 20 | 1 | 0 | 0 | 0 | 0 | | | | | | | | |
| 7 | 21 | 1 | 0 | 0 | 0 | 0 | | | | | | | | |
| 7 | 22 | 1 | 0 | 0 | 0 | 0 | | | | | | | | | pentanol

| 18 | 17 | 0 | 0 | 0 | 0 | 0 | 0 | 0999 | V2000 | | | | | |
|---|---|---|---|---|---|---|---|---|---|---|---|---|---|---|
| 0.8186 | −0.3802 | 0.6691 | C | 0 | 0 | 0 | 0 | 0 | 0 | 0 | 0 | 0 | 0 | 0 |
| 1.6185 | −1.4417 | −0.0691 | C | 0 | 0 | 0 | 0 | 0 | 0 | 0 | 0 | 0 | 0 | 0 |
| 2.2938 | −0.8687 | −1.3148 | C | 0 | 0 | 0 | 0 | 0 | 0 | 0 | 0 | 0 | 0 | 0 |
| 3.1237 | −1.9294 | −2.0346 | C | 0 | 0 | 0 | 0 | 0 | 0 | 0 | 0 | 0 | 0 | 0 |
| 3.8336 | −1.3564 | −3.2530 | C | 0 | 0 | 0 | 0 | 0 | 0 | 0 | 0 | 0 | 0 | 0 |
| 4.5965 | −2.3862 | −3.8665 | O | 0 | 0 | 0 | 0 | 0 | 0 | 0 | 0 | 0 | 0 | 0 |
| 1.4582 | 0.4571 | 0.9663 | H | 0 | 0 | 0 | 0 | 0 | 0 | 0 | 0 | 0 | 0 | 0 |
| 0.0111 | 0.0099 | 0.0414 | H | 0 | 0 | 0 | 0 | 0 | 0 | 0 | 0 | 0 | 0 | 0 |

TABLE 1-continued

Structure Data Files (SDF) for the 11 strongest CO2 receptor inhibitors we have identified. Information in the sdf file can be used to generate 3-dimensional shapes of these compounds.

| | | | | | | | | | | | | | | | | |
|---|---|---|---|---|---|---|---|---|---|---|---|---|---|---|---|---|
| 0.3713 | −0.8036 | 1.5739 | H | 0 | 0 | 0 | 0 | 0 | 0 | 0 | 0 | 0 | 0 | 0 | 0 | 0 |
| 0.9505 | −2.2636 | −0.3519 | H | 0 | 0 | 0 | 0 | 0 | 0 | 0 | 0 | 0 | 0 | 0 | 0 | 0 |
| 2.3753 | −1.8563 | 0.6070 | H | 0 | 0 | 0 | 0 | 0 | 0 | 0 | 0 | 0 | 0 | 0 | 0 | 0 |
| 1.5317 | −0.4729 | −1.9971 | H | 0 | 0 | 0 | 0 | 0 | 0 | 0 | 0 | 0 | 0 | 0 | 0 | 0 |
| 2.9390 | −0.0288 | −1.0292 | H | 0 | 0 | 0 | 0 | 0 | 0 | 0 | 0 | 0 | 0 | 0 | 0 | 0 |
| 2.4843 | −2.7645 | −2.3467 | H | 0 | 0 | 0 | 0 | 0 | 0 | 0 | 0 | 0 | 0 | 0 | 0 | 0 |
| 3.8659 | −2.3597 | −1.3509 | H | 0 | 0 | 0 | 0 | 0 | 0 | 0 | 0 | 0 | 0 | 0 | 0 | 0 |
| 4.5106 | −0.5456 | −2.9657 | H | 0 | 0 | 0 | 0 | 0 | 0 | 0 | 0 | 0 | 0 | 0 | 0 | 0 |
| 3.1116 | −0.9763 | −3.9827 | H | 0 | 0 | 0 | 0 | 0 | 0 | 0 | 0 | 0 | 0 | 0 | 0 | 0 |
| 5.0348 | −1.9896 | −4.6369 | H | 0 | 0 | 0 | 0 | 0 | 0 | 0 | 0 | 0 | 0 | 0 | 0 | 0 |
| 1 | 2 | | 1 | | 0 | | 0 | | 0 | | 0 | | | | | |
| 2 | 3 | | 1 | | 0 | | 0 | | 0 | | 0 | | | | | |
| 3 | 4 | | 1 | | 0 | | 0 | | 0 | | 0 | | | | | |
| 4 | 5 | | 1 | | 0 | | 0 | | 0 | | 0 | | | | | |
| 5 | 6 | | 1 | | 0 | | 0 | | 0 | | 0 | | | | | |
| 1 | 7 | | 1 | | 0 | | 0 | | 0 | | 0 | | | | | |
| 1 | 8 | | 1 | | 0 | | 0 | | 0 | | 0 | | | | | |
| 1 | 9 | | 1 | | 0 | | 0 | | 0 | | 0 | | | | | |
| 2 | 10 | | 1 | | 0 | | 0 | | 0 | | 0 | | | | | |
| 2 | 11 | | 1 | | 0 | | 0 | | 0 | | 0 | | | | | |
| 3 | 12 | | 1 | | 0 | | 0 | | 0 | | 0 | | | | | |
| 3 | 13 | | 1 | | 0 | | 0 | | 0 | | 0 | | | | | |
| 4 | 14 | | 1 | | 0 | | 0 | | 0 | | 0 | | | | | |
| 4 | 15 | | 1 | | 0 | | 0 | | 0 | | 0 | | | | | |
| 5 | 16 | | 1 | | 0 | | 0 | | 0 | | 0 | | | | | |
| 5 | 17 | | 1 | | 0 | | 0 | | 0 | | 0 | | | | | |
| 6 | 18 | | 1 | | 0 | | 0 | | 0 | | 0 | | | | | |

Heptanol

| | | | | | | | | | | | | | | | | |
|---|---|---|---|---|---|---|---|---|---|---|---|---|---|---|---|---|
| 24 | 23 | 0 | 0 | | 0 | | 0 | | 0 | | 0999 | | V2000 | | | |
| 2.0122 | −2.5402 | −0.1882 | C | 0 | 0 | 0 | 0 | 0 | 0 | 0 | 0 | 0 | 0 | 0 | 0 | 0 |
| 1.5978 | −2.9985 | −1.5783 | C | 0 | 0 | 0 | 0 | 0 | 0 | 0 | 0 | 0 | 0 | 0 | 0 | 0 |
| 0.0762 | −3.0068 | −1.7315 | C | 0 | 0 | 0 | 0 | 0 | 0 | 0 | 0 | 0 | 0 | 0 | 0 | 0 |
| −0.3960 | −3.5293 | −3.0913 | C | 0 | 0 | 0 | 0 | 0 | 0 | 0 | 0 | 0 | 0 | 0 | 0 | 0 |
| −1.9190 | −3.6070 | −3.2176 | C | 0 | 0 | 0 | 0 | 0 | 0 | 0 | 0 | 0 | 0 | 0 | 0 | 0 |
| −2.3336 | −4.1556 | −4.5822 | C | 0 | 0 | 0 | 0 | 0 | 0 | 0 | 0 | 0 | 0 | 0 | 0 | 0 |
| −3.8475 | −4.1981 | −4.7344 | C | 0 | 0 | 0 | 0 | 0 | 0 | 0 | 0 | 0 | 0 | 0 | 0 | 0 |
| −4.1654 | −4.7016 | −6.0245 | O | 0 | 0 | 0 | 0 | 0 | 0 | 0 | 0 | 0 | 0 | 0 | 0 | 0 |
| 1.6290 | −1.5370 | 0.0245 | H | 0 | 0 | 0 | 0 | 0 | 0 | 0 | 0 | 0 | 0 | 0 | 0 | 0 |
| 3.1034 | −2.5114 | −0.1085 | H | 0 | 0 | 0 | 0 | 0 | 0 | 0 | 0 | 0 | 0 | 0 | 0 | 0 |
| 1.6340 | −3.2231 | 0.5793 | H | 0 | 0 | 0 | 0 | 0 | 0 | 0 | 0 | 0 | 0 | 0 | 0 | 0 |
| 1.9965 | −4.0034 | −1.7589 | H | 0 | 0 | 0 | 0 | 0 | 0 | 0 | 0 | 0 | 0 | 0 | 0 | 0 |
| 2.0517 | −2.3292 | −2.3167 | H | 0 | 0 | 0 | 0 | 0 | 0 | 0 | 0 | 0 | 0 | 0 | 0 | 0 |
| −0.3183 | −1.9963 | −1.5687 | H | 0 | 0 | 0 | 0 | 0 | 0 | 0 | 0 | 0 | 0 | 0 | 0 | 0 |
| −0.3586 | −3.6441 | −0.9513 | H | 0 | 0 | 0 | 0 | 0 | 0 | 0 | 0 | 0 | 0 | 0 | 0 | 0 |
| 0.0104 | −2.8967 | −3.8898 | H | 0 | 0 | 0 | 0 | 0 | 0 | 0 | 0 | 0 | 0 | 0 | 0 | 0 |
| 0.0265 | −4.5313 | −3.2368 | H | 0 | 0 | 0 | 0 | 0 | 0 | 0 | 0 | 0 | 0 | 0 | 0 | 0 |
| −2.3586 | −2.6124 | −3.0838 | H | 0 | 0 | 0 | 0 | 0 | 0 | 0 | 0 | 0 | 0 | 0 | 0 | 0 |
| −2.3215 | −4.2506 | −2.4260 | H | 0 | 0 | 0 | 0 | 0 | 0 | 0 | 0 | 0 | 0 | 0 | 0 | 0 |
| −1.9265 | −5.1643 | −4.7263 | H | 0 | 0 | 0 | 0 | 0 | 0 | 0 | 0 | 0 | 0 | 0 | 0 | 0 |
| −1.9049 | −3.5418 | −5.3843 | H | 0 | 0 | 0 | 0 | 0 | 0 | 0 | 0 | 0 | 0 | 0 | 0 | 0 |
| −4.2785 | −3.1968 | −4.6355 | H | 0 | 0 | 0 | 0 | 0 | 0 | 0 | 0 | 0 | 0 | 0 | 0 | 0 |
| −4.2970 | −4.8556 | −3.9835 | H | 0 | 0 | 0 | 0 | 0 | 0 | 0 | 0 | 0 | 0 | 0 | 0 | 0 |
| −5.1341 | −4.7159 | −6.0891 | H | 0 | 0 | 0 | 0 | 0 | 0 | 0 | 0 | 0 | 0 | 0 | 0 | 0 |
| 1 | 2 | | 1 | | 0 | | 0 | | 0 | | 0 | | | | | |
| 2 | 3 | | 1 | | 0 | | 0 | | 0 | | 0 | | | | | |
| 3 | 4 | | 1 | | 0 | | 0 | | 0 | | 0 | | | | | |
| 4 | 5 | | 1 | | 0 | | 0 | | 0 | | 0 | | | | | |
| 5 | 6 | | 1 | | 0 | | 0 | | 0 | | 0 | | | | | |
| 6 | 7 | | 1 | | 0 | | 0 | | 0 | | 0 | | | | | |
| 7 | 8 | | 1 | | 0 | | 0 | | 0 | | 0 | | | | | |
| 1 | 9 | | 1 | | 0 | | 0 | | 0 | | 0 | | | | | |
| 1 | 10 | | 1 | | 0 | | 0 | | 0 | | 0 | | | | | |
| 1 | 11 | | 1 | | 0 | | 0 | | 0 | | 0 | | | | | |
| 2 | 12 | | 1 | | 0 | | 0 | | 0 | | 0 | | | | | |
| 2 | 13 | | 1 | | 0 | | 0 | | 0 | | 0 | | | | | |
| 3 | 14 | | 1 | | 0 | | 0 | | 0 | | 0 | | | | | |
| 3 | 15 | | 1 | | 0 | | 0 | | 0 | | 0 | | | | | |
| 4 | 16 | | 1 | | 0 | | 0 | | 0 | | 0 | | | | | |
| 4 | 17 | | 1 | | 0 | | 0 | | 0 | | 0 | | | | | |
| 5 | 18 | | 1 | | 0 | | 0 | | 0 | | 0 | | | | | |
| 5 | 19 | | 1 | | 0 | | 0 | | 0 | | 0 | | | | | |
| 6 | 20 | | 1 | | 0 | | 0 | | 0 | | 0 | | | | | |
| 6 | 21 | | 1 | | 0 | | 0 | | 0 | | 0 | | | | | |

TABLE 1-continued

Structure Data Files (SDF) for the 11 strongest
CO2 receptor inhibitors we have identified. Information in the sdf
file can be used to generate 3-dimensional shapes of these compounds.

| | | | | | | | | | | | | | | | |
|---|---|---|---|---|---|---|---|---|---|---|---|---|---|---|---|
| 7 | 22 | 1 | 0 | 0 | 0 | 0 | | | | | | | | | |
| 7 | 23 | 1 | 0 | 0 | 0 | 0 | | | | | | | | | |
| 8 | 24 | 1 | 0 | 0 | 0 | 0 | | | | | | | | | | butyric acid

| | | | | | | | | | | | | | | | |
|---|---|---|---|---|---|---|---|---|---|---|---|---|---|---|---|
| 14 | 13 | 0 | 0 | 0 | 0 | 0 | 0 | 0999 | V2000 | | | | | | |
| 0.3282 | 0.2592 | 3.5153 | C | 0 | 0 | 0 | 0 | 0 | 0 | 0 | 0 | 0 | 0 | 0 | 0 |
| −1.2615 | −1.9835 | 0.7852 | C | 0 | 0 | 0 | 0 | 0 | 0 | 0 | 0 | 0 | 0 | 0 | 0 |
| −0.7524 | −0.3453 | 2.6537 | C | 0 | 0 | 0 | 0 | 0 | 0 | 0 | 0 | 0 | 0 | 0 | 0 |
| −0.1903 | −1.3680 | 1.6737 | C | 0 | 0 | 0 | 0 | 0 | 0 | 0 | 0 | 0 | 0 | 0 | 0 |
| 1.5220 | 0.0259 | 3.3744 | O | 0 | 0 | 0 | 0 | 0 | 0 | 0 | 0 | 0 | 0 | 0 | 0 |
| −0.1577 | 1.1129 | 4.4497 | O | 0 | 0 | 0 | 0 | 0 | 0 | 0 | 0 | 0 | 0 | 0 | 0 |
| −1.7779 | −1.2199 | 0.1955 | H | 0 | 0 | 0 | 0 | 0 | 0 | 0 | 0 | 0 | 0 | 0 | 0 |
| −2.0054 | −2.5207 | 1.3819 | H | 0 | 0 | 0 | 0 | 0 | 0 | 0 | 0 | 0 | 0 | 0 | 0 |
| −0.8087 | −2.6954 | 0.0877 | H | 0 | 0 | 0 | 0 | 0 | 0 | 0 | 0 | 0 | 0 | 0 | 0 |
| −1.3176 | 0.4380 | 2.1369 | H | 0 | 0 | 0 | 0 | 0 | 0 | 0 | 0 | 0 | 0 | 0 | 0 |
| −1.4650 | −0.8311 | 3.3313 | H | 0 | 0 | 0 | 0 | 0 | 0 | 0 | 0 | 0 | 0 | 0 | 0 |
| 0.2955 | −2.1703 | 2.2412 | H | 0 | 0 | 0 | 0 | 0 | 0 | 0 | 0 | 0 | 0 | 0 | 0 |
| 0.5794 | −0.9078 | 1.0429 | H | 0 | 0 | 0 | 0 | 0 | 0 | 0 | 0 | 0 | 0 | 0 | 0 |
| 0.5155 | 1.5425 | 5.0190 | H | 0 | 0 | 0 | 0 | 0 | 0 | 0 | 0 | 0 | 0 | 0 | 0 |
| 1 | 3 | 1 | 0 | 0 | 0 | 0 | | | | | | | | | |
| 1 | 5 | 2 | 0 | 0 | 0 | 0 | | | | | | | | | |
| 1 | 6 | 1 | 0 | 0 | 0 | 0 | | | | | | | | | |
| 2 | 4 | 1 | 0 | 0 | 0 | 0 | | | | | | | | | |
| 3 | 4 | 1 | 0 | 0 | 0 | 0 | | | | | | | | | |
| 2 | 7 | 1 | 0 | 0 | 0 | 0 | | | | | | | | | |
| 2 | 8 | 1 | 0 | 0 | 0 | 0 | | | | | | | | | |
| 2 | 9 | 1 | 0 | 0 | 0 | 0 | | | | | | | | | |
| 3 | 10 | 1 | 0 | 0 | 0 | 0 | | | | | | | | | |
| 3 | 11 | 1 | 0 | 0 | 0 | 0 | | | | | | | | | |
| 4 | 12 | 1 | 0 | 0 | 0 | 0 | | | | | | | | | |
| 4 | 13 | 1 | 0 | 0 | 0 | 0 | | | | | | | | | |
| 6 | 14 | 1 | 0 | 0 | 0 | 0 | | | | | | | | | | octanoic acid

| | | | | | | | | | | | | | | | |
|---|---|---|---|---|---|---|---|---|---|---|---|---|---|---|---|
| 26 | 25 | 0 | 0 | 0 | 0 | 0 | 0 | 0999 | V2000 | | | | | | |
| −5.5871 | 2.3515 | 6.1720 | C | 0 | 0 | 0 | 0 | 0 | 0 | 0 | 0 | 0 | 0 | 0 | 0 |
| −4.1506 | −0.6010 | −2.1366 | C | 0 | 0 | 0 | 0 | 0 | 0 | 0 | 0 | 0 | 0 | 0 | 0 |
| −5.9741 | 1.5205 | 4.9697 | C | 0 | 0 | 0 | 0 | 0 | 0 | 0 | 0 | 0 | 0 | 0 | 0 |
| −3.7365 | 0.2157 | −0.9229 | C | 0 | 0 | 0 | 0 | 0 | 0 | 0 | 0 | 0 | 0 | 0 | 0 |
| −4.9815 | 1.6867 | 3.8197 | C | 0 | 0 | 0 | 0 | 0 | 0 | 0 | 0 | 0 | 0 | 0 | 0 |
| −4.7611 | 0.0998 | 0.2066 | C | 0 | 0 | 0 | 0 | 0 | 0 | 0 | 0 | 0 | 0 | 0 | 0 |
| −5.3459 | 0.8694 | 2.5770 | C | 0 | 0 | 0 | 0 | 0 | 0 | 0 | 0 | 0 | 0 | 0 | 0 |
| −4.3571 | 0.9535 | 1.4103 | C | 0 | 0 | 0 | 0 | 0 | 0 | 0 | 0 | 0 | 0 | 0 | 0 |
| −4.5993 | 3.0682 | 6.2520 | O | 0 | 0 | 0 | 0 | 0 | 0 | 0 | 0 | 0 | 0 | 0 | 0 |
| −6.4877 | 2.2145 | 7.1803 | O | 0 | 0 | 0 | 0 | 0 | 0 | 0 | 0 | 0 | 0 | 0 | 0 |
| −4.2720 | −1.6574 | −1.8760 | H | 0 | 0 | 0 | 0 | 0 | 0 | 0 | 0 | 0 | 0 | 0 | 0 |
| −3.3889 | −0.5295 | −2.9193 | H | 0 | 0 | 0 | 0 | 0 | 0 | 0 | 0 | 0 | 0 | 0 | 0 |
| −5.0971 | −0.2376 | −2.5493 | H | 0 | 0 | 0 | 0 | 0 | 0 | 0 | 0 | 0 | 0 | 0 | 0 |
| −6.0066 | 0.4694 | 5.2771 | H | 0 | 0 | 0 | 0 | 0 | 0 | 0 | 0 | 0 | 0 | 0 | 0 |
| −6.9742 | 1.8363 | 4.6553 | H | 0 | 0 | 0 | 0 | 0 | 0 | 0 | 0 | 0 | 0 | 0 | 0 |
| −3.6240 | 1.2653 | −1.2178 | H | 0 | 0 | 0 | 0 | 0 | 0 | 0 | 0 | 0 | 0 | 0 | 0 |
| −2.7568 | −0.1304 | −0.5735 | H | 0 | 0 | 0 | 0 | 0 | 0 | 0 | 0 | 0 | 0 | 0 | 0 |
| −3.9853 | 1.3694 | 4.1543 | H | 0 | 0 | 0 | 0 | 0 | 0 | 0 | 0 | 0 | 0 | 0 | 0 |
| −4.8847 | 2.7475 | 3.5602 | H | 0 | 0 | 0 | 0 | 0 | 0 | 0 | 0 | 0 | 0 | 0 | 0 |
| −4.8480 | −0.9513 | 0.5038 | H | 0 | 0 | 0 | 0 | 0 | 0 | 0 | 0 | 0 | 0 | 0 | 0 |
| −5.7456 | 0.4184 | −0.1566 | H | 0 | 0 | 0 | 0 | 0 | 0 | 0 | 0 | 0 | 0 | 0 | 0 |
| −6.3317 | 1.1912 | 2.2185 | H | 0 | 0 | 0 | 0 | 0 | 0 | 0 | 0 | 0 | 0 | 0 | 0 |
| −5.4554 | −0.1812 | 2.8738 | H | 0 | 0 | 0 | 0 | 0 | 0 | 0 | 0 | 0 | 0 | 0 | 0 |
| −4.2912 | 2.0036 | 1.0984 | H | 0 | 0 | 0 | 0 | 0 | 0 | 0 | 0 | 0 | 0 | 0 | 0 |
| −3.3531 | 0.6706 | 1.7470 | H | 0 | 0 | 0 | 0 | 0 | 0 | 0 | 0 | 0 | 0 | 0 | 0 |
| −6.2885 | 2.7366 | 7.9868 | H | 0 | 0 | 0 | 0 | 0 | 0 | 0 | 0 | 0 | 0 | 0 | 0 |
| 1 | 3 | 1 | 0 | 0 | 0 | 0 | | | | | | | | | |
| 1 | 9 | 2 | 0 | 0 | 0 | 0 | | | | | | | | | |
| 1 | 10 | 1 | 0 | 0 | 0 | 0 | | | | | | | | | |
| 2 | 4 | 1 | 0 | 0 | 0 | 0 | | | | | | | | | |
| 3 | 5 | 1 | 0 | 0 | 0 | 0 | | | | | | | | | |
| 4 | 6 | 1 | 0 | 0 | 0 | 0 | | | | | | | | | |
| 5 | 7 | 1 | 0 | 0 | 0 | 0 | | | | | | | | | |
| 6 | 8 | 1 | 0 | 0 | 0 | 0 | | | | | | | | | |
| 7 | 8 | 1 | 0 | 0 | 0 | 0 | | | | | | | | | |
| 2 | 11 | 1 | 0 | 0 | 0 | 0 | | | | | | | | | |
| 2 | 12 | 1 | 0 | 0 | 0 | 0 | | | | | | | | | |
| 2 | 13 | 1 | 0 | 0 | 0 | 0 | | | | | | | | | |
| 3 | 14 | 1 | 0 | 0 | 0 | 0 | | | | | | | | | |
| 3 | 15 | 1 | 0 | 0 | 0 | 0 | | | | | | | | | |

TABLE 1-continued

Structure Data Files (SDF) for the 11 strongest
CO2 receptor inhibitors we have identified. Information in the sdf
file can be used to generate 3-dimensional shapes of these compounds.

| | | | | | | | |
|---|---|---|---|---|---|---|---|
| 4 | 16 | 1 | 0 | 0 | 0 | 0 | |
| 4 | 17 | 1 | 0 | 0 | 0 | 0 | |
| 5 | 18 | 1 | 0 | 0 | 0 | 0 | |
| 5 | 19 | 1 | 0 | 0 | 0 | 0 | |
| 6 | 20 | 1 | 0 | 0 | 0 | 0 | |
| 6 | 21 | 1 | 0 | 0 | 0 | 0 | |
| 7 | 22 | 1 | 0 | 0 | 0 | 0 | |
| 7 | 23 | 1 | 0 | 0 | 0 | 0 | |
| 8 | 24 | 1 | 0 | 0 | 0 | 0 | |
| 8 | 25 | 1 | 0 | 0 | 0 | 0 | |
| 10 | 26 | 1 | 0 | 0 | 0 | 0 | |

1-hepten-3-ol

| 22 | 21 | 0 | 1 | 0 | 0 | 0 | 0 | 0 | 0999 | | V2000 | | | |
|---|---|---|---|---|---|---|---|---|---|---|---|---|---|---|
| 0.5941 | 0.1375 | 0.8021 | C | 0 | 0 | 0 | 0 | 0 | 0 | 0 | 0 | 0 | 0 | 0 |
| 0.2938 | −0.3231 | 2.0217 | C | 0 | 0 | 0 | 0 | 0 | 0 | 0 | 0 | 0 | 0 | 0 |
| 0.1270 | −5.7681 | 1.5049 | C | 0 | 0 | 0 | 0 | 0 | 0 | 0 | 0 | 0 | 0 | 0 |
| −0.3781 | −4.7539 | 2.5187 | C | 0 | 0 | 0 | 0 | 0 | 0 | 0 | 0 | 0 | 0 | 0 |
| −0.3861 | −3.3388 | 1.9392 | C | 0 | 0 | 0 | 0 | 0 | 0 | 0 | 0 | 0 | 0 | 0 |
| −0.9345 | −2.3291 | 2.9505 | C | 0 | 0 | 0 | 0 | 0 | 0 | 0 | 0 | 0 | 0 | 0 |
| −1.0406 | −0.9051 | 2.3909 | C | 0 | 0 | 1 | 0 | 0 | 0 | 0 | 0 | 0 | 0 | 0 |
| −1.6247 | −0.0861 | 3.4055 | O | 0 | 0 | 0 | 0 | 0 | 0 | 0 | 0 | 0 | 0 | 0 |
| 1.5764 | 0.5484 | 0.5965 | H | 0 | 0 | 0 | 0 | 0 | 0 | 0 | 0 | 0 | 0 | 0 |
| −0.1274 | 0.1124 | −0.0069 | H | 0 | 0 | 0 | 0 | 0 | 0 | 0 | 0 | 0 | 0 | 0 |
| 1.0538 | −0.2741 | 2.7975 | H | 0 | 0 | 0 | 0 | 0 | 0 | 0 | 0 | 0 | 0 | 0 |
| 1.1384 | −5.5174 | 1.1697 | H | 0 | 0 | 0 | 0 | 0 | 0 | 0 | 0 | 0 | 0 | 0 |
| 0.1548 | −6.7675 | 1.9501 | H | 0 | 0 | 0 | 0 | 0 | 0 | 0 | 0 | 0 | 0 | 0 |
| −0.5268 | −5.8050 | 0.6276 | H | 0 | 0 | 0 | 0 | 0 | 0 | 0 | 0 | 0 | 0 | 0 |
| −1.3904 | −5.0336 | 2.8328 | H | 0 | 0 | 0 | 0 | 0 | 0 | 0 | 0 | 0 | 0 | 0 |
| 0.2595 | −4.7878 | 3.4097 | H | 0 | 0 | 0 | 0 | 0 | 0 | 0 | 0 | 0 | 0 | 0 |
| 0.6340 | −3.0636 | 1.6475 | H | 0 | 0 | 0 | 0 | 0 | 0 | 0 | 0 | 0 | 0 | 0 |
| −1.0005 | −3.3183 | 1.0309 | H | 0 | 0 | 0 | 0 | 0 | 0 | 0 | 0 | 0 | 0 | 0 |
| −0.3114 | −2.3288 | 3.8551 | H | 0 | 0 | 0 | 0 | 0 | 0 | 0 | 0 | 0 | 0 | 0 |
| −1.9307 | −2.6492 | 3.2841 | H | 0 | 0 | 0 | 0 | 0 | 0 | 0 | 0 | 0 | 0 | 0 |
| −1.7276 | −0.9018 | 1.5362 | H | 0 | 0 | 0 | 0 | 0 | 0 | 0 | 0 | 0 | 0 | 0 |
| −2.4802 | −0.4867 | 3.6204 | H | 0 | 0 | 0 | 0 | 0 | 0 | 0 | 0 | 0 | 0 | 0 |
| 1 | 2 | | 2 | | 0 | | 0 | | 0 | | 0 | | | |
| 2 | 7 | | 1 | | 0 | | 0 | | 0 | | 0 | | | |
| 3 | 4 | | 1 | | 0 | | 0 | | 0 | | 0 | | | |
| 4 | 5 | | 1 | | 0 | | 0 | | 0 | | 0 | | | |
| 5 | 6 | | 1 | | 0 | | 0 | | 0 | | 0 | | | |
| 6 | 7 | | 1 | | 0 | | 0 | | 0 | | 0 | | | |
| 7 | 8 | | 1 | | 0 | | 0 | | 0 | | 0 | | | |
| 1 | 9 | | 1 | | 0 | | 0 | | 0 | | 0 | | | |
| 1 | 10 | | 1 | | 0 | | 0 | | 0 | | 0 | | | |
| 2 | 11 | | 1 | | 0 | | 0 | | 0 | | 0 | | | |
| 3 | 12 | | 1 | | 0 | | 0 | | 0 | | 0 | | | |
| 3 | 13 | | 1 | | 0 | | 0 | | 0 | | 0 | | | |
| 3 | 14 | | 1 | | 0 | | 0 | | 0 | | 0 | | | |
| 4 | 15 | | 1 | | 0 | | 0 | | 0 | | 0 | | | |
| 4 | 16 | | 1 | | 0 | | 0 | | 0 | | 0 | | | |
| 5 | 17 | | 1 | | 0 | | 0 | | 0 | | 0 | | | |
| 5 | 18 | | 1 | | 0 | | 0 | | 0 | | 0 | | | |
| 6 | 19 | | 1 | | 0 | | 0 | | 0 | | 0 | | | |
| 6 | 20 | | 1 | | 0 | | 0 | | 0 | | 0 | | | |
| 7 | 21 | | 1 | | 0 | | 0 | | 0 | | 0 | | | |
| 8 | 22 | | 1 | | 0 | | 0 | | 0 | | 0 | | | | methyethyl ketone-butanone

| 13 | 12 | 0 | 0 | 0 | 0 | 0 | 0 | 0 | 0999 | | V2000 | | | |
|---|---|---|---|---|---|---|---|---|---|---|---|---|---|---|
| −0.1717 | 1.2834 | −2.1497 | O | 0 | 0 | 0 | 0 | 0 | 0 | 0 | 0 | 0 | 0 | 0 |
| 1.8758 | 0.2660 | −2.9330 | C | 0 | 0 | 0 | 0 | 0 | 0 | 0 | 0 | 0 | 0 | 0 |
| 0.7570 | 0.5057 | −1.9361 | C | 0 | 0 | 0 | 0 | 0 | 0 | 0 | 0 | 0 | 0 | 0 |
| 1.6992 | 1.0628 | −4.2128 | C | 0 | 0 | 0 | 0 | 0 | 0 | 0 | 0 | 0 | 0 | 0 |
| 0.8396 | −0.2698 | −0.6470 | C | 0 | 0 | 0 | 0 | 0 | 0 | 0 | 0 | 0 | 0 | 0 |
| 2.8225 | 0.5416 | −2.4567 | H | 0 | 0 | 0 | 0 | 0 | 0 | 0 | 0 | 0 | 0 | 0 |
| 1.8999 | −0.8030 | −3.1689 | H | 0 | 0 | 0 | 0 | 0 | 0 | 0 | 0 | 0 | 0 | 0 |
| 2.5228 | 0.8607 | −4.9045 | H | 0 | 0 | 0 | 0 | 0 | 0 | 0 | 0 | 0 | 0 | 0 |
| 1.6812 | 2.1382 | −4.0073 | H | 0 | 0 | 0 | 0 | 0 | 0 | 0 | 0 | 0 | 0 | 0 |
| 0.7605 | 0.8014 | −4.7124 | H | 0 | 0 | 0 | 0 | 0 | 0 | 0 | 0 | 0 | 0 | 0 |
| 1.7637 | −0.0126 | −0.1235 | H | 0 | 0 | 0 | 0 | 0 | 0 | 0 | 0 | 0 | 0 | 0 |
| −0.0108 | −0.0156 | −0.0081 | H | 0 | 0 | 0 | 0 | 0 | 0 | 0 | 0 | 0 | 0 | 0 |
| 0.8125 | −1.3409 | −0.8616 | H | 0 | 0 | 0 | 0 | 0 | 0 | 0 | 0 | 0 | 0 | 0 |
| 1 | 3 | | 2 | | 0 | | 0 | | 0 | | 0 | | | |
| 2 | 3 | | 1 | | 0 | | 0 | | 0 | | 0 | | | |
| 2 | 4 | | 1 | | 0 | | 0 | | 0 | | 0 | | | |

TABLE 1-continued

Structure Data Files (SDF) for the 11 strongest
CO2 receptor inhibitors we have identified. Information in the sdf
file can be used to generate 3-dimensional shapes of these compounds.

| | | | | | | |
|---|---|---|---|---|---|---|
| 2 | 6 | 1 | 0 | 0 | 0 | 0 |
| 2 | 7 | 1 | 0 | 0 | 0 | 0 |
| 3 | 5 | 1 | 0 | 0 | 0 | 0 |
| 4 | 8 | 1 | 0 | 0 | 0 | 0 |
| 4 | 9 | 1 | 0 | 0 | 0 | 0 |
| 4 | 10 | 1 | 0 | 0 | 0 | 0 |
| 5 | 11 | 1 | 0 | 0 | 0 | 0 |
| 5 | 12 | 1 | 0 | 0 | 0 | 0 |
| 5 | 13 | 1 | 0 | 0 | 0 | 0 |

TABLE 2

| Pubchem Substance | Smiles Structure |
|---|---|
| PubChem_Substance: 102233 | O=CCCCCl |
| PubChem_Substance: 109783 | CCCCCCC |
| PubChem_Substance: 1099 | CCC(O)=O |
| PubChem_Substance: 110791 | CC(=O)C(=O)OC |
| PubChem_Substance: 114269 | BrCCCCCC |
| PubChem_Substance: 116200 | C(C)C(=O)S |
| PubChem_Substance: 121698 | C(C)C(=O)Cl |
| PubChem_Substance: 122044 | C(CC)SCCO |
| PubChem_Substance: 10504 | C(CCC)CCN |
| PubChem_Substance: 1112 | C(=O)(C(O)=O)C |
| PubChem_Substance: 111548 | CC(=O)[C@@H](C)CC |
| PubChem_Substance: 115145 | C(C)C(C)=C |
| PubChem_Substance: 117269 | CC(=O)\C(C)=C/C |
| PubChem_Substance: 118093 | CC[C@@H](C)C=O |
| PubChem_Substance: 130355 | OCCCCOCC |
| PubChem_Substance: 136211 | O(C)CCCCO |
| PubChem_Substance: 1434028 | CC(=O)CO |
| PubChem_Substance: 149090 | C(CCC)CC=O |
| PubChem_Substance: 149209 | C(CCO)CC |
| PubChem_Substance: 149535 | C(CCl)(C)=O |
| PubChem_Substance: 149544 | C(CC)(N)=O |
| PubChem_Substance: 149553 | C(NC)(C)=O |
| PubChem_Substance: 149556 | C(OC)(C)=O |
| PubChem_Substance: 151118 | C(CC)C=C |
| PubChem_Substance: 151140 | O(CC)C=O |
| PubChem_Substance: 151183 | C(CC=O)CC |
| PubChem_Substance: 151227 | C(CCC)CCBr |
| PubChem_Substance: 151231 | C(CCO)CCO |
| PubChem_Substance: 151233 | C(CCC)CCS |
| PubChem_Substance: 151234 | C(CCO)COC |
| PubChem_Substance: 151236 | C(CCO)OCC |
| PubChem_Substance: 151258 | C(CCCO)CCC |
| PubChem_Substance: 151260 | C(COCC)CCO |
| PubChem_Substance: 151357 | C(C(=O)[O-])(C)=O•[Na+] |
| PubChem_Substance: 151437 | C(CO)(C)=O |
| PubChem_Substance: 151881 | C(CC)(=O)[O-]•[Na+] |
| PubChem_Substance: 152052 | C(CCC)CCC |
| PubChem_Substance: 152976 | C(CCC)CCF |
| PubChem_Substance: 154295 | C(CCC)CCCl |
| PubChem_Substance: 154544 | C(CC)(C)=C |
| PubChem_Substance: 154566 | C([C@@H](CC)C)(C)=O |
| PubChem_Substance: 155053 | C(C(C)=O)(CC)=O |
| PubChem_Substance: 155642 | N(CC)C=O |
| PubChem_Substance: 155851 | C(CCC)CCl |
| PubChem_Substance: 160882 | O(CCC)CCO |
| PubChem_Substance: 161640 | C(CSC)C=O |
| PubChem_Substance: 16299 | C(COC)=O |
| PubChem_Substance: 163716 | C(CCOC)CCO |
| PubChem_Substance: 166638 | C(C(C)C)(C(C)=O)=O |
| PubChem_Substance: 17090 | CC(=O)CCC |
| PubChem_Substance: 17092 | C([C@@H](C)O)C=O |
| PubChem_Substance: 17116 | CCC[N+]([O-])=O |
| PubChem_Substance: 171892 | C(C=O)CCl |
| PubChem_Substance: 17308 | O=COCC |
| PubChem_Substance: 173442 | C(N(C)C)(C)=O |
| PubChem_Substance: 173442 | C(N(C)C)(C)=O |
| PubChem_Substance: 17391 | O(CCC)C=O |
| PubChem_Substance: 17462 | C(CCCN)CC |
| PubChem_Substance: 17481 | C(COCC)CO |

TABLE 2-continued

| Pubchem Substance | Smiles Structure |
| --- | --- |
| PubChem_Substance: 174855 | C=CCCC |
| PubChem_Substance: 174923 | CCCCCCCl |
| PubChem_Substance: 175443 | C=C(CC)C |
| PubChem_Substance: 175493 | C(CCCO)CCC•C* |
| PubChem_Substance: 17583 | C(CCCCO)CCC |
| PubChem_Substance: 1760569 | CC(=O)CC#N |
| PubChem_Substance: 180990 | C(C(C)=C)(OC)=O•C(C(C)=O)(C)=C |
| PubChem_Substance: 181620 | C(CCCCCC)O |
| PubChem_Substance: 181951 | C(C(C)=O)(C)=C |
| PubChem_Substance: 1840 | ClC(=O)CCC |
| PubChem_Substance: 1918774 | CCC(=O)NN |
| PubChem_Substance: 1918822 | CCOC=O |
| PubChem_Substance: 19420 | CC(C(=O)O)=O |
| PubChem_Substance: 19420 | CC(C(=O)O)=O |
| PubChem_Substance: 2022 | C(=O)CCCN |
| PubChem_Substance: 203598 | C(CC)(=O)Cl |
| PubChem_Substance: 20687 | CC(C(=[N+]=[N-])C)=O |
| PubChem_Substance: 20694 | O=[S@@](C)CCC |
| PubChem_Substance: 20771 | C(C(Cl)=O)CC |
| PubChem_Substance: 20879 | CCCCCCN•Cl |
| PubChem_Substance: 20914 | C1C(=C1C)C |
| PubChem_Substance: 210159 | O=CCCCF |
| PubChem_Substance: 211181 | C(=O)(Br)CC |
| PubChem_Substance: 212133 | O=C(C)C(C)C(=O)C |
| PubChem_Substance: 212385 | C(=O)C(=C)CC |
| PubChem_Substance: 212796 | [Si]CCCCCC |
| PubChem_Substance: 2130 | C(N)C(C)=O |
| PubChem_Substance: 213258 | C(CC)([O-])=O•[K+] |
| PubChem_Substance: 216920 | C(=O)(S)CC |
| PubChem_Substance: 217276 | O=CCCO |
| PubChem_Substance: 2182 | C(=O)(O)CCC |
| PubChem_Substance: 21847 | S(C(C)=O)C |
| PubChem_Substance: 22074 | CCCC([O-])=O•[Na+] |
| PubChem_Substance: 22218 | CC[C]=O |
| PubChem_Substance: 22624 | CCCNCCO |
| PubChem_Substance: 22860 | O=[S@@](C)CC |
| PubChem_Substance: 248693 | C(CCOO)CC |
| PubChem_Substance: 248741 | CCC=O |
| PubChem_Substance: 249659 | OCCCCCO |
| PubChem_Substance: 249667 | C(CCCO)OCC |
| PubChem_Substance: 249861 | C1(=C(C(C1=O)=O)C)C |
| PubChem_Substance: 250119 | C([C@@H](C=O)C)C |
| PubChem_Substance: 252378 | C(CC=C)C |
| PubChem_Substance: 252391 | CCCCCO |
| PubChem_Substance: 252453 | C(\CCC)=N\C |
| PubChem_Substance: 253031 | C(C(C)=O)F |
| PubChem_Substance: 253136 | C(C(CC)=O)(C)=O |
| PubChem_Substance: 253185 | C(C(C)=O)O |
| PubChem_Substance: 253361 | C(C(=C)C)(=O)C |
| PubChem_Substance: 253720 | C(C(C(C)=O)=O)(C)C |
| PubChem_Substance: 25509 | OCCCCSC |
| PubChem_Substance: 255500 | S(CCC)CCO |
| PubChem_Substance: 256154 | CC(C(=O)C)C(=O)C |
| PubChem_Substance: 256665 | CC(C(CS)=O)=O |
| PubChem_Substance: 25725 | CC([Se]C)=O |
| PubChem_Substance: 257478 | C(\C(=N\O)C)(C)=O |
| PubChem_Substance: 257599 | P(C(C)=O)(C)C |
| PubChem_Substance: 25776 | C(SCC)=O |
| PubChem_Substance: 25898 | C(C=O)CO |
| PubChem_Substance: 261522 | C(CCC)C=O |
| PubChem_Substance: 262285 | C(CCCO)COC |
| PubChem_Substance: 262615 | C(CCOC)CO |
| PubChem_Substance: 263328 | C(CC=O)SC |
| PubChem_Substance: 263765 | C(=O)CCC#N |
| PubChem_Substance: 264232 | C(CC=C)C=O |
| PubChem_Substance: 264630 | C(CCCO)CCl |
| PubChem_Substance: 264783 | C(\C(=C\C)C)(C)=O |
| PubChem_Substance: 265215 | C(C(C)=C)C |
| PubChem_Substance: 266400 | C(CCCS)CC |
| PubChem_Substance: 270338 | CCNCCCCO |
| PubChem_Substance: 271990 | C(CCC[Si])CC |
| PubChem_Substance: 277133 | C(CCCC)CCO |
| PubChem_Substance: 28236 | C(C=O)C(C)C |
| PubChem_Substance: 28907 | C(CCOC)=O |
| PubChem_Substance: 28914 | C(OCCO)CC |
| PubChem_Substance: 29724 | CC(=O)Cl |
| PubChem_Substance: 29895 | S1(C(=C1C)C)(=O)=O |
| PubChem_Substance: 3023 | CCCCCCCCCO |

TABLE 2-continued

| Pubchem Substance | Smiles Structure |
|---|---|
| PubChem_Substance: 3132272 | C(C(=O)C)(=O)C |
| PubChem_Substance: 3132315 | C(=O)(N)CCC |
| PubChem_Substance: 3132972 | CC(N(C)C)=O |
| PubChem_Substance: 3133377 | OCCCCCCC |
| PubChem_Substance: 3133822 | C(=O)(NC)C |
| PubChem_Substance: 3133857 | O=C[C@@H](CC)C |
| PubChem_Substance: 3133962 | C(C(=O)C)(=O)OC |
| PubChem_Substance: 3134074 | [N+]([O-])(=O)CCC |
| PubChem_Substance: 3134306 | O=CCC |
| PubChem_Substance: 3134308 | C(=C)(Cl)CC |
| PubChem_Substance: 3134354 | C(C(=O)C)(=O)O |
| PubChem_Substance: 3134355 | C(C(=O)C)(=O)[O-]•[Na+] |
| PubChem_Substance: 3135153 | C(=O)(Cl)CCC |
| PubChem_Substance: 3135162 | C(=O)(O)CC |
| PubChem_Substance: 3135258 | C(\C(=O)C)(=N/O)C |
| PubChem_Substance: 3135285 | C(=O)OCC |
| PubChem_Substance: 3135381 | O=C(CF)C |
| PubChem_Substance: 3135387 | O=CCCCCC |
| PubChem_Substance: 3135551 | NCCCCCO |
| PubChem_Substance: 3136103 | O=C(CO)C |
| PubChem_Substance: 3136387 | O=CCC(C)C |
| PubChem_Substance: 3138604 | NCCCCCC |
| PubChem_Substance: 3139114 | SCCCCCC |
| PubChem_Substance: 3139265 | ICCCCCC |
| PubChem_Substance: 3139326 | C(C(=O)CC)(=O)C |
| PubChem_Substance: 3139329 | C(=C)CCC |
| PubChem_Substance: 3140473 | C([O-])(=O)CCC•[Na+] |
| PubChem_Substance: 3153246 | C(=O)OCCC |
| PubChem_Substance: 3154683 | N(=C\CCC)\O |
| PubChem_Substance: 3154784 | OCCOCCC |
| PubChem_Substance: 3156532 | ClCCCCCC |
| PubChem_Substance: 3156880 | FCCCCCC |
| PubChem_Substance: 3157074 | O=CCCSC |
| PubChem_Substance: 3160315 | C\C=C(\C(C)=O)C |
| PubChem_Substance: 3210042 | C[C@@H](C(C)=O)F |
| PubChem_Substance: 3222925 | BrCCCCCO |
| PubChem_Substance: 32291 | C(CCCF)CC |
| PubChem_Substance: 3324 | C(C(O)=O)(C)=O |
| PubChem_Substance: 33364 | C(\CCC)=C\C |
| PubChem_Substance: 34137 | CCC(F)=O |
| PubChem_Substance: 3545 | C(C(O)=O)CC |
| PubChem_Substance: 36405 | CCCCCO[O] |
| PubChem_Substance: 3737031 | C(CCCC)=O |
| PubChem_Substance: 3739966 | [Mg+2]•C(CCCC)[O-] |
| PubChem_Substance: 3740350 | BrCCCC=O |
| PubChem_Substance: 3741796 | [Pb]•C(CC)(=O)[O-] |
| PubChem_Substance: 3743226 | [Ca+2]•C(C(C)=O)(=O)[O-] |
| PubChem_Substance: 37465 | C(CCCCl)CC |
| PubChem_Substance: 3762 | C(C=O)C |
| PubChem_Substance: 3764841 | [Al]•C(CCCCCC)[O-] |
| PubChem_Substance: 3765039 | ClNCC(C)=O |
| PubChem_Substance: 3835 | C(CC=O)CN |
| PubChem_Substance: 38424 | C(C(C)C)(C)=O |
| PubChem_Substance: 3856796 | C(CC)[Se](=O)O |
| PubChem_Substance: 38690 | O=C(Cl)C(=O)C |
| PubChem_Substance: 3884 | C(C=O)C* |
| PubChem_Substance: 3885036 | [K+]•CCCC([O-])=O |
| PubChem_Substance: 3885543 | [Ag]•CCC(O)=O |
| PubChem_Substance: 3885659 | [Li+]•CCC([O-])=O |
| PubChem_Substance: 3885723 | [Mg+2]•CC(=C)C([O-])=O•CC(=C)C([O-])=O |
| PubChem_Substance: 3885772 | Cl•CC(=O)CN |
| PubChem_Substance: 3886310 | [Li]CCCCCC |
| PubChem_Substance: 39792 | CCC(Br)=O |
| PubChem_Substance: 39798 | CC(=O)CBr |
| PubChem_Substance: 39895 | C(C(OC)=O)(C)=O |
| PubChem_Substance: 4018 | C(CCCC)CCCO |
| PubChem_Substance: 402905 | CCCCCCS |
| PubChem_Substance: 412145 | C(\C(=N\O)C)(=O)C |
| PubChem_Substance: 41519 | C(=O)NCC |
| PubChem_Substance: 41576 | CCCNC=O |
| PubChem_Substance: 41800 | CC(C(N)=O)=O |
| PubChem_Substance: 42078 | CCCCCCl |
| PubChem_Substance: 4219 | C(CO)C=O |
| PubChem_Substance: 425697 | OCCCSCC |
| PubChem_Substance: 425699 | OCCCCSCC |
| PubChem_Substance: 42661 | CCCCCC=O |
| PubChem_Substance: 441141 | CO•OCC(=O)C |
| PubChem_Substance: 44172 | CCC([O-])=O |

TABLE 2-continued

| Pubchem Substance | Smiles Structure |
| --- | --- |
| PubChem_Substance: 441760 | CCCCCC[Si] |
| PubChem_Substance: 44467 | CCCC(C=O)=O |
| PubChem_Substance: 445514 | C(#N)CCC#N•CCCC=O |
| PubChem_Substance: 45438 | C(\CCC)=C/C |
| PubChem_Substance: 46038 | C(C(Cl)=O)C |
| PubChem_Substance: 46041 | CCC(N)=O |
| PubChem_Substance: 46059 | N(C(C)=O)C |
| PubChem_Substance: 46063 | CC(OC)=O |
| PubChem_Substance: 461796 | O=C(\C(C)=C/O)C |
| PubChem_Substance: 463014 | C(=O)(C(=O)N)C |
| PubChem_Substance: 475221 | COC(=O)C |
| PubChem_Substance: 47650 | CC(N(C)C)=O•Cl |
| PubChem_Substance: 47690 | C(C(=C)C=O)C |
| PubChem_Substance: 480130 | O=CN(CC)C |
| PubChem_Substance: 5052 | C(C(C)=O)CC |
| PubChem_Substance: 5293 | C(CN)C=O |
| PubChem_Substance: 539318 | C(C(=O)O)CC |
| PubChem_Substance: 54660 | C([C@@H](S)C)C=O |
| PubChem_Substance: 561460 | C(CN)(C)=O |
| PubChem_Substance: 568479 | C([Se](=O)O)CC |
| PubChem_Substance: 584948 | C(N)CC=O |
| PubChem_Substance: 587311 | CCC(CC)=O |
| PubChem_Substance: 587327 | C(=O)(COC)C |
| PubChem_Substance: 587828 | C(CCCC)O |
| PubChem_Substance: 587964 | C(C)(C(C)C)=O |
| PubChem_Substance: 587967 | CC(C(=C)C)=O |
| PubChem_Substance: 588196 | CC([C@@H](C)O)=O |
| PubChem_Substance: 588421 | C(OCC)=O |
| PubChem_Substance: 588550 | C=C=C(CC)C |
| PubChem_Substance: 589554 | C(C=O)CCC |
| PubChem_Substance: 589557 | CC(CCC)=O |
| PubChem_Substance: 589566 | C(C(C)=O)Cl |
| PubChem_Substance: 589567 | OCCC(C)=O |
| PubChem_Substance: 589568 | BrCC(C)=O |
| PubChem_Substance: 589569 | FCC(C)=O |
| PubChem_Substance: 589803 | C([N+]([O-])=O)CC |
| PubChem_Substance: 589832 | C(\CCC)=N/O |
| PubChem_Substance: 591719 | C\C=C\CCC |
| PubChem_Substance: 591720 | C(=C/CCC)\C |
| PubChem_Substance: 594020 | C(=O)(C)NC |
| PubChem_Substance: 594446 | CCCC=C |
| PubChem_Substance: 594453 | CCCC(Cl)=O |
| PubChem_Substance: 595587 | C1(C(=C1C)C)=O |
| PubChem_Substance: 62556 | CC(=O)\C(=N\O)C |
| PubChem_Substance: 653595 | O(CCCC)CO |
| PubChem_Substance: 654120 | N#CCCC=O |
| PubChem_Substance: 654438 | [Mg+]CCCCCC•[Br-] |
| PubChem_Substance: 654854 | [O-]C(=O)C(=O)C•[K+] |
| PubChem_Substance: 655924 | OCCCCCCl |
| PubChem_Substance: 656064 | C(\C(=O)C)(=C\C)C |
| PubChem_Substance: 656106 | C(C(=O)C)(=O)N |
| PubChem_Substance: 658836 | C(CC)(C)=C=C |
| PubChem_Substance: 659205 | C(=O)(O)C•CCC(O)=O |
| PubChem_Substance: 660708 | O=C(C)CC=C |
| PubChem_Substance: 662245 | OCCNCCC |
| PubChem_Substance: 663973 | C(=O)(O)CC•N |
| PubChem_Substance: 664590 | S(CCCO)CC |
| PubChem_Substance: 666627 | S(CCO)CCC |
| PubChem_Substance: 668333 | C(OC)C=O |
| PubChem_Substance: 670052 | O=CCCCO |
| PubChem_Substance: 671725 | C(C(=O)N)C•C(#N)•*Br•*Br |
| PubChem_Substance: 67631 | CNC(=O)C |
| PubChem_Substance: 681332 | O=[P@@](O)(CC)C |
| PubChem_Substance: 682207 | CCCC([O-])=O |
| PubChem_Substance: 68288 | N(\O)=C/CCC |
| PubChem_Substance: 684999 | CC(C(=O)[O-])=O |
| PubChem_Substance: 685039 | OC(CCC)=O•[OH-]•[Li+] |
| PubChem_Substance: 688784 | CC(=O)CCO |
| PubChem_Substance: 690631 | [O-]CCCCC•[Mg + 2]•[Cl-] |
| PubChem_Substance: 69218 | CCCCCN |
| PubChem_Substance: 695394 | OCCCCCBr |
| PubChem_Substance: 69667 | N(C)(C)C(=O)C |
| PubChem_Substance: 697005 | FCCCCCO |
| PubChem_Substance: 698876 | O=CCCCN |
| PubChem_Substance: 699833 | O=C(C=O)CCC |
| PubChem_Substance: 699964 | O=[S@@](CCC)C |
| PubChem_Substance: 70142 | CCCCCCCO |
| PubChem_Substance: 701811 | CC(C(NN)=O)=O |

TABLE 2-continued

| Pubchem Substance | Smiles Structure |
| --- | --- |
| PubChem_Substance: 706191 | CC(CC)=O•CC(CCC)=O |
| PubChem_Substance: 707283 | C(CCN)=O |
| PubChem_Substance: 707283 | C(CCN)=O |
| PubChem_Substance: 710995 | [Ba+2]•C(C(=C)C)(=O)[O-]•C(C(=C)C)(=O)[O-] |
| PubChem_Substance: 711171 | C(C(C)=O)(=O)O |
| PubChem_Substance: 712609 | C(=CCCC)=C |
| PubChem_Substance: 712967 | C(C(=O)C)(C(=O)C)=O |
| PubChem_Substance: 714019 | C1(N(CC1)C)=O |
| PubChem_Substance: 714071 | O=CCCOC |
| PubChem_Substance: 714264 | C(CCCC[CH2])C |
| PubChem_Substance: 714325 | C(CCC[CH]C)C |
| PubChem_Substance: 714582 | OOCCCCCC |
| PubChem_Substance: 71479 | C(CC)C(=O)C |
| PubChem_Substance: 716355 | [N+](=[N-])=C(C(=O)C)C |
| PubChem_Substance: 716411 | C1(=C(C1)C)C |
| PubChem_Substance: 716784 | O=[C]CC |
| PubChem_Substance: 717160 | C(=C)[CH]CC |
| PubChem_Substance: 717160 | C(=C)[CH]CC |
| PubChem_Substance: 717758 | C(=O)SCC |
| PubChem_Substance: 718339 | C(#C)CC(=O)C |
| PubChem_Substance: 718708 | C(=O)([C@@H](I)C)C |
| PubChem_Substance: 71938 | O=CNCCC |
| PubChem_Substance: 720279 | O([O])CCCCC |
| PubChem_Substance: 721170 | C(=C)(CC)[CH2] |
| PubChem_Substance: 72350 | C(CC)[N+]([O-])=O |
| PubChem_Substance: 723509 | C(=O)(C=O)CC |
| PubChem_Substance: 72461 | C(C)C=O |
| PubChem_Substance: 72461 | C(C)C=O |
| PubChem_Substance: 729313 | [Au+3]•[Cl-]•[Cl-]•[Cl-]•PCCCCCC |
| PubChem_Substance: 729314 | [Au+3]•[Br-]•[Br-]•[Br-]•PCCCCCC |
| PubChem_Substance: 73444 | C[C@@H](O)CC=O |
| PubChem_Substance: 73447 | CC(=O)C(=O)CC |
| PubChem_Substance: 734682 | C(CCCCC)C•*C |
| PubChem_Substance: 736416 | CCCCCCC•*C•*C |
| PubChem_Substance: 736651 | [O]OCC(C)=O |
| PubChem_Substance: 737943 | C(C(C)=O)N |
| PubChem_Substance: 739256 | [N+](CC)(C)(C)[O-] |
| PubChem_Substance: 739897 | P(=O)(O)(O)C•OCCCCCCC |
| PubChem_Substance: 740725 | C(CCC)=O•NCCCC |
| PubChem_Substance: 740726 | C(CCC)=O•Nc1ccccc1 |
| PubChem_Substance: 74110 | C(CC)C(=O)O |
| PubChem_Substance: 74119 | C(CC)C(=O)N |
| PubChem_Substance: 742182 | C(CCC)=[N+]=[N-] |
| PubChem_Substance: 742211 | CC([CH-]C=O)=O•[Na+] |
| PubChem_Substance: 742523 | [Li+]•C(C(C)=O)(=O)[O-] |
| PubChem_Substance: 743162 | c1(ccccc1)N•C(CCC)=O |
| PubChem_Substance: 748659 | C1O[C@@H]1C•C1OC1•OCCCCCC |
| PubChem_Substance: 74875 | C(C)(C)C(=O)C |
| PubChem_Substance: 749141 | [Sb+5]•[Cl-]•[Cl-]•[Cl-]•[Cl-]•[Cl-]•[Cl-]•[CH+](=O)CC |
| PubChem_Substance: 749590 | [BH3+3]•[F-]•[F-]•[F-]•[O-]C(CCC)=O |
| PubChem_Substance: 750934 | C(CCCl)=O |
| PubChem_Substance: 751298 | [NH4+]•C(CC)(=O)[O-] |
| PubChem_Substance: 751652 | [Zr+4]•C(CC)(=O)[O-] |
| PubChem_Substance: 752011 | [Ca+2]•C(C)(=O)[O-]•C(C)(=O)[O-]•[Na+]•C(CC)(=O)[O-] |
| PubChem_Substance: 76105 | O=CCCC=O |
| PubChem_Substance: 763015 | CCCCCCBr |
| PubChem_Substance: 763498 | C(C(C)=O)(=O)NC |
| PubChem_Substance: 770312 | C(CCCCC)[Se] |
| PubChem_Substance: 781346 | [Na+]•C(CC)(=O)[O-]•O |
| PubChem_Substance: 79548 | C(=O)(C)CC(=O)C)C |
| PubChem_Substance: 822750 | OCCCCCCCC |
| PubChem_Substance: 824014 | C(=O)(O)C(=O)C |
| PubChem_Substance: 824189 | C(O)(=O)C(=O)C |
| PubChem_Substance: 825651 | C(O)(=O)CCC |
| PubChem_Substance: 829160 | C[C@H](O)C(C)=O |
| PubChem_Substance: 829935 | O=C(C(=O)N)C |
| PubChem_Substance: 830121 | C([C@H](CC)N)=O |
| PubChem_Substance: 830282 | C(CCCCCC)O |
| PubChem_Substance: 831107 | CCCC(=O)N |
| PubChem_Substance: 831150 | C(N)(=O)C(=O)C |
| PubChem_Substance: 833290 | CCCC(=O)O |
| PubChem_Substance: 83691 | FCC(=O)C |
| PubChem_Substance: 837624 | CC(CCl)=O |
| PubChem_Substance: 839169 | C(=C(/CC)C)\C |
| PubChem_Substance: 840519 | C(=O)CCSC |
| PubChem_Substance: 840775 | CC(N(C(C)=O)C)=O |
| PubChem_Substance: 840846 | CCC[S@@](=O)O |
| PubChem_Substance: 840877 | C=C=CCCC |

TABLE 2-continued

| Pubchem Substance | Smiles Structure |
|---|---|
| PubChem_Substance: 841341 | OC(CCC)=O |
| PubChem_Substance: 841426 | OC(CC)=O |
| PubChem_Substance: 841530 | OCCCCC |
| PubChem_Substance: 841568 | C(=O)([C@@H](O)C)C |
| PubChem_Substance: 841709 | CC(=O)C(=O)[O-]•[Na+] |
| PubChem_Substance: 841776 | NCCCC=O |
| PubChem_Substance: 841794 | CC(CN)=O |
| PubChem_Substance: 841889 | CCCCC[CH+]=O |
| PubChem_Substance: 841954 | CC(=O)C(=O)C |
| PubChem_Substance: 854838 | C(CC)(=O)O |
| PubChem_Substance: 85825 | CC(=O)C(C)=C |
| PubChem_Substance: 90476 | CC(=O)C(=O)C(C)C |
| PubChem_Substance: 92515 | O=CCCCC |

The disclosure provides chemicals that can be used as insect repellents and/or masking agents by virtue of their property to block a critical component of the host odor cue. The compounds are effective if they are capable of inhibiting the electrophysiological response of the $CO_2$ neuron.

The volatile compounds of the disclosure have masking and repellant effects by impairing the ability to find a host via long-range cues from $CO_2$ plumes emitted from human breath will be exploited to protect larger area.

The disclosure provides a method of controlling insect attraction to a subject, the method comprising the step of inhibiting gustatory receptor activation (e.g., $CO_2$ sensing gustatory receptors) in the insect or overstimulating the receptor with an antagonist (or a combination of antagonists) selected from the group consisting of 4 to 6 carbon aldehydes (e.g., butanal, pentanal, hexanal), 5 to 8 carbon alcohols (e.g., pentanol, hexanol, cyclohexanol, Z-3-hexen-1-ol, Z-2-hexen-1-ol, 1-hexen-3-ol, 1-hepten-3-ol, 3-hexanol, 2-hexanol and the like), and 3 to 8 carbon mono- or di-ketones (e.g., butanedione (2,3-butanedione), pentanedione and the like), wherein inhibiting expression alters insect responsiveness to carbon dioxide, thereby controlling insect attraction to the subject.

In one embodiment, the gustatory receptor is Gr21a, Gr63a, or a homologue or ortholog thereof, or a combination thereof. In another embodiment, the gustatory receptor is GPRgr22, GPRgr24, or a homologue thereof, or a combination thereof.

In another embodiment, this disclosure provides a method of inhibiting, preventing or reducing the incidence of insect-borne disease in a subject, the method comprising the step of overstimulating or antagonizing a CO2 receptor in an insect with a compounds or combination of compounds selected from the group consisting of 4 to 6 carbon aldehydes (e.g., butanal, penatanal, hexanal), 5 to 8 carbon alcohols (e.g., pentanol, hexanol, cyclohexanol, Z-3-hexen-1-ol, Z-2-hexen-1-ol, 1-hexen-3-ol, 1-hepten-3-ol, 3-hexanol, 2-hexanol and the like), and 3 to 8 carbon mono- or di-ketones (e.g., butanedione (2,3-butanedione), pentanedione and the like), wherein the receptor response to carbon dioxide is modified and attraction to the subject inhibited, thereby inhibiting, preventing or reducing the incidence of insect-borne disease in a subject.

In one embodiment, the disease is malaria, dengue, yellow fever, river blindness, lymphatic filariasis, sleeping sickness, leishmaniasis, epidemic polyarthritis, West Nile virus disease or Australian encephalitis.

In one embodiment, the method of inhibiting, preventing or reducing the incidence of insect-borne disease is via exposing the insect to an agent the antagonizes the CO2 receptor or neuron in the insect.

An active compounds or compounds of the disclosure (e.g., 4 to 6 carbon aldehydes (e.g., butanal, pentanal, hexanal), 5 to 8 carbon alcohols (e.g., pentanol, hexanol, cyclohexanol, Z-3-hexen-1-ol, Z-2-hexen-1-ol, 1-hexen-3-ol, 1-hepten-3-ol, 3-hexanol, 2-hexanol and the like), and 3 to 8 carbon mono- or di-ketones (e.g., butanedione (2,3-butanedione), pentanedione and the like)) may be produced in accordance with techniques known to those skilled in the art, or where novel may be produced by variations of known techniques which will be apparent to those skilled in the art.

The compounds may be used alone or in combination. The compounds of the disclosure may be combined with additional active agent, insecticides and the like in traps to reduce the presence of amount of an insect in the environment. For example, compounds of the disclosure may be used in combination with insect traps (e.g., tape, combustibles, electric traps).

In yet a further embodiment, the compounds may be formulated for application to the skin, clothing or other material. The compounds of the disclosure can "mask" the location of a subject by antagonizing the $CO_2$ receptor neurons of the insect thereby inhibiting the insect's ability to locate a prey.

For example, the compounds of the disclosure may be used as repellents or in compositions comprising said repellant compounds and the use of such repellant compounds and compositions in controlling pests, particularly insect pests such as mosquitoes.

Liquid formulations may be aqueous-based or non-aqueous (e.g., organic solvents), or combinations thereof, and may be employed as lotions, foams, gels, suspensions, emulsions, microemulsions or emulsifiable concentrates or the like. The formulations may be designed to be slowly release from a patch or canister.

The compositions may comprise various combinations of compounds as well as varying concentrations of the compound depending upon the insect to be repelled or masked, the type of surface that the composition will be applied to, or the type of trap to be used. Typically the active ingredient compound of the disclosure (e.g., 4 to 6 carbon aldehydes (e.g., butanal, pentanal, hexanal), 5 to 8 carbon alcohols (e.g., pentanol, hexanol, cyclohexanol, Z-3-hexen-1-ol, Z-2-hexen-1-ol, 1-hexen-3-ol, 1-hepten-3-ol, 3-hexanol, 2-hexanol and the like), and 3 to 8 carbon mono- or di-ketones (e.g., butanedione (2,3-butanedione), pentanedione and the like)) will be present in the composition in a concentration of at least about 0.0001% by weight and may be 10, 50, 99 or 100% by weight of the total composition. The repallant carrier may be from 0.1% to 99.9999% by weight of the total composition. The dry formulations will have from about 0.0001-95% by weight of the pesticide while the liquid formulations will generally have from about 0.0001-60% by weight of the solids in the liquid phase.

As mentioned above, the compositions may be formulated for administration to a subject. Such formulations are typically administered to a subject's skin. The composition may also be formulated for administration to garments, belts, collars, or other articles worn or used by the subject from whom insects are to be repelled. The formulation may be applied to bedding, netting, screens, camping gear and the like. It will be recognized that the application of the compositions and compounds of the disclosure do not only include human subjects, but include canines, equines, bovines and other animals subject to biting insects. For topical application, the formulation may take the form of a spray formulation or a lotion formulation.

The compounds according to the disclosure may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, and the like, if desired, in the form of particular dosage preparations for specific application made therefrom, such as solutions, emulsions, suspensions, powders, pastes, and granules as described herein or as otherwise known in the art which are thus ready for use.

The repellant compounds may be administered with other insect control chemicals, for example, the compositions of the invention may employ various chemicals that affect insect behavior, such as insecticides, attractants and/or repellents, or as otherwise known in the art. The repellant compounds may also be administered with chemosterilants.

In yet another aspect, the volatile compounds of the disclosure may be emitted from vaporizers, treated mats, cylinders, oils, candles, wicked apparatus, fans and the like. Liquid source that can evaporate to form vapors may be used in barns, houses, or patios.

The disclosure also provides chemicals that can be used as bait to lure insects to traps by virtue of activating $CO_2$ neurons. An advantage of these odorants will be their ability to be delivered in an economical and convenient form for use with traps, as compared to bulky $CO_2$ releasing apparatus that are currently in use. This function can be achieved by applying or locating the chemotractant compound of the disclosure near a suction based, or light based, or electric current based or other forms of trapping apparatus.

In contrast to commonly used repellents such as DEET (which has low volatility), the compounds of the disclosure have better volatility and thus are capable of use in large areas and require fewer applications to remain effective.

In addition, most commercially available trapping devices for dipteran insects use $CO_2$ as a lure, generation of which involves high costs and expensive designs. The ability to use volatile odorants that activate the $CO_2$ neuron, and can be supplied cheaply can lead to less expensive designs for traps.

The following examples are intended to illustrate but not limit the disclosure. While they are typical of those that might be used, other procedures known to those skilled in the art may alternatively be used.

EXAMPLES

In order to test whether odourants can directly inhibit $CO_2$-sensitive ab1C neurons (and orthologs thereof) electrophysiology screens were performed in various insect vectors. A number of individual odourants were tested for their ability to inhibit the baseline activity of the neuron using single-sensillum electrophysiology. Candidate odors efficiently inhibit $CO_2$ sensitive neuron in *Culex quinquefasciatus, Aedes aegypti* and *Anopheles gambiae*.

Figure 1:
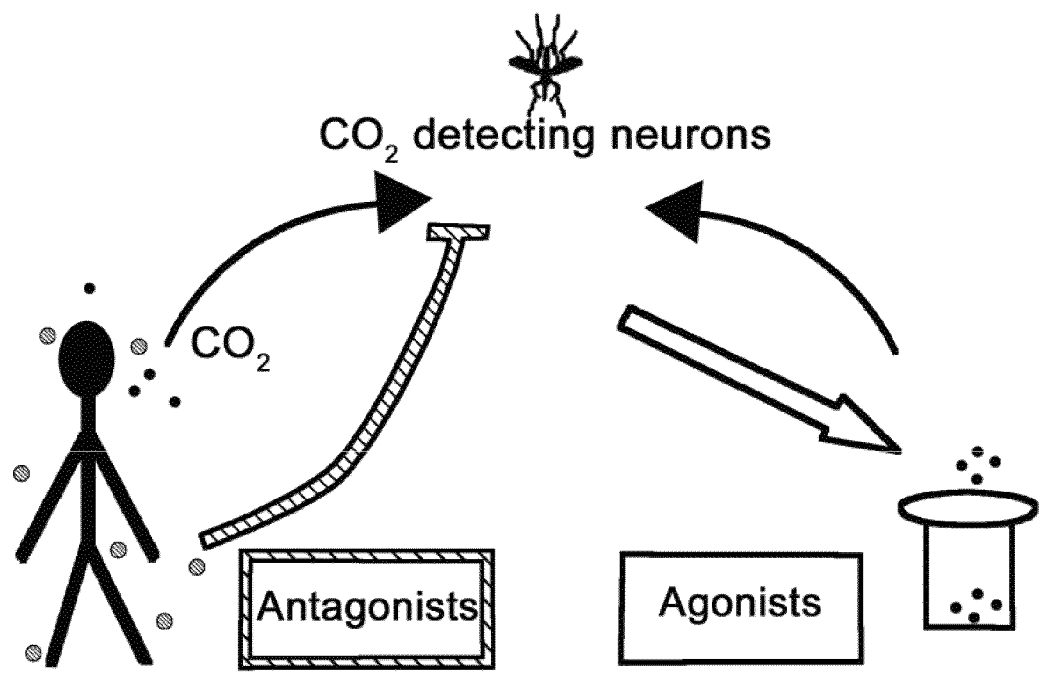
FIG. 1 is a schematic showing the relation of compounds and compositions to $CO_2$ sensing in insect vectors. $CO_2$ emitted by human breath, are detected by the $CO_2$ sensitive neurons on the olfactory organs of vector insects. Volatile chemicals of the disclosure can activate or inhibit the $CO_2$ responsive neuron. Agonists are proposed to be used as lures in traps, and antagonists for disruption of host-seeking behavior as repellents and masking agents.
Figure 2:
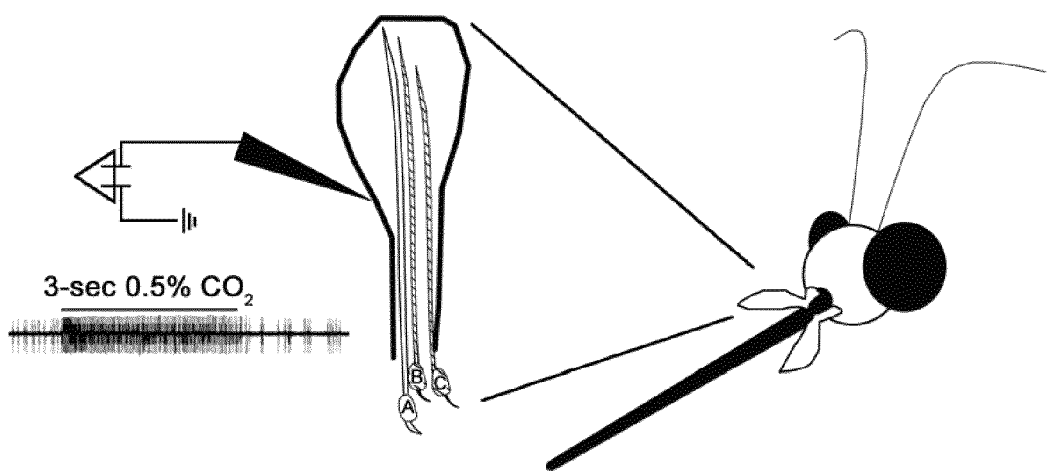
FIG. 2 depicts electrophysiology measurements of the peg sensillum on the mosquito maxillary palp. The palp, indicated in brown in the schematic of the mosquito head, has several peg sensilla. Each peg sensilla (grey club-like structure in the center) contains three olfactory neurons A, B and C as indicated, of which the 'A' neuron gives a robust and specific increase in frequency of action potentials in response to a stimulus of $CO_2$. Extracellular single-unit recordings are performed by inserting a glass microelectrode into the peg sensilla, and puffing an odor such as $CO_2$ towards the mosquito maxillary palps. The signal is amplified to obtain the trace of action potentials. The A neuron has a significantly larger amplitude of action potentials and can be readily distinguished from the spikes elicited by the B and C neurons within the same sensilla.
Figure 3:
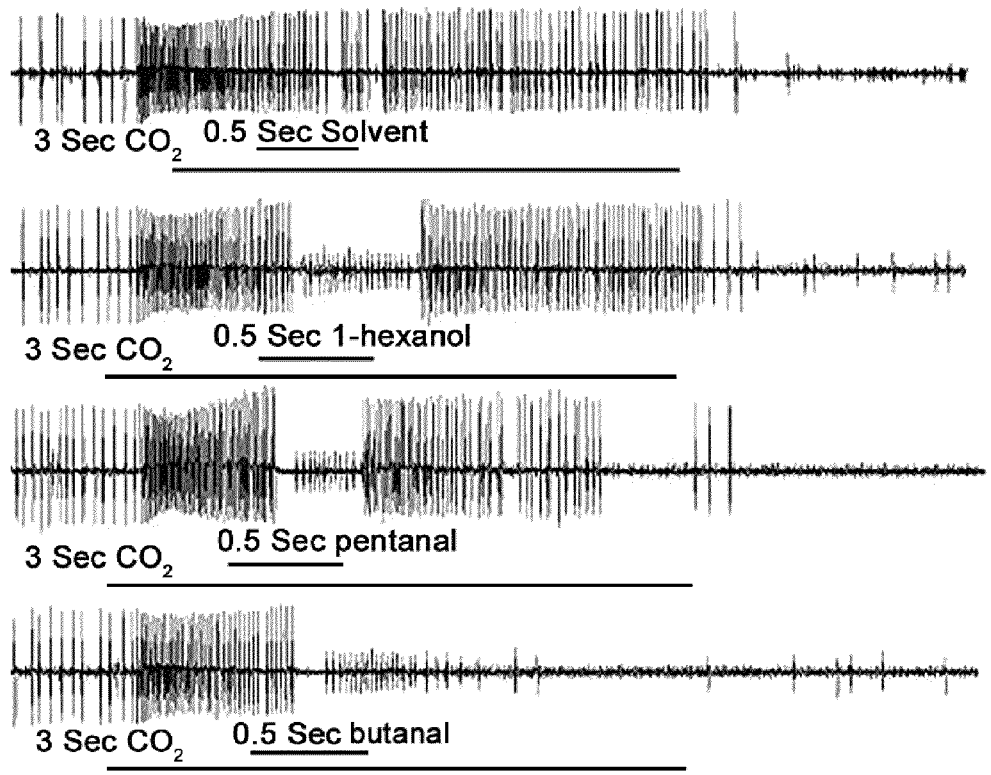
FIG. 3 shows inhibition of the $CO_2$ mediated response by antagonist odors in *Culex quinquefasciatus*. Action potential traces from the peg sensillum of the maxillary palp show spike amplitudes from three neurons, where the highest spike (from neuron A) indicates the $CO_2$ response. A 3-sec stimulus of 0.3% $CO_2$ (indicated by longer black bar), is overlaid with a 0.5-sec stimulus of candidate odors. $CO_2$ stimulus is applied from a tank, while odor is applied from a delivery cartridge containing 50 μl odor at $10^{-1}$ dilution in paraffin oil as solvent, placed on a filter paper disc with indicated odor (colored bars). The two stimuli are delivered from two independent odor delivery systems into a single airstream that is directed over the palps. A constant $CO_2$ stimulus was delivered from a cylinder using a computerized system (Microdata). Odor was delivered in a manner that did not affect the concentration of the $CO_2$ stimulus, from a glass cartridge containing 50 μl of odor at the indicated concentrations, using an independent stimulus delivery system (Syntech).
Figure 4:
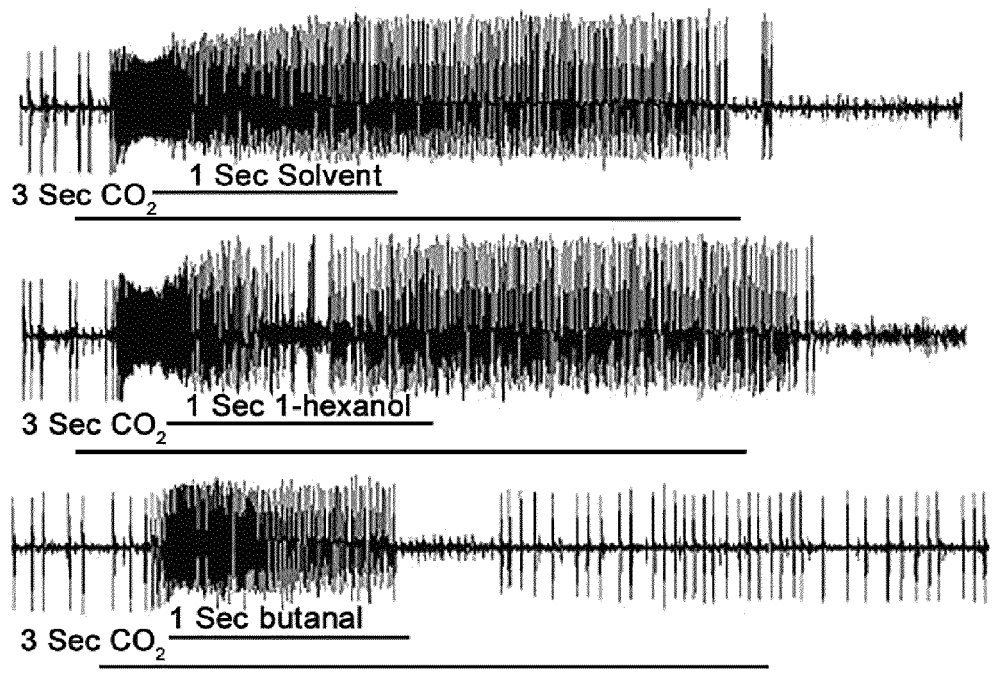
FIG. 4 shows inhibition of the $CO_2$ mediated response by antagonist odors in *Aedes aegypti*. Action potential traces from the peg sensillum of the maxillary palp show spike amplitudes from three neurons, where the highest spike (from neuron A) indicates the $CO_2$ response. A 3-sec stimulus of 0.3% $CO_2$ (indicated by longer black bar), overlaid with a 1-sec stimulus of odor. $CO_2$ and odor stimuli are applied in the same manner as discussed above.
Figure 5:
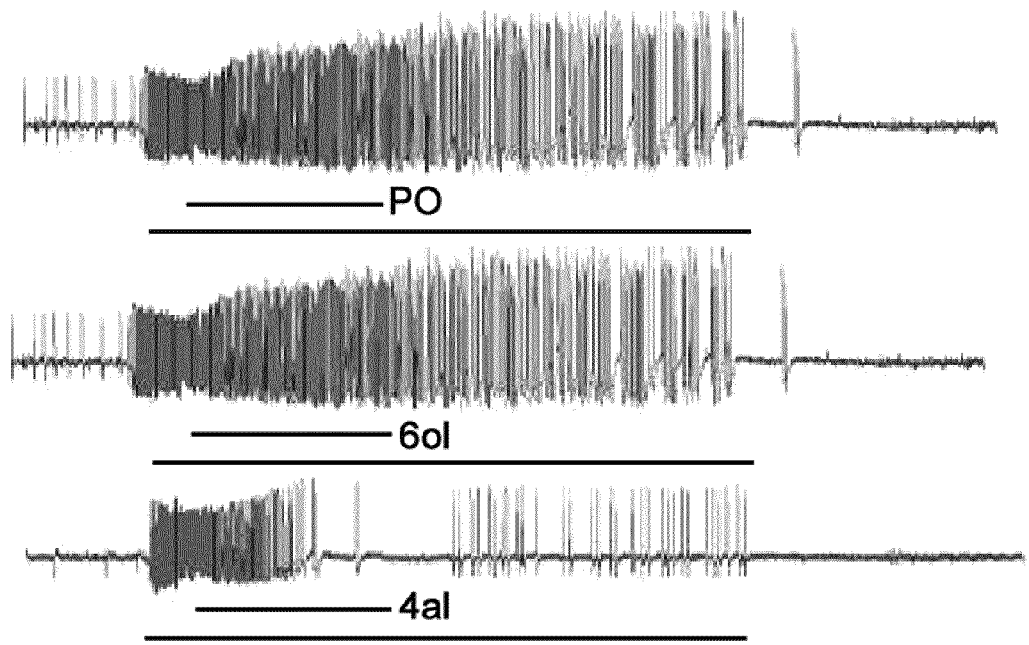
FIG. 5 shows inhibition of the $CO_2$ mediated response by antagonist odors in *Anopheles gambiae*. Action potential traces from the peg sensillum of the maxillary palp show spike amplitudes from three neurons, where the highest spike (from neuron A) indicates the $CO_2$ response. A 3-sec stimulus of 0.3% $CO_2$ (indicated by longer black bar), overlaid with a 1-sec stimulus of odor. $CO_2$ and odor stimuli are applied in the same manner as discussed above.
Figure 6:
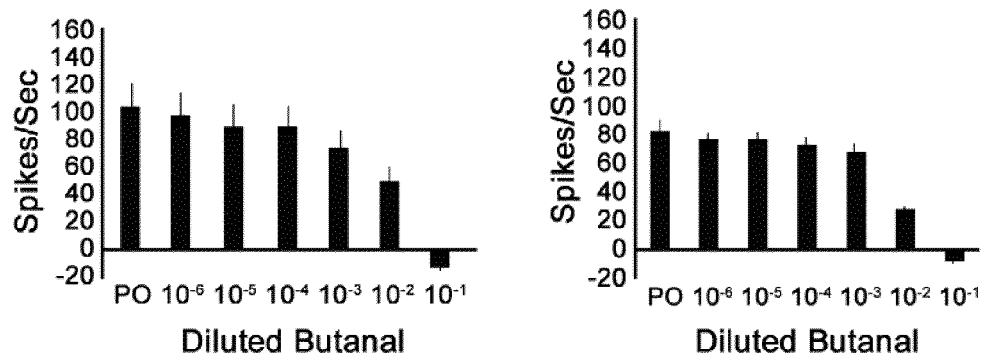
FIG. 6 shows a dose dependent inhibition of $CO_2$ response in *Aedes aegypti*, *Culex quinquefasciatus*, and *Anopheles gambiae*. A 1-sec stimulus of indicated odor was given at the indicated dilution in combination with 3-sec of 0.15% $CO_2$ as described in FIG. 3. n=5. Baseline activity subtracted. Error bars indicate SEM.
Figure 6:
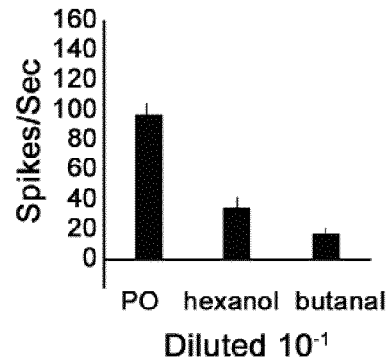
Figure 7:
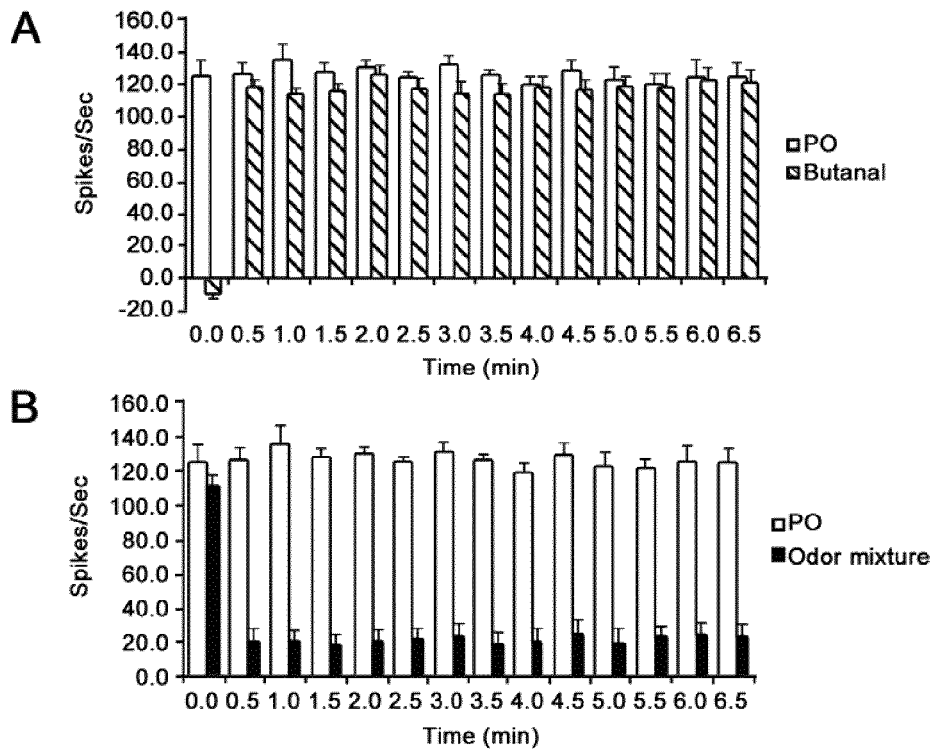
FIG. 7A-B shows pre-exposure to inhibitory odors cause long term reduction in $CO_2$ response in *Aedes aegypti*. The recovery of the response to a 0.3% impulse of $CO_2$ was measured every 30-sec over a 6-min time period, after an initial 3-sec pre-exposure with (A) butanal ($10^{-1}$), or (B) an 'odor mixture' consisting of 1-hexanol, pentanal, butanal, and 2,3-butanedione at $10^{-2}$ concentration. PO=paraffin oil. n=5. Baseline activity subtracted. Error bars indicate SEM.
Figure 8:
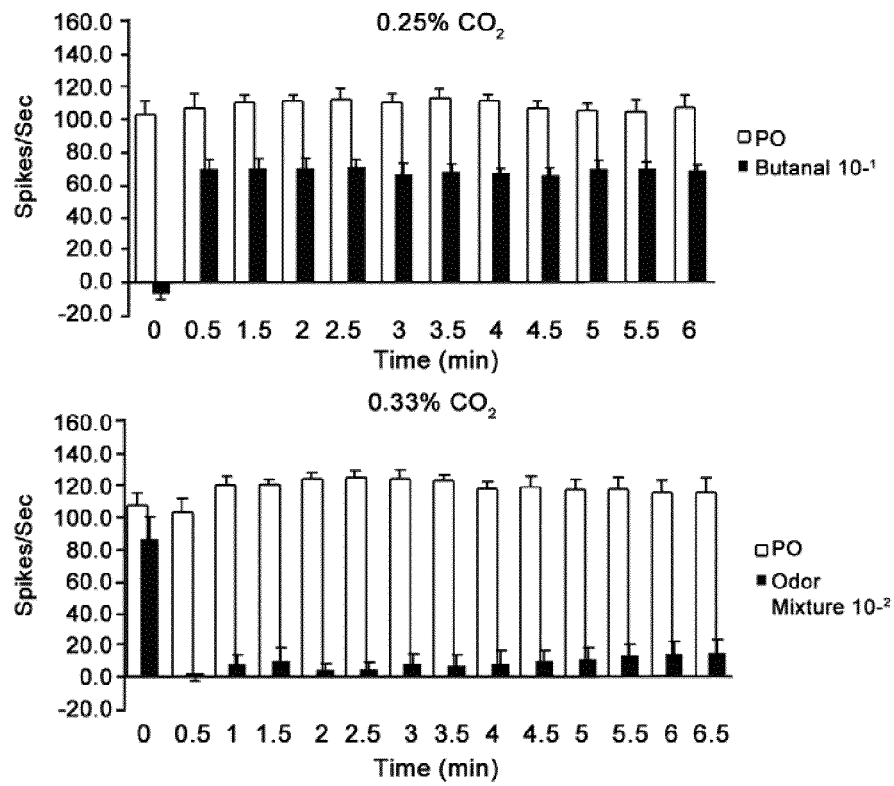
FIG. 8A-B shows pre-exposure to inhibitory odors cause long term reduction in $CO_2$ response in *Culex quinquefasciatus*. The recovery of the response to a 0.25% impulse (top) or 0.3% impulse (bottom) of $CO_2$ was measured every 30-sec over a 6-min time period, after an initial 3-sec pre-exposure with (A) butanal ($10^{-1}$) (top), or (B) an 'odor mixture' consisting of 1-hexanol, pentanal, butanal, and 2,3-butanedione at $10^{-2}$ concentration (bottom). PO=paraffin oil. n=5. Baseline activity subtracted. Error bars indicate SEM.
Figure 9:
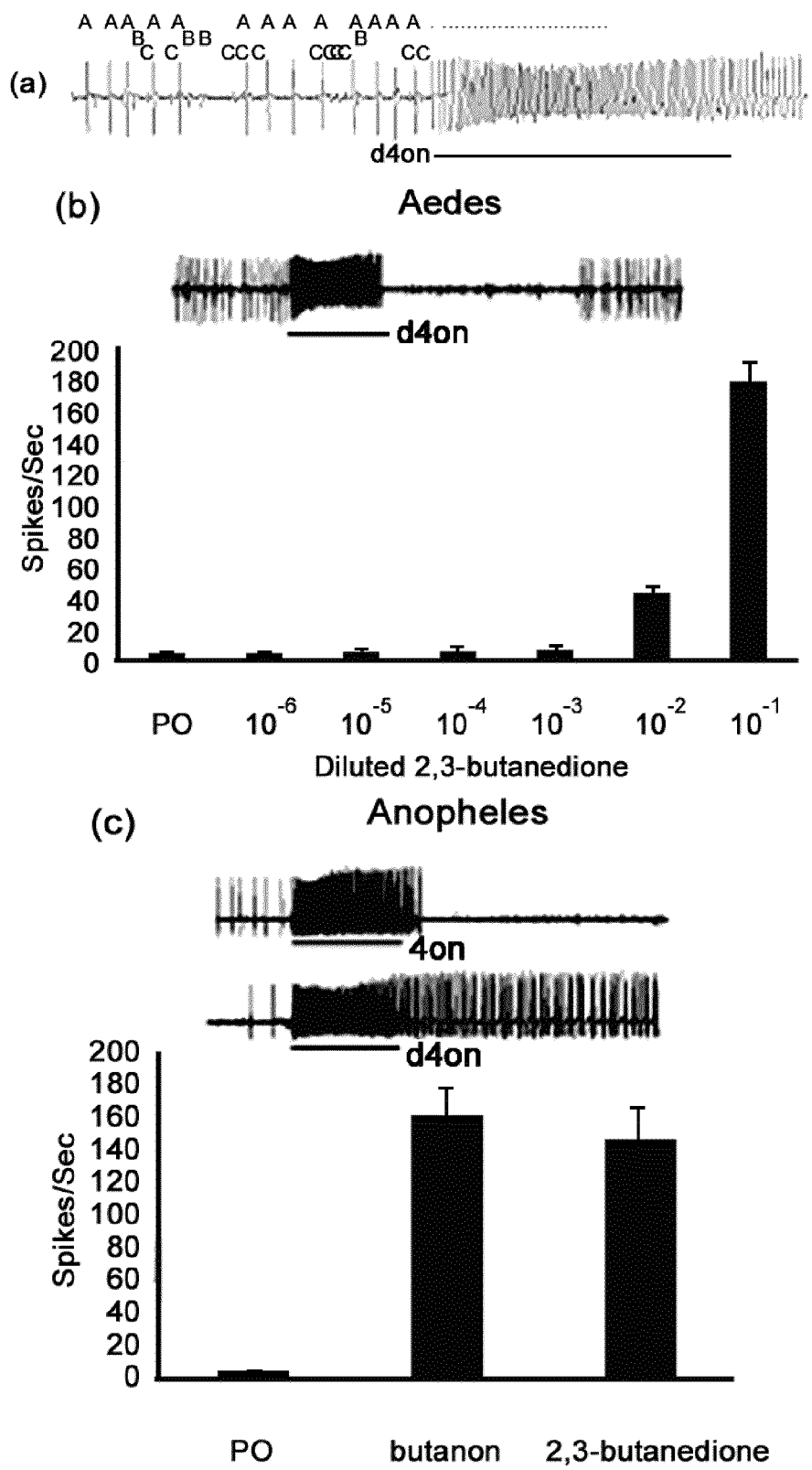
FIG. 9A-E shows activation of $CO_2$ sensitive neuron with a volatile odorant in *Aedes aegypti, Anopheles gambiae*, and *Culex quinquefasciatus*. (a) Action potential traces from the peg sensillum of the maxillary palp show spike amplitudes from three neurons, where the spikes with the largest amplitude belongs to the $CO_2$ sensitive A neuron. (b) 1 sec of the indicated dilution 2,3-butanedione is puffed to Aedes aegypti.
Figure 9:
Figure 9:
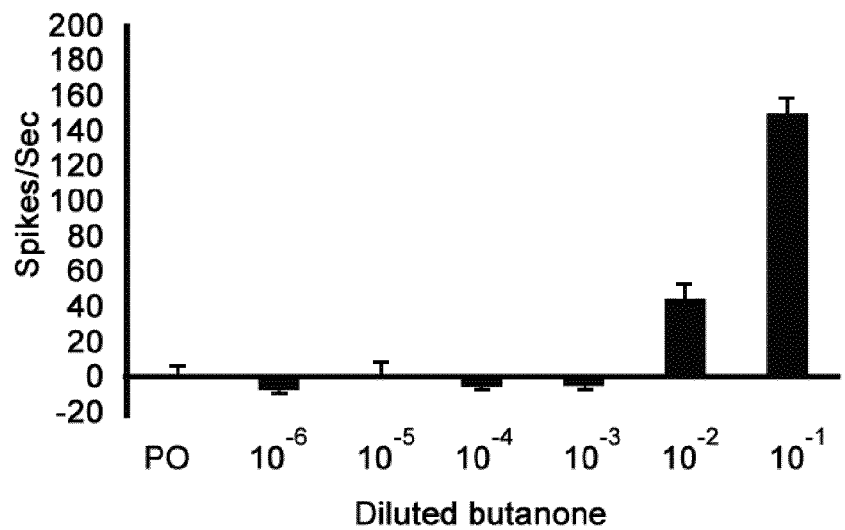
Figure 9:
Figure 9:
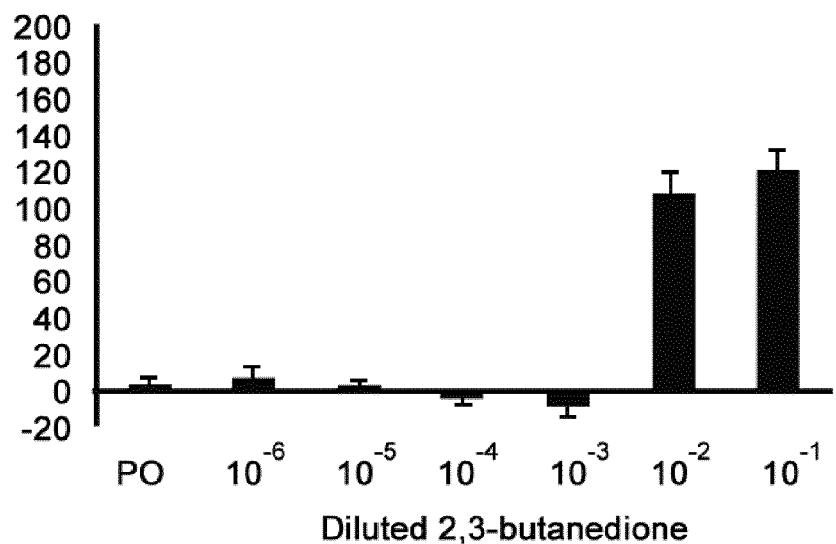
Figure 10:
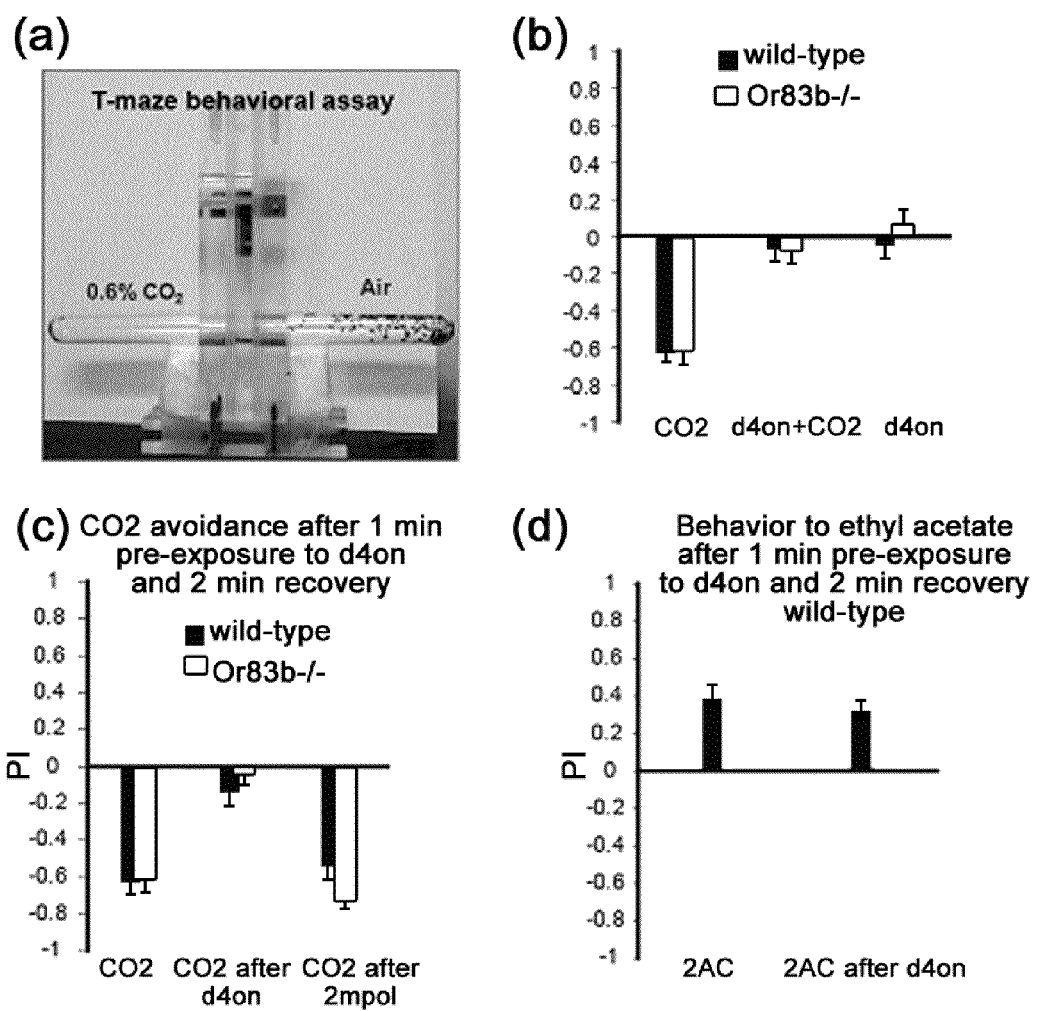

In one experiment single-sensillum electrophysiology was performed on the $CO_2$ sensitive peg sensillum on the maxillary palps of female *Culex quinquefasciatus* to test candidate inhibitory odors. All 4 odors tested efficiently inhibited the $CO_2$ mediated response (FIGS. 3, 4, 5 neuron with larger spike amplitude is inhibited). Odors inhibited $CO_2$ response to varying levels.

Figure 11:
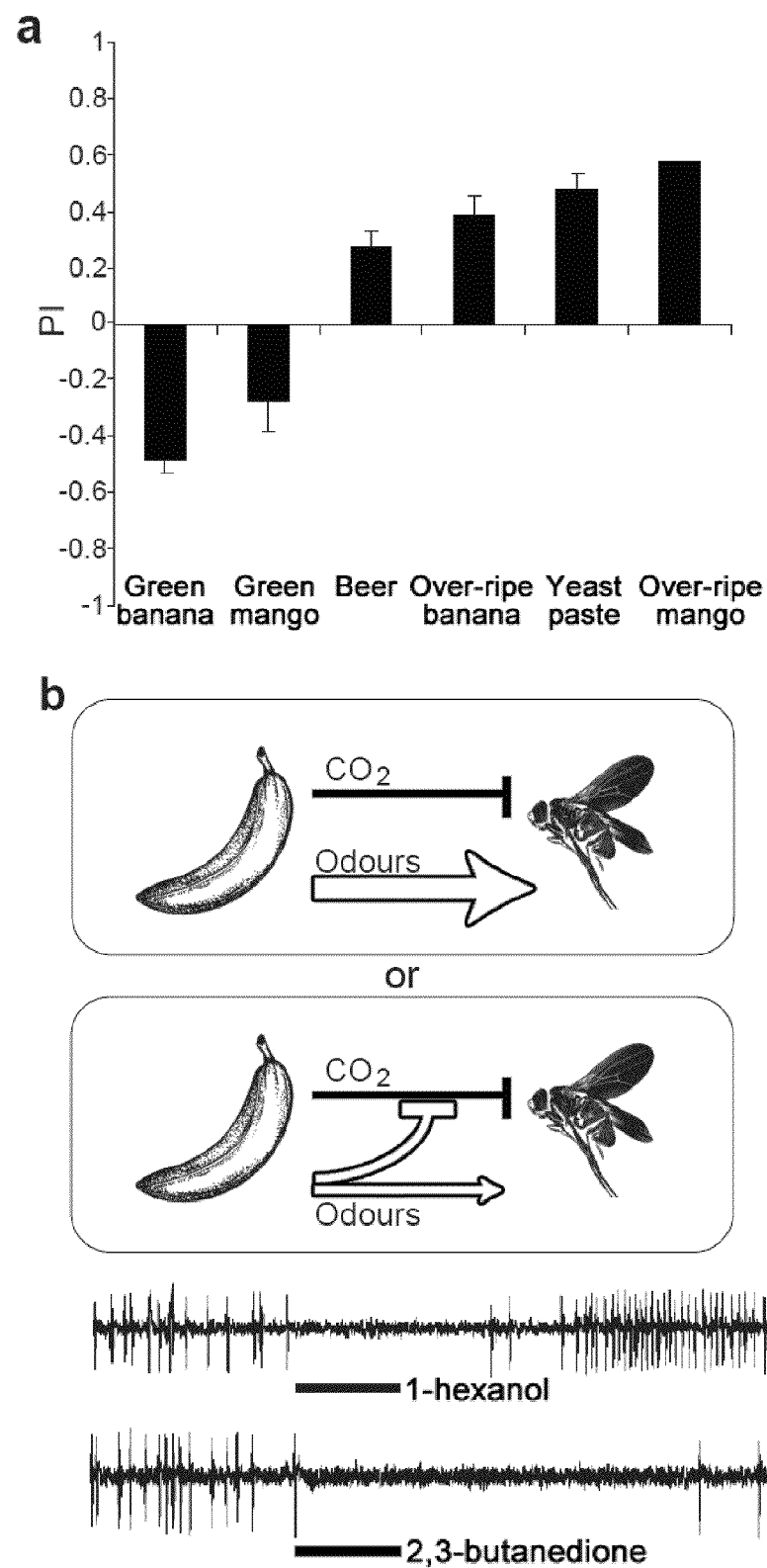
Figure 11:
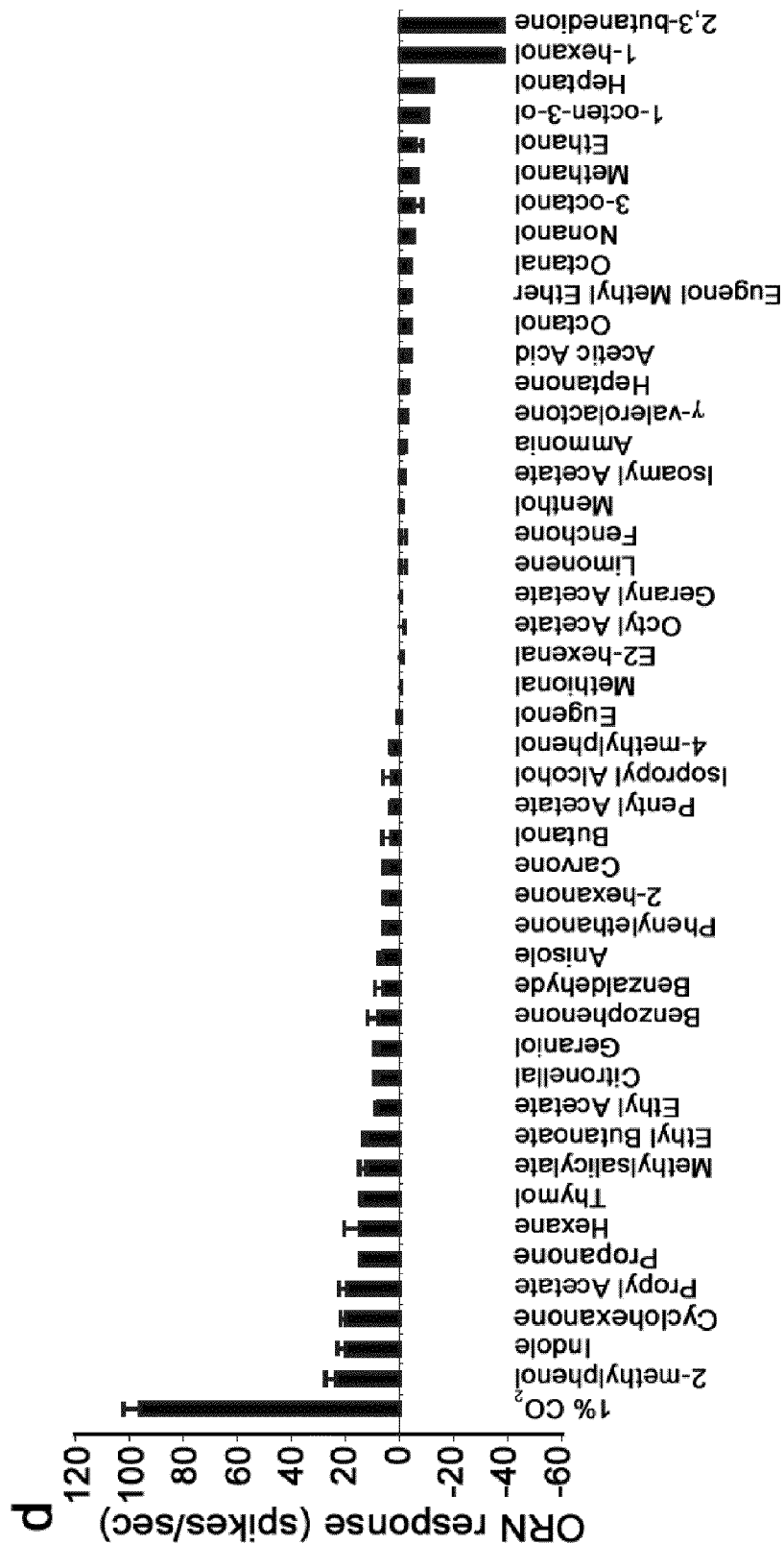

A well-characterized $CO_2$ mediated avoidance behavior was used in a T-maze to test the effect of inhibitory odors. Inhibitory odors can abolish, or significantly reduce $CO_2$ mediated avoidance behavior in Drosophila (FIG. 11). An identical effect in Or83b knockout mutants was also observed, which can only detect $CO_2$ but not the candidate odors. These data suggest that behavior modification of odors act directly by inhibiting $CO_2$ response.

T-maze behavioral testing using *Drosophila* stress odour, $CO_2$, and mixtures were using techniques known in the art, with some modifications. In particular, the entire headspace from 15 ml capped "emitter" or "mock" fly tubes was withdrawn using fresh syringes and needles and infused into fresh capped 15 ml plastic tubes immediately prior to use in the T-maze. To test the response to mixtures, 10 µl of odourant diluted in paraffin oil (at the concentrations indicated) was placed on a Whatman filter paper (6 mm diameter) and placed carefully at the bottom of a fresh 15 ml plastic tube and capped. The additional component (0.1 ml pure $CO_2$ or 15 ml dSO) was injected directly into this capped tube using a syringe, which was then used as the test arm in the T-maze. The tube in the control arm contained filter paper with 10 µl of paraffin oil solvent. The avoidance response was calculated as a Preference Index (PI)=(number of flies in test arm−number of flies in control arm)/(total number of flies in assay). Behavioral responses to $CO_2$ were tested using the T-maze by injecting 0.1 ml of pure $CO_2$ into a capped 15-ml tube with a syringe and needle immediately before the choice assay. For over-ripe fruits, fruits were allowed to ripen and ferment in a sealed plastic container for ~3 weeks, at which point 5 gm of fruit paste was transferred to a fresh 50 ml plastic tube and sealed. After 5 mins at room temperature, 15 ml of headspace was removed using a syringe, and transferred to a fresh 15 ml plastic tube that was used directly as the test arm of the T-maze. Yeast (1 gm) was used to make a paste with 1 ml of 15% sucrose solution, and allowed to sit for 1 hour in a 50 ml sealed tube. The cap was removed to release volatiles and then recapped; 15 ml of headspace was collected 5 mins later and tested as described above. Similarly, 5 min collections of headspace were taken from 5 gm of green fruits, and 5 ml of beer (Stone Pale Ale: Stone brewing company, San Diego, Calif.). Prior to being tested for responses to headspace from fruit, beer and yeast, flies were pre-exposed to the same odours in separate 15 ml tubes for 2 minutes. The avoidance response was calculated as a Preference Index (PI)=(number of flies in test arm−number of flies in control arm)/(total number of flies in assay).

Fly stocks were maintained on standard cornmeal medium at 25° C. Wild-type stock is $w^{1118}$ backcrossed 5 generations to Canton S. The Or83b$^2$ mutant was obtained from the Bloomington stock center. Stocks for Δhalo; Or22a-Gal4 and UAS-Gr21a and UAS-Gr63a were were obtained from colleagues.

Extracellular single-unit recordings were performed. Odourant stimuli were delivered via Pasteur pipette odour cartridges (see, FIG. 16). Chemicals were of the highest purity available, typically>99% (Sigma-Aldrich). All odourants were diluted in paraffin oil. A controlled volume of air 5 ml/sec was puffed through the odour cartridge containing vapours, and was delivered into a constant humidified airstream of 10 ml/sec that was passed over the fly antenna. The odourant vapour present in the cartridge is thus diluted ~3 fold, and the concentration of inhibitory odourants in the air stream that passes over the fly is significantly lower than that applied to the cartridge. $CO_2$ stimulus was pulsed through a separate delivery system that delivered controlled pulses (variable 2.5 ml/sec-6.5 ml/sec) into the same humidified airstream, from either a 1%, 5% or 100% tank of $CO_2$ (Airgas). For delivery of binary mixtures of $CO_2$ with another odourant, a steady concentration of $CO_2$ to the fly preparation was maintained (FIG. 16). Unless mentioned, responses were quantified by subtraction of spontaneous activity from activity during the stimulus. For each inhibitory odourant (some that had a long-term effect on $CO_2$ response), each recording was obtained from a distinct fly, except in the case of experiments looking exclusively at baseline activity.

Using the methods described above, two compounds were initially identified, 1-hexanol and 2,3-butanedione, that strongly inhibit the spontaneous activity of ab1C neurons (FIG. 14C). Both these compounds are present at electrophysiologically relevant concentrations in Drosophila food sources: 1-hexanol has been detected in various types of fruit including mango, melon, strawberry, passion fruit, muskmelon and banana; 2,3-butanedione is a natural by-product of fermentation by yeast and is thus also present in beer.

The two odourants were then tested to determine their ability to inhibit the $CO_2$ response of ab1C neurons. 0.3% $CO_2$ in combination with varying concentrations of each of the two odourants were applied in two separate contexts. In the first context, each odourant was applied for 3-seconds, and a 1-second stimulus of $CO_2$ was overlaid on it (FIG. 12a). In the second experiment, a 3-second stimulus of $CO_2$ was applied first and was overlaid by a 1-second stimulus of the odourant (FIG. 12b). Both 1-hexanol and 2,3-butanedione inhibited $CO_2$ response in a dose-dependent manner, irrespective of whether they are applied prior to or after the presentation of the $CO_2$ stimulus (FIGS. 12a and 12b). Application of 2,3-butanedione at concentrations>$10^{-2}$ silences $CO_2$-responsive neurons completely. For 1-hexanol, the strength of $CO_2$ response inhibition is greater if it is presented subsequent to the $CO_2$ stimulus; the order of presentation is of lesser consequence on the degree of inhibition by 2,3-butanedione. Thus 1-hexanol and 2,3-butanedione, which were identified in a screen for compounds that inhibit the baseline activity of ab1C neurons, are both highly effective at inhibiting the $CO_2$-mediated responses of ab1C neurons at relatively low, physiologically relevant concentrations.

An insect approaching an odour source from a distance likely contacts plumes of $CO_2$, which will vary widely in concentration over baseline atmospheric levels. Thus, experiments were performed to determine how two inhibitors modulate activity of ab1C neurons at different concentrations of $CO_2$, over time. The initial response reflects a rapid increase in frequency of action potentials upon application of $CO_2$, which then quickly adapts over 200-300 msec to stabilize at a lower level (FIG. 12c, PO=paraffin oil). The presence of 2,3-butanedione ($10^{-1}$) leads to a complete inhibition of $CO_2$ response across all tested concentrations up to ~3% $CO_2$, which is comparable to the levels present in exhaled human breath (FIG. 12c). 1-hexanol ($10^{-1}$) also results in a significant reduction of $CO_2$ response across most tested concentrations, but complete inhibition occurs only at 0.1% $CO_2$, which was the lowest concentration tested (FIG. 12c).

Interestingly, at concentrations $\geq 10^{-1}$, 2,3-butanedione silenced the $CO_2$ neuron well beyond the period of application (FIG. 13a, right). This effect was not observed for 1-hexanol at the concentrations tested (FIG. 13a, left). To investigate this further, flies were exposed to a 3-second stimulus of 2,3-butanedione ($10^{-1}$) and subsequently tested for the recovery of ab1C neuron responsiveness by applying a 0.5-second stimulus of 0.3% $CO_2$ every 30 seconds, over a period of 10 minutes (FIG. 13b). Surprisingly, the inhibitory effect of the initial exposure to 2,3-butanedione persisted for an extensive period and responsiveness to $CO_2$ was restored to half-maximal levels only after ~3 minutes. Even at 10 minutes, $CO_2$ response was significantly lower than the response of neurons that had not been pre-exposed to 2,3-butanedione.

In order to identify other $CO_2$ response inhibitors and to gain an understanding of odourant structural features that may play a role in inhibition, a rationally designed panel of odourants that vary in the number of C-atoms and in the nature of the functional group was examined. Based on this analysis, additional structurally-related odourants that also inhibit $CO_2$ response were identified. In particular two aldehydes, butanal and pentanal, were effective inhibitors (FIG. 13c). The inhibitory effects of each of these 4 compounds are specific to the $CO_2$-sensitive neuron; previous studies have shown that all of them excite other classes of Drosophila ORNs, suggesting that they are not general inhibitors of ORN function. Comparison of the 3-D structures of the inhibitors reveals that they can be divided into 3 categories: the 5-8 C alcohols, the 4-5 C aldehydes, and 2,3-butanedione. Surprisingly, these compounds are structurally quite diverse from $CO_2$ (FIG. 13d), thus raising the possibility that they act via allosteric binding sites within the Gr21a/Gr63a receptor, or via other components of the $CO_2$ detection pathway such as specific factors present in the sensillar lymph or within ab1C neurons.

To investigate whether the inhibitors act directly on the $CO_2$ receptor, Gr21a and Gr63a were expressed in an in vivo decoder system called the "empty neuron" (FIG. 14a). As reported previously, expression of Gr21a and Gr63a in the empty ab3A neuron is sufficient to impart $CO_2$ sensitivity, albeit at a lower level (FIGS. 14b, 14c). A significant, dose-dependent inhibition of $CO_2$ response upon simultaneous application of the inhibitory odourants along with $CO_2$ (FIGS. 14b, 14c) was observed. Furthermore, the odourants show differences in the degree of inhibition, as well as in the rate at which inhibition increases with higher concentrations (FIG. 14c). The simplest interpretation of these results is that the odourants inhibit $CO_2$ response by direct interaction with the $CO_2$ receptor Gr21a/Gr63a.

The ability of these inhibitory odourants was then tested in the whole organism. Using a T-maze choice assay the experiment demonstrated that wild-type Drosophila show a robust avoidance behavior to 0.67% $Co_2$ (FIG. 15a). Inclusion of either 1-hexanol or 2,3-butanedione with $CO_2$ results in a reduction in mean avoidance behavior, although to varying degrees; avoidance to $CO_2$ is abolished in the presence of 2,3-butanedione (FIG. 15a). In wild-type Drosophila, however, a number of ORN classes are activated by 1-hexanol and 2,3-butanedione. This raises the possibility that behavioral avoidance to $CO_2$ may be overcome by activation of these other classes of ORNs, rather than by inhibition of $CO_2$-responsive neurons. To distinguish between these possibilities, the behavior of Or83b$^2$ mutant flies in which most of the ORNs are non-functional, but electrophysiological responses to $CO_2$ are not affected were examined (FIGS. 15b, 11a).

Consistent with the electrophysiological analysis, flies lacking Or83b have a robust avoidance response to $CO_2$ (FIG. 15b), which is comparable to the level observed for wild type flies (FIG. 15a). Avoidance is significantly reduced with the addition of either 1-hexanol or 2,3-butanedione with $CO_2$ (FIG. 15b). Taken together these results demonstrate that 1-hexanol and 2,3-butanedione can effectively inhibit $CO_2$-mediated innate avoidance behavior by inhibiting the $CO_2$ receptor.

$CO_2$ is one of the main components of dSO, which is emitted by stressed flies and triggers a robust avoidance behavior in naïve flies. Experiments were performed to examine whether 1-hexanol and 2,3-butanedione can disrupt avoidance to dSO. The experiment demonstrated that naïve flies avoid odour collected from a tube of vortexed flies (dSO), but not that collected from a tube of untreated flies (mock), in a T-maze assay (FIG. 15c). Remarkably, addition of 1-hexanol or 2,3-butanedione to dSO significantly reduced avoidance behavior (FIG. 15c). In fact, addition of 2,3-butanedione acts as such a powerful antidote to dSO, that avoidance behavior is completely abolished (FIG. 15c).

The disclosure provides a novel class of odourants that efficiently inhibit $CO_2$ response in the ab1C neurons of the *Drosophila* antenna and play a role in $CO_2$ masking in mosquitoes. The compounds identified herein can be used to effect environments, inhibit insect targeting and infections. Many vector insect species that carry deadly diseases: *Anopheles gambiae* (malaria), *Aedes aegypti* (dengue and yellow fever), *Culex quinquefasciatus* (filarial and West Nile virus), *Glossina morsitans* (trypanosomiases) and *Lutzomyia longipalpis* (leshmaniasis) can be effected by the compounds and compositions described herein. Most of these species contain highly conserved orthologs of the *Drosophila* $CO_2$ receptors, Gr21a and Gr63a. Odourants that inhibit the *Drosophila* $CO_2$ receptors provide a valuable resource for the identification of economical, environmentally friendly, volatile compounds that effectively block detection of $CO_2$ by other insects, and thus offer a basis for new generations of insect repellents that can reduce the incidence of disease by disrupting $CO_2$-mediated host-seeking behavior.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A composition for disruption of insect host-seeking behavior, comprising an aldehyde selected from the group consisting of butanal, 3-methylbutanal, pentanal, hexanal, and heptanal, an alcohol selected from the group consisting of pentanol, hexanol, and heptanol, and a diketone selected from the group consisting of butane-2,3-dione and pentanedione wherein the composition is formulated as a lotion, a cream, a spray or a dust; wherein the composition disrupts the response to carbon dioxide of the insect in host-seeking behavior.

2. The composition of claim 1, wherein the composition comprises hexanol, pentanal or butanal, and 2,3-butanedione.

3. The composition of claim 1, disposed in a vaporizer, a treated mat, treated outerwear, an oil, a candle, or a wicked apparatus.

4. A method of disrupting the host-seeking behavior of an insect, comprising applying to a subject the composition of claim 1.

5. The method of claim 4, wherein the insect is a mosquito.

6. The method of claim 4, wherein the insect is an *Anopheles* mosquito.

7. The method of claim 4, wherein the insect is an *Aedes* mosquito.

8. The method of claim 4, wherein the insect is an *Culex* mosquito.

9. The method of claim 4, wherein the mosquito is selected from the group consisting of Tiger mosquito, *Aedes aboriginis, Aedes Aegypti, Aedes, albopictus, Aedes cantator, Aedes sierrensis, Aedes sollicitans, Aedes squamiger, Aedes sticticus, Aedes vexans, Anopheles quadrimaculatus, Culex pipiens, Culex quinquefaxciatus*, and any combinations thereof.

10. The method of claim 4, wherein the subject is a mammalian subject.

11. The method of claim 4, wherein the subject is a human subject.

12. The method of claim 4, wherein the subject is a livestock animal.

13. The method of claim 4, wherein the composition is topically applied to the skin of the subject.

14. The method of claim 4, wherein the composition is applied to an article worn by the subject.

15. The composition of claim 1, optionally comprising a solid or liquid carrier material.

16. A dosage form, comprising the composition of claim 1 in the form of a solution, emulsion, suspension, powder, paste, or granule.

* * * * *

UNITED STATES PATENT AND TRADEMARK OFFICE
CERTIFICATE OF CORRECTION

PATENT NO. : 8,945,595 B2  Page 1 of 1
APPLICATION NO. : 12/398164
DATED : February 3, 2015
INVENTOR(S) : Ray et al.

It is certified that error appears in the above-identified patent and that said Letters Patent is hereby corrected as shown below:

On the title page, in column 2, under "Other Publications", line 1, delete "I1II" and insert --III--, therefor

IN THE CLAIMS

In column 40, line 28, in Claim 9, delete "Aedes, albopictus," and insert --Aedes albopictus,--, therefor Signed and Sealed this
Second Day of February, 2016

Michelle K. Lee
*Director of the United States Patent and Trademark Office*